United States Patent
Derickson et al.

(10) Patent No.: US 12,033,534 B2
(45) Date of Patent: Jul. 9, 2024

(54) PREDICTIVE BUILDING EMERGENCY TRAINING AND GUIDANCE SYSTEM

(71) Applicant: Tabor Mountain LLC, Wilmington, DE (US)

(72) Inventors: Russell G. Derickson, Commerce City, CO (US); Susan R. Hilliard, Boulder, CO (US)

(73) Assignee: TABOR MOUNTAIN LLC, Wilmington, DE (US)

( * ) Notice: Subject to any disclaimer, the term of this patent is extended or adjusted under 35 U.S.C. 154(b) by 3 days.

(21) Appl. No.: 17/892,737

(22) Filed: Aug. 22, 2022

(65) Prior Publication Data

US 2023/0046281 A1 Feb. 16, 2023

Related U.S. Application Data

(62) Division of application No. 17/346,680, filed on Jun. 14, 2021, now Pat. No. 11,450,226.
(Continued)

(51) Int. Cl.
*G09B 9/00* (2006.01)
*G06F 30/13* (2020.01)
*G06F 30/27* (2020.01)
*G06N 5/04* (2023.01)
*G06N 20/00* (2019.01)
(Continued)

(52) U.S. Cl.
CPC .............. *G09B 9/00* (2013.01); *G06F 30/13* (2020.01); *G06F 30/27* (2020.01); *G06N 5/04* (2013.01); *G06N 20/00* (2019.01); *G06Q 90/205* (2013.01); *G09B 19/003* (2013.01); *A61B 5/02438* (2013.01); *A61B 5/332* (2021.01); *A61B 5/4266* (2013.01); *A61B 5/6804* (2013.01); *A61B 5/681* (2013.01); *A61B 2505/09* (2013.01)

(58) Field of Classification Search
CPC .......... G06N 20/00; G06N 5/04; G06F 30/13; G06F 30/27; G06Q 90/205; G09B 19/003
See application file for complete search history.

(56) References Cited

U.S. PATENT DOCUMENTS 6,000,505 A 12/1999 Allen
10,553,085 B1 2/2020 Derickson
(Continued)

FOREIGN PATENT DOCUMENTS

WO WO-2020055585 A1 * 3/2020 ............. A62C 37/40

*Primary Examiner* — Kesha Frisby
(74) *Attorney, Agent, or Firm* — Barnes & Thornburg LLP

(57) ABSTRACT

The disclosed technology provides for generating simulation training models that can be used to prepare people (i.e., building occupants, first responders) to safely and calmly respond to emergencies, such as fires in high-rise buildings. Using the training models, people can better cope with decision-making during emergencies. The disclosed technology also uses signaling devices, wearables, and other devices and sensors distributed throughout a building to provide egress or stay-in-place guidance to people located in the building during an emergency. Audio and/or visual information can be outputted to people to guide them along a safe pathway that is selected to provide safe egress for the person, including anticipating and protecting the person from changing emergency conditions within the building and in response to how the person responded to the simulation training models.

20 Claims, 19 Drawing Sheets

Related U.S. Application Data

(60) Provisional application No. 63/088,815, filed on Oct. 7, 2020.

(51) Int. Cl.
*G06Q 90/00* (2006.01)
*G09B 19/00* (2006.01)
 *A61B 5/00* (2006.01)
 *A61B 5/024* (2006.01)
 *A61B 5/332* (2021.01)

(56) References Cited

U.S. PATENT DOCUMENTS

| | | |
|---|---|---|
| 11,043,095 B1 | 6/2021 | Derickson |
| 2011/0155516 A1 | 6/2011 | Mason |
| 2016/0027266 A1 | 1/2016 | McDonough et al. |
| 2019/0171780 A1 | 6/2019 | Santarone et al. |
| 2021/0201635 A1 | 7/2021 | Fernandez-Orellana |

* cited by examiner

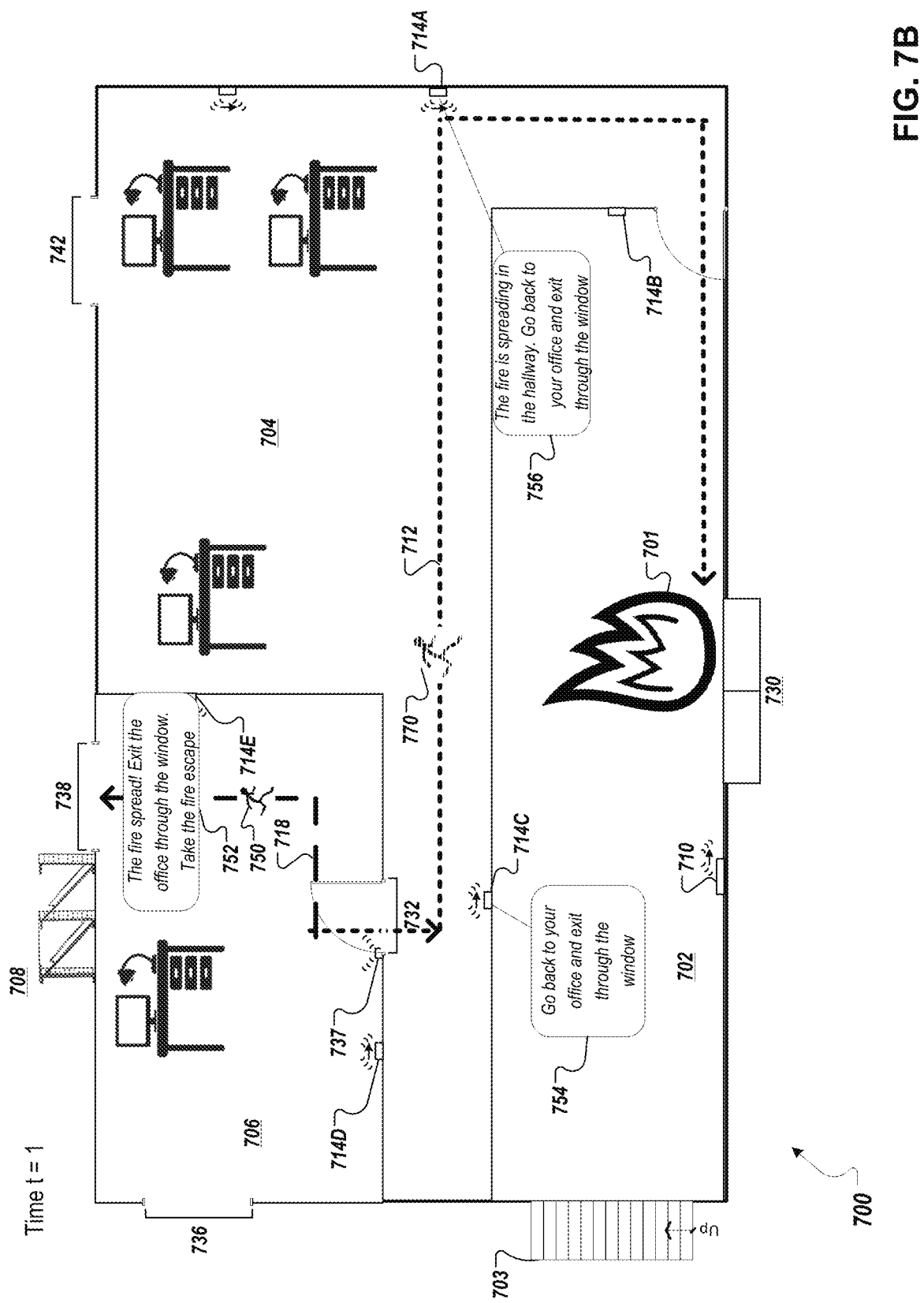

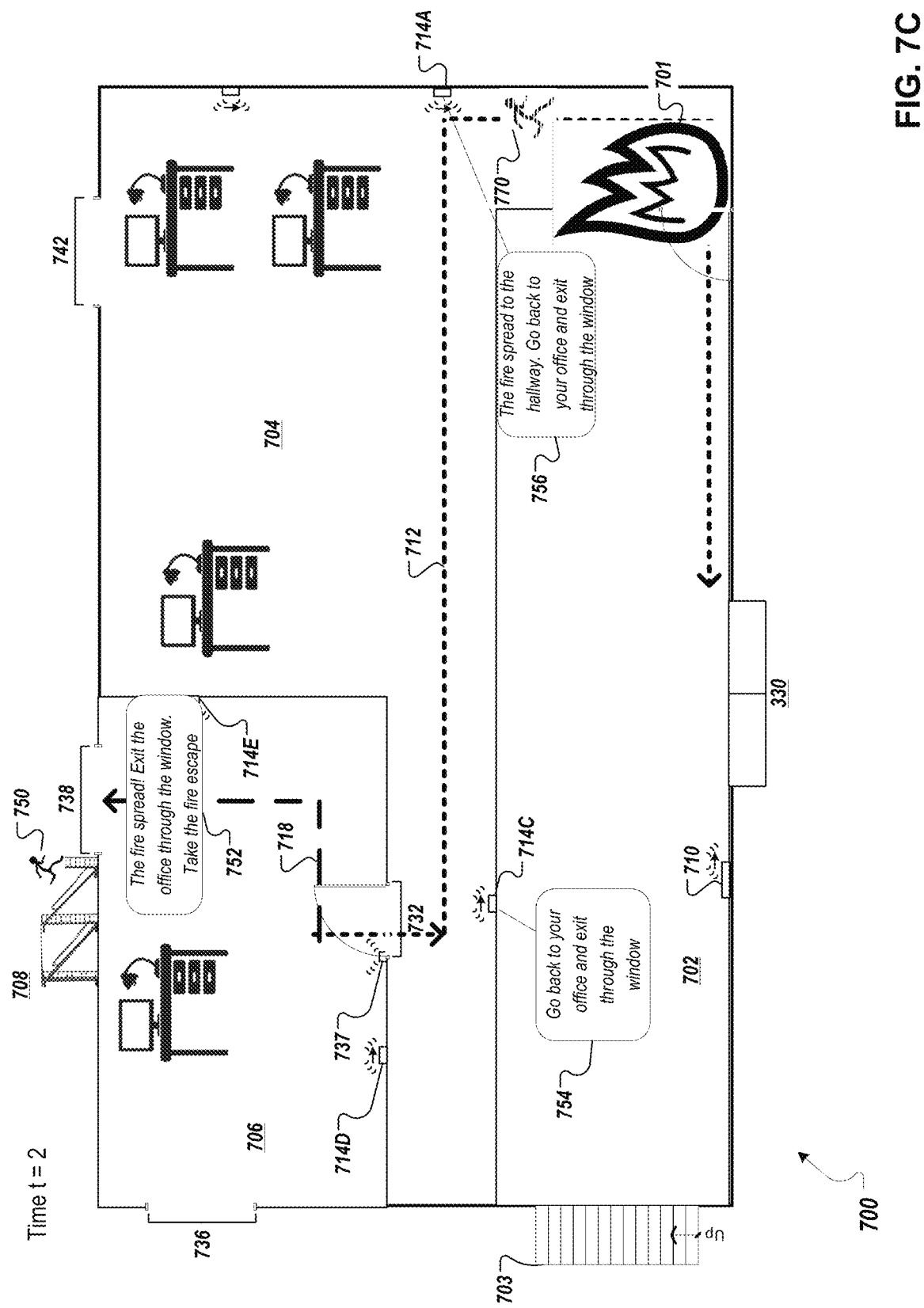

PREDICTIVE BUILDING EMERGENCY TRAINING AND GUIDANCE SYSTEM

CROSS-REFERENCE TO RELATED APPLICATIONS

This application is a divisional of U.S. application Ser. No. 17/346,680, filed on Jun. 14, 2021, which claims the benefit of U.S. Provisional Application Ser. No. 63/088,815, filed Oct. 7, 2020. The disclosure of the prior application is considered part of (and is incorporated by reference in) the disclosure of this application.

TECHNICAL FIELD

This document generally describes technology for training people how to safely egress from a building and guiding people out of a building during an emergency, such as a fire.

BACKGROUND

Fire districts strongly urge building occupants to have a fire escape plan. Implementing a fire escape plan during an emergency requires building occupants and other related parties, such as emergency crews, to understand and feel comfortable with the escape plan. Fire escape plan recommendations include taking stock of each occupant in the building and identifying multiple, safe, and quick escape pathways from each room in the building. Today, many buildings, such as homes and/or low-rise buildings, are constructed with composite materials rather than real wood. As a result, these new constructions are more likely to be engulfed in flames in less time. In addition, high-rise buildings can experience emergencies, such as fires, on one or more levels, where the only escape routes may be through an elevator, stairwell, or high-rise window. Therefore, it is important that occupants in any type of building know how to safely egress without chaotic scrambling before the entire building is in flames.

SUMMARY

This document generally describes technology for training people how to safely egress from a building and more safely guiding people out the building during emergencies in ways that are more robust and adaptable to readily changing conditions during an emergency. In particular, the disclosed technology provides for enhanced training and operational management of emergencies in buildings such as high-rises.

The disclosed technology can provide for enhanced occupant safety training and guidance during emergencies. The disclosed technology can prepare building occupants for safely egressing or staying in place during an emergency. For example, the occupants can undergo simulated fire training models, as disclosed herein, using augmented, virtual, mixed, and/or extended reality (AR, VR, MR, XR). The occupants can be trained in different scenarios of differing complexity, such that the occupants can become inoculated to different stress levels and emergency response plans. For example, without proper training, occupants may be uncomfortable with an emergency response plan that requires them to stay in place. With proper training, as disclosed herein, occupants can become more comfortable with a stay-in-place response plan such that in a real-time emergency, the occupants can calmly and safely adopt that plan. Chaos and stress during real-time emergencies can be reduced and/or avoided. Moreover, the disclosed technology can assist occupants in making decisions about adopting a response plan during a real-time emergency. Guidance can be provided and/or outputted in a physical environment that the occupants are located in or on a wearable device or other computing device of the occupants. For example, guidance can be audio that is outputted through speakers in a building during an emergency. As another example, guidance can be directions that are displayed on a smartwatch worn by an occupant. In yet another example, guidance can be directions that are displayed on a smartphone or tablet held by the occupant. During real-time emergencies, the disclosed technology can be beneficial to reduce the stresses associated with determining how to safely egress when surrounded by unpredictable environmental behaviors (i.e., excessive smoke, heat or fire) that compromise the ability to make the right decisions.

In addition, the disclosed technology can provide for enhanced safety training for emergency response teams (i.e., first responders) and rescue guidance for the teams during emergencies. The disclosed technology can coordinate and guide emergency response teams, such as first responders, as they transit to a site of an emergency or they perform rescue of occupants at the site. For example, the first responders, as well as other stakeholders like building occupants and building security/emergency response teams, can undergo simulated fire training models as part of routine training. During actual emergencies, first responders can be called to a high-rise building where there is a fire on a top floor. While getting to the building, each first responder can put on/use an AR or XR device, such as an AR or XR headset, and undergo a simulated fire training model in order to understand they will get into the building and bring to safety each of the occupants. During an emergency, the disclosed technology can also provide critical communications amongst first responders, first responders and building occupants, and other essential stakeholders.

Fire safety training with augmented and/or virtual reality can assist relevant stakeholders (i.e., occupants, first responders, building managers, etc.) in knowing how to safely, quickly, and calmly evacuate during high-rise emergencies. High-rise buildings have egress strategies through stairways and occupant evacuation elevators (OEEs). Also, a "stay-in-place" strategy can sometimes be the safest strategy during an emergency in a high-rise building with fires localized to one area. Training building occupants to remain in place during an emergency using a simulated training model can teach the occupants to remain calm and accepting of such an egress strategy during a real-time emergency. Moreover, training occupants with the simulated training model can teach them that egressing through an elevator that is not an OEE or a window is not a safe strategy, thereby teaching occupants to use stairways and how to remain calm and patient during a real-time emergency, how to overcome wrong actions and/or chaotic thoughts, and how to provide useful information to first responders or other essential stakeholders (i.e., building manager/security officer). The disclosed technology embodies an understanding of basic human behavior when stressed by an emergency and provides essential stakeholders with more situational awareness so that during a real-time emergency, the stakeholders are not searching for information, chaotic, and delaying their ability to safely egress. The disclosed technology guides stakeholders on how to act during the training model but also in real-time.

Artificial intelligence (AI), predictive analytics, and/or machine learning algorithms can be implemented in the disclosed technology in order to improve simulated fire training models. These techniques can be used to ensure that essential stakeholders can calmly respond to different types of emergencies and fire scenarios. As a result, essential stakeholders can develop more robust decision-making and acting techniques to deal with any type of emergency. These techniques can further use information collected in real-time (i.e., during a fire emergency) and/or during training to improve the training models and generate training models having varying degrees of complexity and challenges. Doing so can help the essential stakeholders learn how to cope and make decisions in different types of emergencies such that in a real-time emergency, the stakeholders are better prepared to decide and act on their own.

Biometric sensors can be attached/worn by stakeholders who undergo the training models in order to log their heartrates, sweating, and other biometric data that is helpful in determining whether someone is stressed or unable to focus on safely egressing during an emergency. If, for example, a trainee's heartrate increases above a predetermined threshold while undergoing a training model, then it can be determined that the trainee needs to undergo additional training models in order to be more comfortable in an emergency, receive guided instructions, and/or take an alternative egress option. If, for example, a trainee's heartrate remains constant and/or below a predetermined threshold while undergoing a training model, then the trainee may not require additional training models and/or the trainee can undergo more challenging training models. In such situations, the trainee may receive no guidance from the technology disclosed herein. In other words, the technology described herein can automatically activate guidance when it is sensed (i.e., using the biometric sensors) that the trainee is struggling to observe, orient, decide, and act on their own. Activating guidance instructions generated by the disclosed technology and using AI and/or predictive analytics can assist the trainee in deciding what to do and acting in scenarios where the trainee is experiencing high levels of stress or facing unexpected behaviors and/or conditions in such scenarios. Moreover, the automatic activation of guidance is applicable not only to the training models but also to real-time emergencies. For example, in real-time emergencies, automatic activation of guidance can occur seamlessly so as to not distract the stakeholder (i.e., first responder) from making decisions and acting, but also to ensure that the stakeholder makes the best decisions. This can be beneficial in a situation where the stakeholder is not experiencing a high level of stress and can still make coherent decisions but a condition (e.g., smoke) in the physical environment obstructs the stakeholder's vision or ability to appropriately assess the physical environment.

The disclosed technology can implement AI and/or predictive analytics in order to develop mental models for the essential stakeholders. The disclosed technology can lessen a psychological burden on stakeholders such as building occupants who generally are not trained or suited for effective, coherent thought and action when faced with real-time emergencies. Training can also help first responders to know how to deal with uncertainty, incomplete data, or unexpected surprises while implementing a rescue plan in real-time. They can be trained in advance, on the way to an emergency, and even receive input during an emergency. A combination of human response and predictive analytics and/or AI via the device can improve the first responders' ability to respond to the emergency as well as reduce potential stress or mental incoherency that may occur when presented with a real-time emergency. The disclosed technology can generate mental models for the occupants to help them better cope with high stress and uncertainty in real-time emergencies. The mental models can accommodate for observing, predicting, and deciding what actions the stakeholders can take during an emergency, and then present those actions to the stakeholders via the simulated fire training models. Doing so can help reduce stress and/or indecisiveness that may occur to a building occupant, first responder and/or other stakeholder during a real-time emergency.

Developing mental models and incorporating augmented reality and/or extended reality into both training and real-time emergency scenarios can assist and improve essential stakeholders' situational awareness. The disclosed technology can provide vital data to the stakeholders from which to orient, decide, and act in any emergency situation. The improved situational awareness can help the stakeholders see beyond their actual range and scope of vision such that the stakeholders can make key observations without missing or misinterpreting information pertinent to calmly, safely, and quickly egress from a building. Moreover, the disclosed technology, using predictive analytics, AI, and/or augmented reality, can assist first responders in determining what they should do before arriving at the scene of the emergency. Doing so can reduce potential human error made in real-time when responding to the emergency.

The disclosed technology can implement augmented reality (AR), mixed reality (MR), virtual reality (VR), and/or extended reality (XR) for training people before an emergency and operation during an emergency in a building. Sensors can be placed throughout the building in order to detect and manage fire and/or smoke conditions, locate occupants, and/or direct occupants/responders to safely egress from the building.

The disclosed technology uses a network to communicate between sensors and a computer system for generating training simulation models. The computer system can receive information about different buildings, such as floorplans, egress strategies, and egress instructions. In some implementations, this information can be received from sensors and/or other devices in buildings that communicate with the computer system via the network. The computer system can generate simulated fire training models based on identifying specifics about a particular building. The computer system can also generate simulated fire training models based on identifying commonalities between the building information. As a result, the generated training models can be implemented by any first responders, occupants, or other essential stakeholders in any building. In other implementations, training models can be generated based on specific information about a particular building. The computer system can further implement the generated training models in different buildings. The computer system can receive information (i.e., biometric data) about trainees as they undergo the training models and analyze that information in order to ameliorate/improve the training models. The computer system can detect trainee stress levels and determine what in a simulated training model caused the increased stress levels. Based on such determinations, the computer system can generate simulated training models that replicate stress-inducing scenarios. The computer system can also generate mental models that assist essential stakeholders in making calm decisions during emergencies. The computer system can provide these additional and/or enhanced training models to particular buildings and/or stakeholders in order to assist stakeholders in more calmly responding to emergencies and safely egressing in real-time.

The disclosed technology further provides for building egress guidance in a way that not only takes into consideration current conditions within a building, but also anticipates changes to those conditions during the period of time when occupants will be exiting the building (or otherwise moving to safe locations within the building) so as to select egress pathways and strategies that will provide for safe egress during the entirety of the egress period. For instance, assume an occupant is in their office and a fire starts in an elevator hallway of a high-rise building. At the time the fire is detected, egress through a stairwell is available. However, simply guiding the occupant to the stairwell may not be optimal because, by the time the occupant moves from the office to the stairwell, the fire may have spread to down the hallway and to the stairwell, blocking the occupant's exit from the high-rise floor and potentially also blocking retreat and other exits. The disclosed technology leverages machine learning and/or AI techniques to predict the spread of fire (and/or other emergency conditions in a building) relative to the movement of occupants within a building in order to select egress pathways out of a building that will be safe during the entire duration while an occupant exits a building or otherwise moves to safety. The use of machine learning and/or AI techniques makes the disclosed technology performance-based, as opposed to an inflexible prescriptive approach, which is critical to ensure safety during a fire emergency. The performance-based techniques and technology described throughout this disclosure address specifics of each building, such as floorplans, vulnerabilities in the building, fault detection for objects (i.e., garbage chutes, kitchen appliances, etc.) related to fire initiation, potential fire paths, fire loads in various zones, age and mobility of building occupants, and many other considerations in order to create comprehensive assessments to safely and quickly egress during a fire. Therefore, the disclosed technology is able to assess, both before a fire and in real-time, various fire scenarios in differing situations and design fire safety plans based on any identified and/or predicted risks.

The disclosed technology uses signaling devices and sensors that are distributed throughout a building in order to provide egress guidance to people located in a building when an emergency occurs. Such signaling devices can be located at or near doors, windows, and/or other junction points between different parts of a building (i.e., passageways between different offices, hallways, etc.). Signaling devices can provide audio and/or visual information to occupants to guide them along a safe pathway that is selected to provide safe egress for the occupant, including anticipating and protecting the occupant from changing emergency conditions within the building. For example, signaling devices can include lights that are positioned at or near doorways and windows in a home, and that provide a simple visual cue (i.e., red light, green light) as to whether it is safe for an occupant to attempt egress through the doorway or window. Signaling devices can additionally and/or alternatively include speakers and/or other audio output devices that are capable of outputting audio commands to occupants, such as directing the occupant to egress through the front door or to egress through the window in the room. Other types and combinations of outputs are also possible.

The signaling devices can be part of a network of devices in a building that are designed to provide egress guidance to occupants in the building. The network of devices can include, for example, signaling devices, a controller device, and sensors that are positioned throughout the building. The controller device can receive information about environmental conditions in a building from the sensors, which may have wired and/or wireless communication pathways to the controller. The controller device may determine current conditions in the building from these signals, and may distribute information about the current conditions in the building to the signaling devices, which may use that information to select egress strategies and provide egress guidance to people located nearby. The signaling devices can be preconfigured with egress strategies that are predetermined by a server system (i.e., cloud based computer system) based on simulations of emergency scenarios in the building. For example, it may not be feasible or timely to simulate and predict the spread of a fire in a building when the fire is occurring, which could lead to poor and potentially unsafe egress guidance to occupants in the building. To avoid this and maintain optimal egress guidance, the processing of simulations, predicted spread of emergency situations, and resulting selection of egress strategies can be time shifted so that it is processed (i.e., processed on a server system) before an emergency situation occurs. This preprocessing can generate egress strategies that map current conditions to particular egress guidance that takes into account predictions on the spread of emergency conditions in the building. So during runtime, the current conditions in the building can be fed into the predetermined egress strategies to select an optimal egress pathway to use for guiding occupants out of the building, all without requiring the computational resources during the emergency situation to predict the spread of the emergency condition in the building and to simulate egress during those changing conditions. Signaling devices can be preloaded with these egress strategies, which can be the result of a pre-event assessment of the building, its layout, and conditions, and predictive analytics surrounding emergency conditions in the building and egress simulations.

In addition to the system configuration described in the preceding paragraph, preloading signaling devices with egress strategies can also permit them to provide safe egress guidance independently and autonomously, and without dependence on the network being available or other devices to provide guidance. For example, during a fire some components of an egress system may be destroyed. In a system where the signaling device is dependent on other devices, such destruction of egress system components could lead to a collapse of the system as a whole. In contrast, the disclosed technology permits for signaling devices to receive environmental conditions from other devices (to the extent available, and in addition to making their own determinations about environmental conditions) and to act independently using that information to provide egress guidance. Signaling devices can additionally include their own backup power sources, so that they are able to continue operating in the event an external power source to the signaling is unavailable. Such features can provide for a more robust system that is able to continue to provide safe and improved egress guidance to occupants in a building, and in a way that is not susceptible to one or more components going down during an emergency.

In some implementations, an emergency evacuation training system can include a building assessment computing device that collects evacuation information of at least one building, an output device that outputs a training simulation model to a user, an input device that obtains training results of the user, a biometric sensor that measures biometric characteristics of the user, and a training computing system that performs operations. The training computing system can receive, from the building assessment computing device, the evacuation information of the at least one building, generate the training simulation model that provides one or more emergency evacuation plans transmit the training simulation model to the output device, wherein the output device executes the training simulation model and outputs the one or more emergency evacuation plans for the user, receive, from the input device, the training results of the user, receive, from the biometric sensor, the biometric characteristics of the user, determine training performance of the user based on the training results and the biometric characteristics, and adjust the training simulation model based on the determined training performance of the user. The training computing system can further transmit the adjusted training simulation model to the output device, wherein the output device executes the adjusted training simulation model for retraining of the user. The training computing system can additionally perform operations including generating a mental model of the user based on the training performance. The mental model can indicate a level of stress of the user, how long it took the user to complete the training simulation model, or what guidance the user received to complete the training model.

In some implementations, the evacuation information of the at least one building can include locations of fire detectors and smoke detectors, occupant information, information about evacuation guidance devices, locations and types of emergency equipment, information about a sprinkler system, and information about elevators. The output device can be a mobile device, a virtual reality ("VR") device, or a wearable device. The biometric sensor can be a wearable device, a heartrate monitor, a smartwatch, or smart clothing. The biometric characteristics can be a heartrate, an EKG value, or an amount of sweat. The training results can include whether the user completes at least one of the emergency evacuation plans, which emergency evacuation plan the user chose, how fast the user completed the plan, and whether the user received guidance to complete the plan. In some implementations, the at least one building includes a plurality of buildings, and generating the training simulation model can further include identifying one or more commonalities from the evacuation information of the plurality of buildings and generating the training simulation model based on the commonalities. The commonalities can include locations of sensors in a building, egress strategies, egress instructions, or building layouts. In some implementations, the user can be a first responder, a building occupant, a building security officer, or an emergency incident commander. The determined training performance can include an indication of a level of stress during execution of the training simulation model exceeding a predetermined threshold level of stress. Moreover, the level of stress during execution of the training simulation model is based, at least in part, on a duration of time for the user to complete the training simulation model exceeding a predetermined threshold amount of time expected to complete the training simulation model.

In another implementation, an emergency evacuation system can include an egress modeling system that determines egress strategies to be used to guide people out of a building during a fire, signaling devices that are configured to be positioned at the plurality of locations in the building, an output device configured to output signaling instructions to a user, a biometric sensor configured to measure biometric characteristics of the user, and an egress assessment computing system. The egress modeling system can be configured to receive a building layout for the building and user timing information for movement throughout the building, simulate, based on the building layout and user timing information, fire scenarios in the building, perform, based on the simulated fire scenarios, predictive analytics to determine an ability of a user to safely egress from a plurality of locations in the building, generate, based on the simulated fire scenarios and predictive analytics, egress strategies specific to each of the plurality of locations in the building, each of the egress strategies including multiple predetermined egress pathways for a location and corresponding logic for selecting among the multiple predetermined egress pathways based on current fire conditions within the building, and generate, based on the modeled egress strategies, signaling instructions that are specific to each of the egress strategies, each of the signaling instructions being configured to output instructions to guide a user to take a corresponding egress pathway to exit the building. The signaling devices can each include a wireless communication interface configured (i) to receive an egress strategy and particular signaling instructions that are specific for the signaling device generated by the egress modeling system and (ii) to receive information identifying current fire conditions in the building. The particular egress strategy can include a plurality of predetermined egress pathways and particular logic of selecting among the plurality of predetermined egress pathways. The signaling devices can each include a processor configured to use the particular egress strategy to select a specific egress pathway from among the plurality of predetermined egress pathways based on the particular logic and the current fire conditions in the building, an environment sensor configured to sense real-time environmental conditions at the plurality of locations in the building, and an output system configured to visually or audibly output instructions to exit the building using the selected egress pathway using particular signaling instructions corresponding to the selected egress pathway. The egress assessment computing system can perform operations that include receiving, from the signaling devices, the environmental conditions, receiving, from the biometric sensor, the biometric characteristics of the user, determining environmental conditions based on the received environmental conditions, determining a stress level of the user based on the biometric characteristics, and sending, to at least one of the output device and the signaling devices, signaling instructions based on determining at least one of the environmental conditions and the stress level of the user being below a predetermined threshold value. Sending to at least one of the output device and the signaling devices, signaling instructions can further include selecting signaling instructions having step-by-step guidance to the user based on the stress level of the user exceeding the predetermined threshold value, and selecting signaling instructions having minimal guidance to the user based on the stress level of the user being equal to or greater than the predetermined threshold value.

In some implementations, the egress assessment computing system can perform operations that include generating a mental model of the user based on the biometric characteristics of the user. The mental model can indicate at least one of the stress level of the user, how long it took the user to make a decision and act without guidance, or what guidance the user received. Moreover, the environmental conditions can include a pathway obstruction by a fire, an increased temperature of the fire, or smoke at a location of the plurality of locations in the building where the user is located The details of one or more implementations are depicted in the associated drawings and the description thereof below. Certain implementations may provide one or more advantages. For example, training simulation models can better prepare building occupants, first responders, and other essential stakeholders to cope with real-time emergencies. Building occupants can be uncomfortable with an emergency response plan that requires them to stay-in-place. Instead of following that plan, in a real-time emergency, occupants may irrationally decide to try and escape the high-rise building, which can compromise their safety. The training simulation models can help occupants become comfortable with stay-in-place plans so that the stress of the emergency does not cause them to make irrational decisions. Experiencing different emergency scenarios with XR prepares the stakeholders to handle stress, anxiety, and making decisions. The training simulation models can also prepare occupants, first responders, and other stakeholders to better work with and be familiar with the disclosed technology during a real-time emergency. For example, during a fire, an occupant who has undergone training simulation models may not feel uncomfortable or uncertain in using or trusting guidance instructions provided to the occupant by the disclosed technology. Moreover, the disclosed technology includes generating mental models that model a trainee's decision-making process and stress levels during simulated training models. Using the mental models, the disclosed technology can determine what additional training the trainee needs to reduce their stress levels and/or what type of guidance would better assist that trainee during a real-time emergency.

Egress strategies can be automatically generated and used in an emergency, such as a fire, even if occupants have not previously generated or addressed such egress strategies. These egress strategies can be generated by taking into consideration information pertaining to the occupants of a building, such as how quickly each of the occupants can egress from any particular room in the building, information about the building itself, such as a layout and/or floorplan, and other information, such as how fast a fire in any particular part of the building can grow, change in temperature, and spread to other parts of the building. Thus, egress strategies can be modeled using fire scenario simulations, predictive analytics, and some artificial intelligence in order to determine a plurality of the most optimal, safe, and non-chaotic pathways/routes out of the building during an emergency.

Dynamic egress guidance can also be provided that is based on real-time situational information about fire conditions within the building. Real-time information about a current fire condition can be exchanged between signaling devices located within the building such that each signaling device can evaluate a list of predicted egress strategies, select an optimal egress strategy, and instruct users in the building about which directions to take to safely exit the building before it is entirely engulfed in flames. The egress guidance can be audio and/or visual output, depending on the particular needs of any of the occupants in the building and/or depending on what devices and/or technology are installed in the building.

Moreover, the disclosed technology provides for outputting guidance to stakeholders in situations where their own decision-making is compromised by unexpected environmental behaviors. For example, a first responder can be deciding on their own about how they are going to save an occupant, but real-time conditions about the fire, such as excessive smoke, can prevent the first responder from safely going through with their decision. Thus, the technology disclosed herein can automatically and seamlessly kick in to provide guidance to the first responder that redirects the first responder away from the unexpected environmental behaviors. Guidance can automatically and seamlessly turn on and off such that the first responder can still make their own decisions.

The features described herein can advantageously aid occupants in escaping the building during an emergency in a non-chaotic, productive fashion. During a fire, an occupant's thought process can be chaotic, but since the disclosed technology provides real-time guidance that is based in large on pre-analyzed scenarios, chaotic thoughts and irrational determinations by the occupant(s) can be avoided. Consequently, the described features ensure the occupants' safety and a non-chaotic, safe exit from the burning building. Moreover, the disclosed implementations can optimally provide for none or only one egress course correction in guiding occupants to safety during a fire.

The disclosed technology and techniques can further provide advantages in data analytics and improvement of the overall technology and/or techniques. Data collected and used by the disclosed technology can be beneficial to improve a design and techniques of the disclosed technology. The collected data can also be beneficial to various stakeholders, including but not limited to firefighters, fire safety engineers, builders, the insurance industry, and municipalities. For example, firefighters can use the collected data to improve their training to better save people from fires, prevent fires from spreading to nearby buildings, and/or save the firefighters' lives. Other features, objects, and advantages of the technology described in this document will be apparent from the description and the drawings, and from the claims.

BRIEF DESCRIPTION OF THE DRAWINGS

FIGS. 7A-C are conceptual diagrams of a building floor map with predicted egress strategies that are used to instruct occupants in the building about how to safely exit during an emergency.

Like reference symbols in the various drawings indicate like elements.

DETAILED DESCRIPTION

Figure 1:
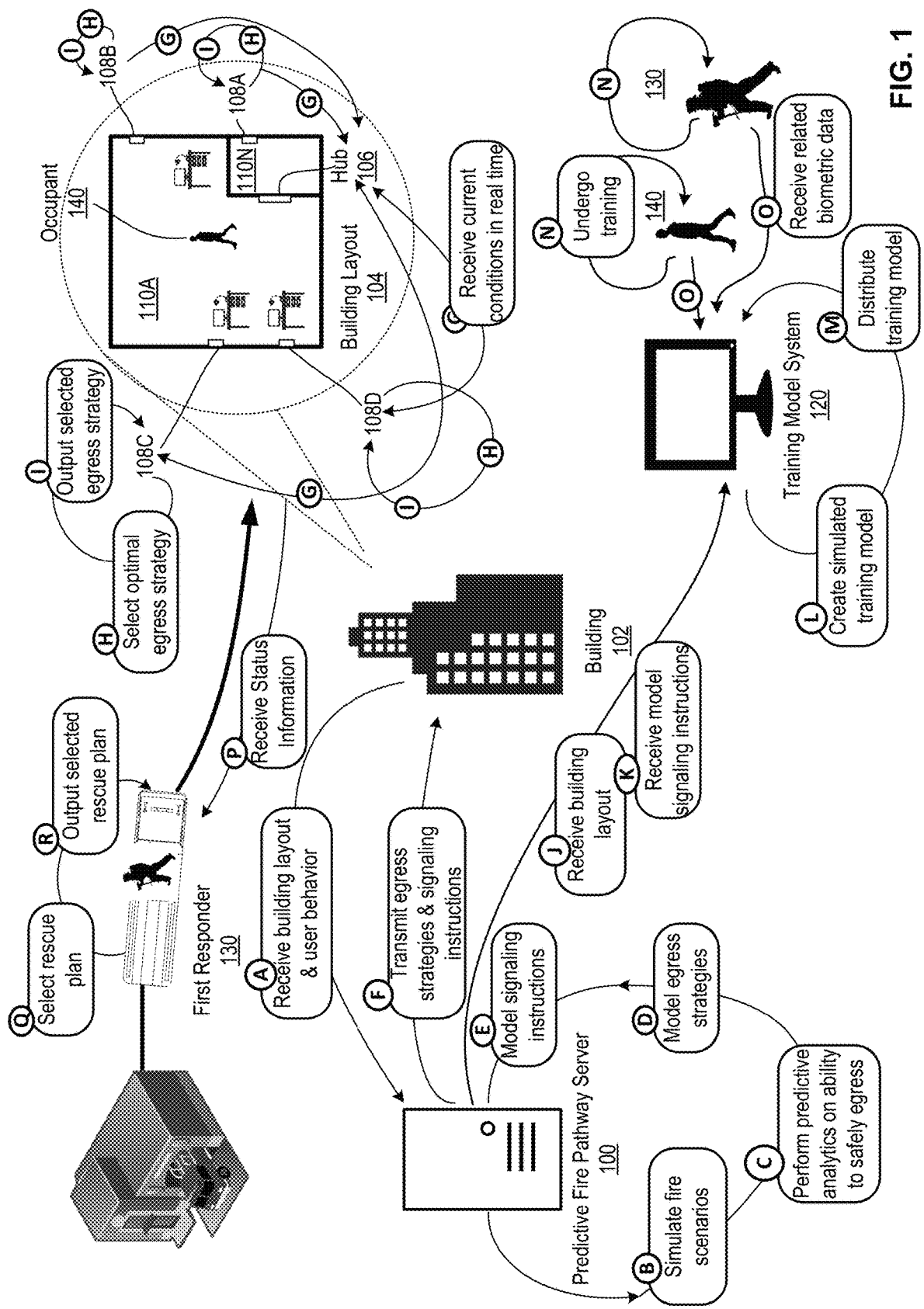
FIG. 1 is a conceptual diagram of an example system for training, predicting safe egress strategies out of a building, and selecting an optimal egress strategy during an emergency.

The disclosed system enables the training and safe egress of occupants in a building in the event of an emergency, such as a fire. The disclosed system can apply to residential and non-residential buildings, including but not limited to high-rise buildings, schools, and office and retail buildings. In comparison to residential homes, high-rise buildings typically only have one or two possible egress pathways. Limited ability to escape from a high-rise during an emergency can cause high levels of stress and chaos amongst building occupants. Therefore, enhanced safety training models, as disclosed throughout this disclosure, can aid occupants and other related stakeholders, such as first responders and building security, to more calmly and comfortably respond to an emergency and safely egress during an emergency. Predictive analytics are incorporated into this system to enhance the training models and guide occupants to safely egress without creating false starts and unproductive, chaotic scrambling on the way to safety. One of the goals of the disclosed system is to assist occupants and other stakeholders in minimizing stress and chaos in the event that an emergency occurs in a high-rise building, where the only possible egress pathways may be through an elevator, stairwell, or high-rise window. In some high rises, escape through a window may not be possible, so the disclosed technology can assist occupants and other stakeholders in becoming comfortable and familiar with egress strategies that include staying in place, escaping through a stairwell, or taking an occupant evacuation elevator (OEE).

The disclosed system further enables simulation of fire scenarios, predicting occupants' ability to escape the simulated fire scenarios, and modeling possible egress strategies then selecting an optimal egress strategy in real-time based on current conditions of a fire in the building. These are critical steps to minimize the need for any course corrections during the egress process. As a result, occupants can exit as quickly and calmly as possible before all possible ways to evacuate the building are eliminated. One of the goals of the disclosed system is to ensure that none or only one course correction may be necessary to guide occupants to safety.

In high-rise buildings, occupants may have 10 to 15 minutes before first responders can get to them and assist in egressing. During this time, a fire can spread throughout a floor in the high-rise building, thereby eliminating possible exits via an elevator, emergency stairwell, and/or high-rise window. A goal of the disclosed system is to train occupants about how to safely egress during those 10 to 15 minutes without experiencing high levels of stress or chaos. Another goal of the disclosed system is to train first responders and other essential stakeholders about how to quickly, safely, and calmly enter the affected floor of the high-rise building. Yet another goal of the disclosed system is to use predictive analytics and/or AI to guide occupants and other stakeholders to safely egress during an emergency with minimal egress pathway correction.

Similarly, residential homes and/or smaller buildings are more likely to reach full flame engulfment in less time than high-rise buildings, based on the materials used to build the homes and smaller buildings. For example, it may take a new residential construction only 3½ minutes to reach full flame engulfment. Given this time frame from when a fire starts to the point that the flames engulf the entire structure, the disclosed system can train occupants about how to quickly, safely, and calmly exit the building such that during an emergency, egress pathway corrections are minimized and occupants are comfortable and/or familiar with a selected egress pathway. This is in part made possible by the predictive analytics incorporated into the system to determine how occupants respond to simulated fire training models and guide occupants to safe egress without creating false starts and unproductive, chaotic scrambling on the way to safety.

In some implementations, the disclosed system can include wearable devices (i.e., biometric sensors) and/or other suitable devices (i.e., sensors set up adjacent or around trainees) to analyze how trainees respond to simulated fire training models. For example, biometric data can be collected with the wearable devices and used by the disclosed system to improve and/or generate simulated fire training models. Wearable devices can also be used to assist occupants in exiting the building during a real-time emergency. For example, occupants experiencing sight or hearing deficiencies can wear wearable devices to help those occupants safely egress from the building during an emergency when they typically cannot hear and/or see the audio/visual outputs (i.e. directions out of the building) described throughout this disclosure. Non-wearable devices or other suitable devices can be similarly used to collect biometric data to improve and/or generate simulated fire training models.

Now turning to the figures, FIG. 1 is a conceptual diagram of an example system for training, predicting safe egress strategies out of a building, and selecting an optimal egress strategy during an emergency. The system includes a predictive fire pathway server 100, a training model system 120, a building 102, first responder(s) 130, and occupant(s) 140. The building 102 has a building layout 104, which can include rooms 110A-N (i.e., kitchen, cubicle space, private office, bathrooms, etc.). The building layout 104 further includes one or more fire-sensed or other fire-related elements, including but not limited to fire and/or smoke detectors, occupant sensors, guidance devices, emergency equipment (i.e., fire escape, inflatable ladder, ladder, etc.), and other building equipment such as occupant evacuation elevators (OEEs) and/or sprinkler systems. In some implementations, the guidance devices can be integrated into one or more signaling devices 108A-D and a hub 106. In other implementations, the guidance devices can be separate devices in communication with the one or more signaling devices 108A-D, the hub 106, and/or computer systems described throughout this disclosure. One or more fire-related elements disclosed herein can be incorporated into a single device/system, multiple devices/systems, and/or in communication via a network with each other. The building layout 104 can be communicated/transmitted to the server 100 such that the server 100 can use the layout 104 in simulating fire scenarios (i.e., step B). The building layout can also be communicated to a device of the first responder(s) 130 along with status information (i.e., step P).

In the building 102, the one or more signaling devices 108A-D and the hub 106 are installed. The hub 106 can be a central control system that receives and communicates current conditions in real-time with the signaling devices 108A-D. In some implementations, the hub 106 can act like the signaling devices 108A-D by sensing real-time conditions of a fire in the building 102 and/or selecting an optimal egress strategy and outputting instructions to the occupant(s) 140 about how to safely egress from the building 102. For example, the hub 106 can act as a signaling device in a room where there are no other installed signaling devices. The hub 106 can be located in a hallway/elevator bank of the building 102 and thus can act as a signaling device for that hallway/elevator bank. The hub 106 can also receive indications about a fire from the previously discussed fire-related sensing elements (i.e., fire detectors, sprinkler system, etc.).

In some implementations, the hub 106 can be an emergency control center. The hub 106 can also be remote from the building 102. For example, the hub 106 can be a mobile device configured to receive real-time conditions of a fire in the building 102. The hub 106 can receive information about real-time conditions on every floor of the building 102, thereby providing a user of the hub 106 with access to information regarding the entire building 102. The user of the hub 106 can then monitor real-time conditions for the entire building 102. The user can oversee guidance provided to occupants on different floors of the building 102 and also how occupants and/or first responders respond to the real-time conditions. The user can be an incident commander in charge of monitoring emergencies in various buildings. In other implementations, the user can be a security officer or building manager for a particular building, such as the building 102.

Preferably, each of the signaling devices 108A-D can be installed in each room in the building 102, as depicted in the building layout 104. The signaling devices 108A-D are configured to wirelessly communicate with each other in real-time via a communication such as WIFI, BLUETOOTH, or any other form of wireless connectivity. In some implementations the signaling devices 108A-D can communicate through a wired connection. This can be beneficial during emergencies in which a wireless connection (i.e., WIFI) is down and/or damaged by conditions of the emergency (i.e., a fire spreads and engulfs a router sending WIFI signals throughout the building 102).

As mentioned, the signaling devices 108A-D can communicate real-time, current information about conditions of a fire in the building 102. The signaling devices 108A-D can also be in communication with one or more of the previously described fire-related elements. Current conditions can include a temperature of the fire, a temperature of a room that a signaling device is located in, and whether the fire spread to the room. In some implementations, the signaling devices 108A-D can include a monitor and/or one or more cameras to observe current conditions of the rooms that each of the signaling devices 108A-D are located in. Consequently, based on the captured footage, the signaling devices 108A-D can determine whether the fire started and/or spread to any of the rooms in the building 102 and/or on a particular floor of the building 102. In other implementations, the signaling devices 108A-D can be connected to one or more cameras that are installed throughout the building 102. The one or more cameras can be wirelessly communicating with the signaling devices 108A-D. Alternatively, the cameras can communicate with the signaling devices 108A-D through a wired communication. A setup involving the use of cameras that are already installed and/or separately installed in the building 102 can be beneficial where the described system (the signaling devices 108A-D and the hub 106) is retrofitted to an existing building.

Preferably, the signaling devices 108A-D can include temperature sensors (i.e., thermocouple heat sensors) to read temperature values in each of the rooms in real-time. In some implementations, the signaling devices 108A-D can communicate with sensors that are installed in the building 102. These sensors can be installed around windows, doors, and/or at near the ceiling. The sensors can also be installed prior to installation of the described system (the signaling devices 108A-D and the hub 106), wherein the described system is retrofitted to the building 102. In yet other implementations, the signaling devices 108A-D can have integrated temperature sensors and still communicate with additional sensors that are installed throughout the building 102. This setup can be beneficial for redundancy and ensuring that accurate temperature readings are acquired and used by the signaling devices 108A-D in determining what egress strategy to select during an emergency. Current temperature information is beneficial for the signaling devices 108A-D to adopt the optimal egress strategy from the building 102. For example, if current temperature information indicates that the fire is in a private office farthest from an elevator bank in the building layout 104, then a signaling device located at the elevator bank can select an egress strategy that will direct occupants towards the elevator bank and away from the private office.

The signaling devices 108A-D can also be configured to output instructions to the occupant(s) 140 for safely egressing from the building 102. For example, the signaling devices 108A-D can include speakers that are integrated into the devices so that the devices can provide an audio output of instructions. The signaling devices 108A-D can also include integrated lights to display a visual output of instructions to egress from an office space in the building 102. In other implementations, the signaling devices 108A-D can communicate with one or more speakers and/or lights that are installed in the building 102 through a wired and/or wireless communication. In yet other implementations, the signaling devices 108A-D can communicate with wearable devices and other devices that are used by the occupant(s) experiencing a disability (i.e. blindness, deafness).

Moreover, the hub 106 can include a monitor for displaying potential fire scenarios to building occupant(s) 140. For example, building occupant(s) 140 can view egress routes at any time, as desired, via the hub 106. The hub 106 can also be connected to a device within the building 102 (i.e., a TV) and serve as an input for changes to any occupant and/or building design information. For example, if a business client is visiting an office in the building 102, the building occupant(s) 140 can update the described system about the business client's presence via the hub 106. That way, the business client can be considered by the individual signaling devices 108A-D in the event of an emergency wherein the signaling devices 108A-D must select an egress strategy and output egress instructions to all occupants within the building 102. Information about occupant(s) 140 that can be updated and/or changed includes age (i.e., birthday just occurred), agility level (i.e., an occupant no longer has crutches or a cast on his leg, an elder relative just moved in and is in a wheelchair, etc.), and whether a building occupant is on vacation/not present in the building 102.

Prior to customization and installation of the signaling devices 108A-D and the hub 106, the predictive fire pathway server 100 can explore different fire scenarios, identify vulnerabilities that compromise safety in the building 102, suggest remediation steps and processes for the identified vulnerabilities, predetermine most effective egress routes for potential fire scenarios, and establish a design and programming of the signaling devices 108A-D and the hub 106 to then be installed in the building 102. The predictive fire pathway server 100 can make such determinations for each floor of the building 102. In other implementations, the server 100 can make such determinations for each similar building floor layout 104. For example, if floors 1-10 in a high-rise all have identical layouts, the server 100 can generate egress routes for those floors while generating different egress routes for floors 11-20, which have a different layout than floors 1-10. This can be more efficient than generating individualized egress routes for every floor in a high-rise building. When the server simulates fire scenarios and identifies potential egress strategies (i.e., steps B-C), the server 100 can use information including transit distances between each room/office space and each exit point in the building 102, each occupant's mobile abilities (i.e., an occupant in a wheelchair is slower than a teen who is healthy and active), and other specifics related to the building layout 104, potential paths that a fire can spread throughout the building 102, how long it would take the fire to spread, etc. In some implementations, the server 100 can generate egress routes for the building 102 and then refine those routes per each floor's layout, based at least in part on each occupant's mobile abilities and other occupant information.

Establishing safe egress strategies requires a comprehensive prior evaluation and analysis of the building 102 with respect to its layout (i.e., the building layout 104 and/or floorplan for each floor in the building 102) and structure (i.e., whether the building 102 is a high-rise, whether the building 102 has fire escapes at windows, whether windows can be opened, whether elevators continue to work during an emergency, etc.), age and physical capabilities of its occupants, and other factors. Performing such evaluation and analytics before real-time execution can be beneficial to determine all potential scenarios of how a fire would pan out and how all occupants would react. Consequently, in real-time, the optimal egress strategy can be selected to ensure that all occupants safely exit the house 102 without chaos and without having to correct/change a selection of the optimal egress strategy.

The server 100 can also be configured to guide occupants to relocate other occupants with disabilities (i.e., elderly in a wheelchair) beforehand to a place in the building 102 that would enable safe and non-chaotic egress in the event of a fire. The server 100 can make such a determination and suggestions based on simulating fire scenarios and determining how each occupant in the building 102 would react and egress from the building 102 (i.e., steps B-C). In some implementations, the server 100 can be configured to guide building managers about making one or more changes to the building 102 itself that would ensure safety and proper egress for all occupants. For example, the server 100 may determine that a door should be installed in a doorway that separates two zones in the building 102 (i.e., separating an elevator bank from a general office space) in order to create a firewall effect that provides for additional egress time from other parts of the building 102. In another example, the server 100 can determine that a fuel load in one zone of the building 102 (i.e., a shared kitchen, break room, garbage chute, etc.), for a given fire scenario, would prohibit safe egress for the occupants. Consequently, the server 100 can determine that that particular zone should be modified in some way to reduce the fuel load. For example, appliances and other potential sources of fire initiation can be assessed, such as garbage chutes and cladding. The server 100 can use predictive analytics in order to assess and determine what uses and/or timeframe can lead to appliances or other items in the building 102 starting a fire. The server 100's determinations can be beneficial to guide high-rise builders in constructing better building designs that reduce egress distances to exits and/or ensure increased occupant safety during an emergency.

Still referring to FIG. 1, the server 100 can receive building layout (i.e. the building layout 104, distances/measurements between different rooms/spaces on each floor in the building 102 and exit points, etc.) and user information (i.e., age, agility, and disabilities of each of the occupants, etc.) from the building 102 in step A. In this step, a building manager and/or builder can upload this information about the building 102 and its occupants directly to the server 100. In other implementations, this information can be uploaded in real-time to the server 100 by an occupant(s) in the building 102 and/or by updating/inputting/adding into the hub 106 information about the occupants or other building design information. Using this information, the server 100 can simulate fire scenarios in step B then perform predictive analytics on the ability of all of the occupants to safely egress in any of those fire scenarios in step C.

By simulating fire scenarios in step B, the server 100 can flush out potential safety vulnerabilities and determine appropriate egress strategies (i.e., routes, paths) for each of the simulated scenarios. The server 100 can simulate different fire scenarios to determine how quickly a fire would spread to other areas, spaces, and/or floors in the building 102 and how the spread of the fire would impact different exit points throughout the building 102. The server 100 can also simulate different scenarios to determine whether one or more floors above and/or below a floor having a fire would also need to be safely evacuated. The server 100 can use information including temperatures of a fire when it starts, when it's at a peak, and when it's on a decline to simulate fire scenarios in the building 102. The server 100 can also use information about the building 102 to simulate fire scenarios, including when the building 102 was built, what materials were used to build the building 102, the building layout 104, whether windows can be opened, whether emergency stairwells and fire escapes were installed, and whether elevators can operate during an emergency. Moreover, the server 100 can assess potential vulnerabilities in the building 102 (i.e., old appliances that are likely to start a fire) and detect faults in objects and/or activities within the building 102 that can initiate a fire.

Then, using specialized predictive analytics and elements of artificial intelligence, the server 100 can determine how well occupants can egress using predicted egress strategies in any of the simulated fire scenarios (step C). In some implementations, the predictive analytics utilizes a specialized time temperature equation that is mathematically deterministic, but can also incorporate stochastic analysis for added rigor and safety. Moreover, elements of AI can be incorporated with respect to predictive analytics in order to broaden its scope and ensure that it accommodates emerging technology and advances in modes of analysis. The power of predictive analytics lies in its ability to predict the rate of rise of temperature in a space that contains a fire, starting from fire initiation to maximum growth before ultimate decline. As its primary goal, the methodology utilized by the server 100 can predict times to maximum escape temperature and flashover. These parameters, coupled with information on building layout (i.e., building layout 104) versus the mobility and general physical and mental capabilities of occupants in the building 102, establish the viability of predicted egress strategies and routes.

The basic defining time-temperature equation for the example predictive analytics methodology utilized by the server 100 is as follows, in which its application is in the space with fire:

$$T = T_{max}[t/t_{max} \exp(1 - t/t_{max})]^C$$

In which T is the computed temperature above initial room temperature at time, t, $T_{max}$ is the maximum expected temperature in a room with fire, $t_{max}$ is the expected time when $T_{max}$ is reached, and C is shape factor for the time-temperature curve. For example, in most residential home fires, $T_{max}$ is about 1100° F. and $t_{max}$ is about 3½ minutes in a typical home fire. The values of $T_{max}$ and $t_{max}$ can be modified for known characteristics and conditions in a home as determined by the server 100. The factor C, which determines the critical shape of the time-temperature curve, is determined as follows:

$$C=[\ln T_1/T_{max}]/[\ln t_1/t_{max}+1-t_1/t_{max}]$$

In which $T_1$ is the temperature above initial room temperature at time, $t_1$, and all other variables are as previously defined. In the simulation performed by the server 100, $T_1$ is estimated from a rationally-based audit methodology that includes extremum analysis and critical ranges of possibility. At the signaling devices 108A-D, $T_1$ is determined from one or more thermocouple outputs during an actual fire via a sampling process, a vital distinction. The time, $t_1$, is chosen to be 15 seconds, for reasons elaborated later. In a fire, temperature is sampled every second or quicker, with a running 10-second time-averaging window applied to the process. That is, to determine $T_1$ at $t_1=15$ seconds, temperature data that is sampled starting at 10 seconds and ending at 20 seconds are averaged to calculate the value for $T_1$. Therefore, $t_1=15$ resides at the midpoint of the 10-second time-averaging window in determining $T_1$. The averaging process is critical to smoothing the data to yield a more accurate representation of $T_1$, because a fire fluctuates, hence so does temperature. Choosing a 10-second time-averaging window in determining $T_1$ is arbitrary, but is based on engineering experience and judgement in collecting temperature data in a fire setting. Also, a larger time-averaging window can reduce the available egress time.

A fire typically starts on a limited, localized scale, then experiences a sudden "pulse" growth for a period of time before reaching flashover, followed by final growth at a continuously reducing rate until it reaches its maximum level of intensity. After reaching its maximum, a fire goes into a declining stage as its fuel is depleted. The time at which temperature becomes impassable at a particular egress location, followed later by the temperature for when flashover occurs, are predicted by the server 100 as follows.

Figure 9:
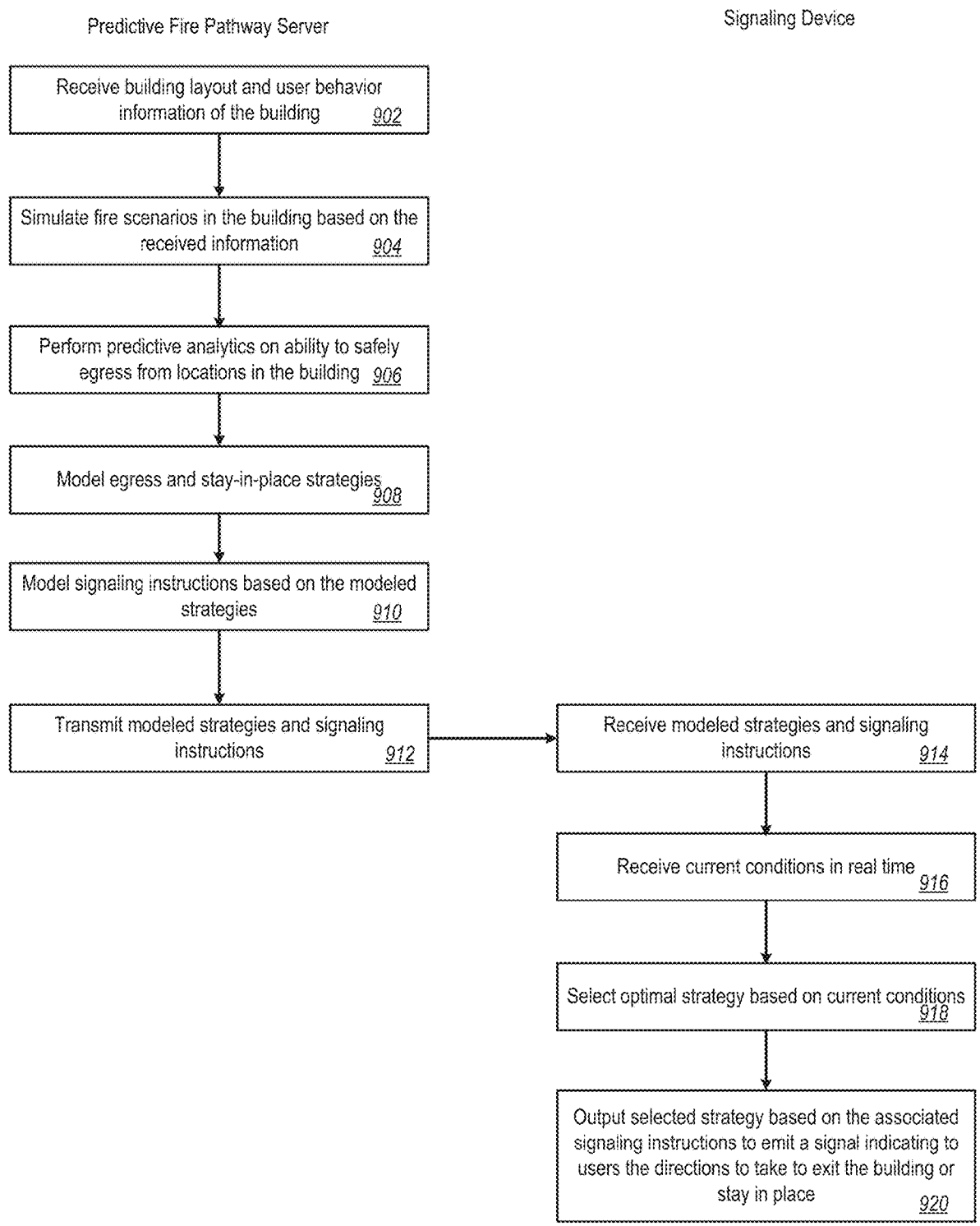
FIG. 9 depicts a flowchart of an example technique for predicting egress strategies and selecting the optimal egress strategy during an emergency.

The precise time to maximum escape temperature, chosen to be 300° F. (149° C.) for dry conditions, and the specific shape of the curve depend on $t_{max}$, $T_{max}$, and $T_1$ at time $t_1$. As stated above, and repeated now for emphasis, the value of $T_1$ for a chosen time, $t_1$, which is 15 seconds in this example, is estimated by the server 100 when simulating fire scenarios in step B, as stated above, but measured directly in an actual fire in the signaling devices 108A-D. Using the equations from above, FIG. 9 depicts four time-temperature curves as a function of time for various values of $T_1$, assuming the values of $T_{max}$ and $t_{max}$ cited above. In FIG. 9, curves labeled 1,2,3, and 4 correspond to $T_1$ values of 0.1° F., 2° F., 5° F., and 15° F., respectively (0.06° C., 1.1° C., 2.8° C., and 8.3° C.). Time, $t_1$, equals 15 seconds in all cases. The values for $T_1$ were chosen arbitrarily to elucidate the potential shapes of the time temperature curve and to assess the range of potential egress times. All four curves are "sigmoid" in basic shape, accurately representing the behavior of a real fire, but differ importantly in the information each provides on precise temperature history. If $T_1=0.1°$ F. (0.06° C.) after 15 seconds, the fire can be considered embryonic, while if $T_1=15°$ F. (8.3° C.) in the same timeframe, the fire is still in a relative infancy but not embryonic. The times in the respective curves at which the temperature in the room reaches the impassible point, 300° F. (149° C.) for dry conditions, are 70, 52, 45, and 35 seconds, respectively, in which $t_1=15$ seconds plus one half of the 10-second time-averaging window, totaling 20 seconds, have been subtracted.

Choosing $t_1=15$ seconds reasonably assures that enough temperature measurements have been undertaken with the thermocouples to determine accurate results with the predictive analytics methodology in a real fire. There is a feature in the methodology, as previously mentioned, that allows for one course correction in egress early in the process after a fire is detected in real-time. Regardless, the basic process is as follows. During the 20-second sampling time in determining $T_1$ in a real fire, the signaling devices 108A-D can be configured to alert occupants about the fire, providing initial guidance, and allowing them to prepare for egress. In some implementations, $t_1$ can be longer, i.e., 25-30 seconds, but given the typical 3½ minute time in which flames fully encompass a home, 15 seconds can be more prudent. In the final analysis, as performed by the signaling devices 108A-D, occupants ought to not be guided quickly to a point on an escape path that may become engulfed with flames by the time they arrive. The formula described herein can be applied and adapted to emergencies in residential homes, small commercial buildings, large commercial buildings, and high rise buildings.

In the server 100 and the signaling devices 108A-D, the deterministic aspects of the above equations are complemented by stochastic processes and artificial intelligence (AI) in the form of neural networks and genetic algorithms, for example, to make the server 100 and signaling devices 108A-D more robust and resilient. Factors that are included in the server 100 and signaling devices 108A-D through stochastics and AI include such things as determining the possibility of (a) window blow out that can amplify fire flow paths, and (b) the effects of fuels types and fire loads on fire dynamics in various places in a home. The estimation of $T_{max}$ and $t_{max}$, and related parameters, are affected by these various factors.

To summarize the basic predictive analytics methodology described herein, when a fire ignites an initial sampling period of $t_1+5=20$ seconds occurs in which the installed signaling devices 108A-D can gather temperature data with the various thermocouples located strategically throughout the building 102. Once $T_1$ is determined, the second equation depicted above can be used to calculate C. Then the first equation depicted above can be used to predict the time that temperature will rise to its maximum allowable escape level, and the time at which flashover will occur. Escape and flashover times, with $t_1+5=20$ seconds subtracted, coupled with predetermined exit transit distances and estimated egress speeds for each building occupant, as determined by the server 100, considering instances of required assistance by able-bodied persons, allow the installed signaling devices 108A-D to provide proper and effective guidance for escape to safety.

The predictive analytics described throughout includes a feature for one course correction in a fire in the building 102, as previously discussed. After the initial sampling period of 20 seconds (e.g., $t_1+5$, which can be different based on whether the building 102 is a residential home, small commercial building, large commercial building, or high rise building), the signaling devices 108A-D can continue to sample temperatures from the thermocouples in the room(s) with fire as well as those distributed in various rooms throughout the building 102. The hub 106 and/or the signaling devices 108A-D can determine at various points in time to what extent the initial predictions in temperature rise hold and whether they were low or high. If high, the initial assessment of allowable egress time holds. If low beyond a certain tolerance level, occupants can be instructed to return to their starting point and to exit from an egress window (i.e., a window that opens and that has a fire escape). This course correction can be valid for a short time after the initial sampling period, i.e., 15-30 seconds beyond the initial 20 seconds, depending on occupant mobility, egress distances, and other logistical factors. In the final analysis, conservative judgments can be made, by the signaling devices 108A-D, on egress guidance.

As a simple example, using predictive assessments, the server 100 can determine that it would take a particular occupant 30 seconds to get out from a private office to an elevator bank at the opposite end of the floor. The server 100 can also determine that the fire will spread to the elevator bank or anywhere along the occupant's escape route in less than 30 seconds. So, the server 100 can determine alternative egress strategies that can safely lead the occupant out of the building 102 without coming into contact with the fire. In an example scenario where the fire starts or is located in the kitchen/break room, the server 100 can determine that the fire can reach the elevator bank in 1 minute. Based on this information, the server 100 can determine that the occupant can safely exit through the elevator bank because it would take the occupant 30 seconds to do so. Thus, this exit route can become one of the modeled egress strategies (i.e., step D). The goal of the server 100 is to create and predict optimal egress strategies that direct occupants away from the fire and out of the building 102 in the fastest and safest way possible. The server 100 is configured to predetermine egress pathways through the building 102 and predetermine contingencies should any of the predicted egress pathways not be the most optimal one during an emergency in real-time. Importantly, most high-rise buildings have a limited number of possible egress routes. For example, elevators may be inoperable during a fire and occupants may only escape through a stairwell. In other examples, the only possible escape route can be through a window having a fire escape or some other emergency device (i.e., inflatable ladder, rope, etc.). Therefore, another goal of the server 100 is to create and predict optimal egress strategies so that an egress course correction does not have to be implemented during a real-time emergency. Implementing a course correction during an emergency may cause increased chaos, stress, and/or reduce occupant safety.

In some implementations, the use of predictive analytics by the server 100 does not necessarily entail artificial intelligence (AI). Rather, it can entail deterministic mathematics, conventional and/or clever applications of statistics, and/or AI. Moreover, AI itself can entail statistics and/or stochastics in its inner workings. In the example depicted throughout this disclosure, a deterministic mathematical approach is employed by the server 100 in simulating fire scenarios (i.e., step B). However, in other implementations, the disclosed determinations of fire and/or temperature growth can be performed using artificial intelligence or artificial intelligence in combination with various forms of predictive analytics.

Next, still referring to FIG. 1, in step D, the server 100 can model egress strategies for each of the rooms/office spaces in the building 102 based on the simulations and predictive analytics of steps B-C. The server 100 can perform if/else true/false logic to determine a list of key egress strategies for each of the rooms/office spaces in the building 102. For example, the server 100 can determine that if fire exists in room A in a back of an office space of the building 102, then exit strategy 1 should be selected as an optimal exit strategy for exiting the office space via an elevator bank in a front of the office space. If, however, the elevator shuts down during an emergency, then exit strategy 2 should be selected for exiting via an emergency stairwell in the front of the office space. As another example, if the fire is on one floor of the building 102 and it can spread to another floor directly above/below, then the server can determine at least one exit strategy as the optimal exit strategy for exiting the floor where the fire will spread. Then, in real-time execution, a signaling device on a floor where the fire starts and a floor where the fire will spread can select any egress strategy from the list of key egress strategies made by the server 100 but would optimally select the egress strategy that the server 100 modeled as the optimal exit strategy in the particular scenario.

Once the list of key egress strategies is created, the server 100 can model signaling instructions that are associated with each of the key egress strategies in the list in step E. The server 100 can model instructions that can be visually outputted and/or outputted as audio. For example, based on occupant preference, instructions for exiting the building 102 along a particular egress strategy can be outputted using lights (i.e. LED lights). The lights can be displayed, from the signaling devices 108A-D and/or in any of the rooms/office spaces in the building 102, depicting arrows or some other illumination that would indicate the appropriate path to take out of the building 102. In another implementation, the lights can be in the form of LED strips attached on top of a molding of one or more windows and/or doors in each of the rooms/office spaces in the building 102. The LED strips can become illuminated to direct occupants safely out of the building 102 upon instruction from a signaling device and/or the hub 106 during an emergency. The LED strips can communicate wirelessly or through a wired connection with the signaling devices 108A-D and the hub 106. In yet another implementation, instructions to exit the building 102 can be outputted using audio, in which the signaling devices 108A-D and/or external speakers installed in the building 102 dictate instructions to occupants about exiting the building 102. In some implementations, audio output can come from a speaker embedded in one or more outlets throughout the building 102.

Once the signaling instructions are modeled, the server 100 can transmit the list of key egress strategies and their associated signaling instructions to the building 102 in step F. The signaling devices 108A-D on each floor of the building 102 can preload the lists of key egress strategies, wherein the list includes all possible strategies to exit a particular room/space that each of the signaling devices 108A-D is located in. As mentioned, these predicted egress strategies can foreshadow a time it would take any particular occupant to exit the building 102 and a time it would take for the fire to spread to any area of the building 102, thereby restricting or closing off any exit points on each floor of the building 102.

Additionally, the server 100 can transmit the building layout 104 to the training model system 120 in step J. In some implementations, the training model system 120 can receive the building layout 104 directly from the building 102, as described above. In yet other implementations, the system 120 can receive the building layout 104 at a same time that the server 100 receives the layout 104. The system 120 can receive the layout 104 before the server 100 receives the layout 104. Moreover, in some implementations, the system 120 can perform steps J-O before the server 100 performs steps B-F and/or steps G-I. In yet other implementations, the system 120 can perform steps J-O at a same time as the server 100 performs steps B-F.

Still referring to the training model system 120 in FIG. 1, the server 100 can also transmit the signaling instructions that were modeled in step E (step K). Receiving the modeled signaling instructions is beneficial for the system 120 to create more advanced training models. The simulated training models can incorporate the modeled signaling instructions such that trainees can test the signaling instructions during a simulated fire scenario. In step L, the system 120 can create (i.e., generate) a simulated training model based at least in part on the building layout 104 received in step J as well as the modeled signaling instructions received in step K. The training model can be at least one of a 3D, AR, and/or VR representation of a building layout during an emergency, such as a fire. The model can incorporate egress routes and instructions to simulate what occupants would be expected to do during a real emergency. The training model can be specific to a particular building layout. For example, the system 102 can receive the building layout 104 from the building 102 or the server 100 and create a 3D training model of the building layout 104. The simulated training model can then include egress instructions being selected by one or more of the signaling devices 108A-D and being outputted by one or more audio and/or visual output systems throughout the building 102. In other words, the simulated training models can mimic/replicate how each of the systems and devices described throughout this disclosure would function during a real-time emergency, such as a fire. In other implementations, the system 120 can generate a training model that is based on building layouts of one or more buildings. The system 120 can receive building layouts from a plurality of buildings along with modeled signaling instructions from the plurality of buildings and identify commonalities amongst those buildings. Using the identified commonalities, the system 120 can generate a training model that is applicable to all of the buildings. Some of the commonalities can include a floorplan, location of windows and other objects in the building, egress instructions, and/or egress routes.

Once the training model system 120 generates the simulated training model in step L, the system 120 distributes the training model in step M. The model is distributed to essential building stakeholders, such as occupants (i.e., occupant 140), office/building managers and/or security officers, and/or first responders (i.e., first responder 130). Building occupants can use the training model as material in routine safety training. The training model can be beneficial to help occupants understand how they can and/or should egress from a building during an emergency, such as a fire. The training model can also be beneficial to make some occupants more comfortable and/or less stressed when faced with an emergency. The training model can be beneficial to office/building managers and/or security officers in order to train them on how to respond to an emergency in their building. The training model can also be beneficial to first responders because it can train them about where to enter a particular building, where to exit, where to find occupants, and/or what egress routes (i.e., an elevator, a window) will be inaccessible during an emergency.

The training model can be communicated via a wired and/or wireless connection/network, as described throughout this disclosure, to computing devices of the stakeholders. For example, the training model can be downloaded onto a VR headset. As another example, the training model can be downloaded onto a laptop, tablet, and/or phone.

Once the training model is distributed, each of the essential stakeholders can undergo training with the simulated training model (step N). When undergoing training, the stakeholders can wear biometric sensors in order to collect biometric data about the stakeholders. For example, an occupant's heartrate can be recorded during the training. The heartrate data can then be received by the training model system 120 (step O) and used by the system 120 in order to determine whether the occupant was experiencing high levels of stress during the simulated training model. If the occupant's stress level was over a predetermined threshold value, for example, then the system 120 can improve and/or generate a training model to help the occupant and similarly-situated stakeholders in overcoming the higher level of stress. Moreover, the system 120 can use the received biometric data to generate mental models of how trainees respond to an emergency and what decisions the trainees can make/change to avoid experiencing high levels of stress, anxiety, or chaos during a real-time emergency.

As previously mentioned, the egress strategies and signaling instructions can be transmitted from the server 100 to the building 102 (i.e., step F). Each of the signaling devices 108A-D can receive the egress strategies and their associated signaling instructions that relate to exiting the particular room/space that each signaling device 108A-D is located in. For example, if signaling device 108A is located in a kitchen/common break room (i.e., room 110N) of the building 102, then the signaling device 108A will only receive a list of key egress strategies and signaling instructions that relate to exiting the kitchen/common break room during an emergency. Likewise, if signaling device 108B is located in an open office space of the building 102, then that signaling device 108B will only receive the modeled egress strategies and signaling instructions that relate exiting that particular area of the open office space during an emergency.

In some implementations, the hub 106 on each floor of the building 102 can also receive all of the modeled egress strategies and signaling instructions, regardless of which room/office space those strategies pertain to. In yet other implementations, the hub 106 may only receive modeled egress strategies and signaling instructions that relate to the room/space that the hub 106 is located within (i.e., in an elevator bank, bathrooms hallway, etc.). Thus, in some implementations, the hub 106 can function and act like the signaling devices 108A-D.

The server 100 can determine which egress strategies are transmitted to which of the signaling devices 108A-D by assigning values to each of the rooms/spaces per each floor in the building 102. Then, each signaling device 108A-D can be assigned a value that corresponds to the value of each of the rooms/spaces. For example, the kitchen/common break room can be assigned a value of 1 and the signaling device 108A, which is located in the kitchen/common break room, can likewise be assigned a value of 1. Once the server 100 generates a list of key modeled egress strategies for the kitchen/common break room, the server 100 can determine which signaling device 108A-D is located in the kitchen/common break room based on its assigned value and then transmit the list of egress strategies associated with the kitchen/common break room to that signaling device (in the example provided above, the signaling device 108A is located in the kitchen/common break room so the signaling device 108A and the kitchen/common break room have corresponding identification values). For increased efficiency is distributing the list of key modeled egress strategies, on floors having identical layouts/floorplans, the rooms/spaces and signaling devices can receive the same assigned values. For example, if floors 1-10 have identical layouts, each floor's kitchen/common break room and each signaling device 108A-D located therein can be assigned a value of 1. Thus, when the server 100 transmits the list of key modeled egress strategies to the building 102, signaling devices 108A-D in each floor's kitchen/common break room with the value of 1 can receive the egress strategies specific to egressing from the kitchen/common break room.

Once each of the signaling devices 108A-D receive the modeled egress strategies and signaling instructions, the signaling devices 108A-D can communicate and receive current conditions in real-time from the other signaling devices 108A-D and the hub 106 (step G). As previously discussed, each of the signaling devices 108A-D can collect real-time conditions on their own by using sensors or other devices integrated into each of the signaling devices 108A-D. Alternatively, the signaling devices 108A-D can communicate real-time conditions with each other as well as with sensors and other devices already installed in the building 102 (i.e., smart smoke detectors, thermocouple heat sensors, sprinkler systems, cameras, etc.). Based on the sensed/received current conditions, the signaling devices 108A-D can make real-time determinations of which egress strategies are appropriate for safe egress from the building 102.

For example, in the example mentioned above, if a fire is sensed by the signaling device 108A in the kitchen/common break room based on a sudden increase in temperature in the kitchen, then the signaling device 108A can communicate this condition in real-time to the other signaling devices 108A-D as well as the hub 106. Other signaling devices 108A-D can communicate additional conditions in real-time, including but not limited to a temperature of a space and/or a change in temperature of the space (i.e., private office, open office space). The signaling devices 108A-D can use this information to determine whether the fire is spreading from the kitchen, whether it is getting stronger, and/or whether it's getting hotter.

Based on communication of conditions in real-time in step G, each of the signaling devices 108A-D can then select an optimal egress strategy from the list of modeled egress strategies associated with the particular room/space that each of the signaling devices 108A-D is located in (step H). For example, in this step H, the signaling device 108A selects the best egress strategy that would allow an occupant to safely exit the building 102 without coming into contact with the fire that started in the kitchen, regardless of where the fire spreads. Because of the simulating and predicting performed by the server 100 in steps B-D, the signaling device 108D's selection would be accurate such that the signaling device 108D would not have to correct its egress strategy selection in real-time. This is critical in high-rise buildings because such buildings have limited possible egress routes. For example, in a residential home, an occupant can exit through a second story window. However, in a high-rise, an occupant likely can only exit through a window if the window opens and/or the window has a fire escape or other escape device (i.e., inflatable ladder, rope). Importantly, the server 100 has already simulated a fire scenario like the present one and predicted how an occupant would egress in that particular scenario (i.e., steps B-C). Therefore, the possibility of error in selection by the signaling devices 108A-D would consequently be minimal, if not nonexistent. In the event that course correction is required in real-time, then a signaling device should only have to make a single course correction and such correction can be made/determined early enough before a fire spreads to the only other possible escape route from the building 102.

In the event that the single course correction is necessary, the signaling device can continue to receive samples of temperature values from sensors throughout the building 102 as well as from the other signaling devices 108A-D and the hub 106 to make an accurate correction of the signaling device's strategy selection. In some implementations, the hub 106 (or any of the signaling devices 108A-D) can determine at various points in time to what extent initial predictions in temperature rise hold and whether they are high or low. If high, then the initial assessment of allowable egress time, as determined by the server 100, and selected egress strategy, as determined by a signaling device in real-time, holds. If low beyond a certain predetermined level, then the hub 106 and/or any of the signaling devices 108A-D can select a different egress strategy and instruct occupants to return to their starting points and/or follow new directions associated with a different selected egress strategy. In some implementations, for example, where the only other route out of the building 102 is blocked, the course correction can include instructing occupants where to safely wait for first responders to come and rescue them.

As mentioned, thermocouple heat sensors placed judiciously throughout the building 102 can sense temperatures in different rooms/office spaces in real-time. These temperature readings can be transmitted to each of the signaling devices 108A-D during the emergency and/or before the emergency. In step H, each signaling device 108A-D can estimate a rate of temperature rise along each of the modeled egress strategies to determine which of the modeled egress strategies is appropriate, safe, and ought to be selected. The signaling devices 108A-D can predict the rate of rise in temperature starting from fire initiation to maximum growth before the fire's ultimate decline. This prediction can also be performed by the server 100 before run-time execution. A temperature at any given time can be determined via thermocouple heat sensor outputs during an actual fire via a sampling process. Temperature readings from the sensors can be collected over a period of time then averaged in order to smooth the data and yield a more accurate representation of the temperature at any given time. Consequently, the signaling devices 108A-D can predict times to maximum escape temperature and flashover, which, as mentioned, is also performed by the server 100 before run-time execution. Coupled with predetermined egress transit distances and estimated egress speeds for each occupant (which was determined by the server 100 in steps B-D), the signaling devices 108A-D can accurately select and provide for proper and effective guidance to safety during an emergency in real-time.

As mentioned the determinations concerning rise of temperature can be performed by the server 100 beforehand in step C. When the server 100 determines a rise in temperature, it can employ a rationally-based audit methodology that includes extremum analysis and critical ranges of possibility to determine a temperature at any given time in each of the rooms in the building 102. Prediction of what temperatures will be at various critical points along an egress strategy (i.e., route, path) and at a destination exit point is important to ensure that occupants can be safely guided to safety without chaos or confusion. These are critical determinations performed by the server 100 in order to determine occupants' ability to safely egress during any fire scenario and model key egress strategies (i.e., steps C-D).

For example, if the sensed, determined, or predicted temperature values along an egress strategy are below a maximum escape level at all points along that strategy and will remain so until all occupants can reach the exit, then the server 100 can determine that that egress strategy is an optimal strategy in the list of modeled egress strategies provided to a signaling device. To make this determination, the server 100 needs to know a time before the temperature becomes too hot at each point along the egress strategy, a transit distance, and a speed at which an occupant is reasonably able to move along the egress strategy to safety. If conditions are not suitable to exit via one of the modeled egress strategies, with an embodied safety time factor to accommodate for any uncertainties, then the server 100 can determine that a different egress strategy in the list of modeled strategies may be the better option in the event of an emergency. These steps described can also be performed in real-time by each of the signaling devices 108A-D in step H, when each of the signaling devices 108A-D must select the optimal egress strategy from the list of modeled egress strategies received from the server 100.

After each of the signaling devices 108A-D selects the optimal egress strategy associated with the particular room/space that the signaling device 108A-D is located in (step H), each signaling device 108A-D is configured to output egress instructions associated with the selected egress strategy in step I. For example, if the fire starts in the kitchen where the signaling device 108A is located, then the signaling device 108A will output instructions associated with the selected egress strategy for exiting the building 102 from the kitchen. In the same example, the signaling device 108B, located in a private office space of the building 102, will output instructions associated with the selected egress strategy for exiting the building 102 from the private office space. As previously mentioned, output of the instructions for the selected egress strategy can be visual and/or audio. The signaling devices 108A-D can make this determination based on information about the occupants, such as whether an occupant is blind, deaf, or prefers one form of output over the other. In some implementations, the signaling devices 108A-D may only have one form of output based on the devices installed in the building 102. For example, if every floor in the building 102 has speakers installed in/integrated throughout, then audio output is preferred and used. If every floor in the building 102, or some of the floors, rooms, and/or spaces, has LED strips installed on molding of doors and/or windows, then a visual output is used. In yet other examples, output can be both audio and visual, which can be beneficial in situations where, for example, there is a lot of smoke that makes it harder for occupants to see lights as time goes on.

In other implementations, the signaling devices 108A-D can select an optimal form of output based on a current condition in real-time. For example, if the signaling device 108A senses that there is a lot of smoke in the kitchen/common break room that obstructs ones vision, it may be hard for an occupant in the kitchen to see any visual outputs. Therefore, in this example, the signaling device 108A can select an audio output of egress instructions rather than a visual output.

Each of the signaling devices 108A-D perform steps H and I. In some implementations, the hub 106 can also perform steps H and I (not shown), especially in situations where the hub 106 is located within a room/space in the building 102 that does not have its own signaling device 108A-D and wherein the hub 106 functions like the signaling devices 108A-D. In some implementations, the building 102 may not have the hub 106 but rather can designate one of the signaling devices 108A-D to act as the hub 106 or a central control system.

The signaling devices 108A-D and the hub 106 can be in communication with a device of a building manager in charge of emergency response preparedness (not depicted). In some implementations, the building manager can be an incident commander who is charged with monitoring emergencies in more than one building. The building manager's device can receive real-time updates about a fire, as well as any other information generated and/or selected by the signaling devices 108A-D and the hub 106. In addition, the building manager's device can receive information about every floor in the building 102. The building manager can have the ability to select particular floors and focus on activities and/or conditions occurring within those particular floors. The building manager can then use the device to perform certain actions during an emergency, such as activating an OEE, turning off an elevator, unlocking an emergency stairwell, activating a sprinkler system, resetting alarms, etc. As a result, the business manager is able to more appropriately respond to the emergency and facilitate safety of building occupants as well as first responders.

One or more of the signaling devices 108A-D and the hub 106 can be in communication with a device of the first responder(s) 130. The first responder(s) 130 receives status information from the devices 108A-D and/or the hub 106 in real-time so that the first responder(s) 130 can prepare (step P). The responder(s) 130 can receive the status information while on route to the building 102 where the emergency is occurring, which can help the responder(s) 130 to size up the emergency. The status information can include the building layout 104, fire conditions (i.e., where the fire started, where the fire spread, where the fire is spreading, whether windows have been blown out, whether elevators are shut down, how hot the fire is, etc.), and occupant information (i.e., how many occupants are in the building, where in the space 110A-N the occupants are located, any conditions the occupants have that may hinder their ability to safely and quickly egress, what instructions occupants have received about egressing from the building 102, etc.). The first responder(s) 130 can receive the status information on route to the building, upon arriving at the building, and/or while undergoing a rescue plan/operation in the building. Therefore, the responder(s) can be in continuous communication with devices and/or systems disclosed in reference to FIG. 1. The responder(s) can continuously receive information about floors they need to address, a state of the fire or other emergency, a number of occupants, which occupants have handicaps, etc.

The received status information can be displayed on the device of the first responder(s) 130. The device can be one or more of a mobile device (i.e., smartphone, tablet) and/or a VR device (i.e., VR headset, glasses, etc.). In some implementations, the first responder(s) 130 can wear helmets that incorporate AR and/or MR via AR and/or MR devices. The device can also be configured to select an optimal rescue plan in step Q. Potential rescue plans were generated by server 100 (i.e., steps B-E). These potential rescue plans can be communicated to the device of the first responder(s) 130 in step P. In some implementations, the potential rescue plans can be communicated directly from the server 100 to the device of the first responder(s) 130. The device can select the optimal rescue plan in step Q based, at least in part, on assessing the received status information using AI and/or predictive analytics.

Next, in step R the device can output the selected rescue plan to the first responder(s) 130. In some implementations, the device can output the selected plan by simulating the building layout 104 and visually depicted how the first responder(s) 130 can enter the building 102. For example, if the first responder(s) 130 wears a VR headset, the responder (s) 130 can undergo a simulation in which they walk through the selected rescue plan. Performing steps Q-R while the first responder(s) 130 is on route to the building 102 is beneficial to prepare the responder(s) to more calmly, quickly, and safely address the emergency and rescue the occupant(s). Moreover, during a real-time emergency, the first responder(s) can receive instructions from the device to assist the first responder(s) in making decisions and promptly acting. A combination of human response and predictive analytics and/or AI via the device can improve the first responder(s) ability to respond to the emergency as well as reduce potential stress or mental incoherency that may occur when presented with a real-time emergency.

The system described herein can further include features for assisting disabled occupants. For example, a deaf occupant can wear or carry a device (i.e. a wearable device or a hand-held device) that uses vibrational signals to guide the occupant via a selected egress strategy. As another example, a blind occupant can wear or carry a device that provides continuous audible verbal messages for egress instructions (i.e., to supplement other fixed audio devices or act as a substitute if fixed audio devices are not functioning within the building).

The system described herein can also include other features. For example, some or all devices, such as the signaling device 108 and the hub device 106, can include battery backup (i.e., lithium) for use in case of a power outage affecting some parts or all of the building. Various hardware and software security measures can further be employed to prevent local and/or remote hacking. Security measures can prevent unauthorized users (i.e., would-be thieves) from obtaining information about a building floor layout, for example. In some implementations, the system described herein can be used as a stand-alone system for a fire egress and guidance system. Other configurations for the system are also possible.

Figure 2A:
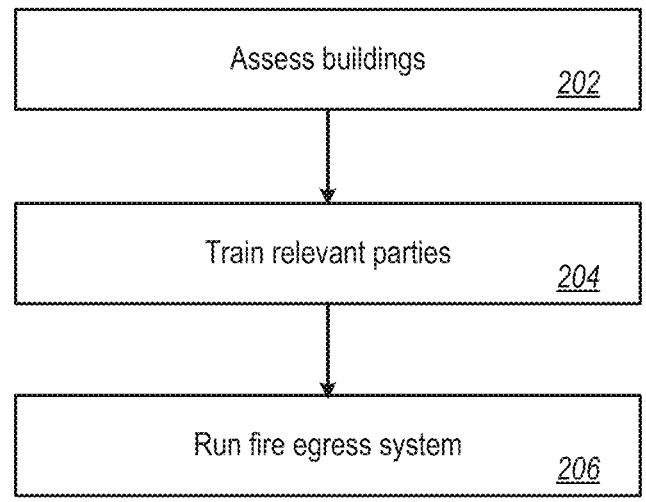
FIGS. 2A-B depict flowcharts of an example technique for operation of an egress system.
Figure 2B:
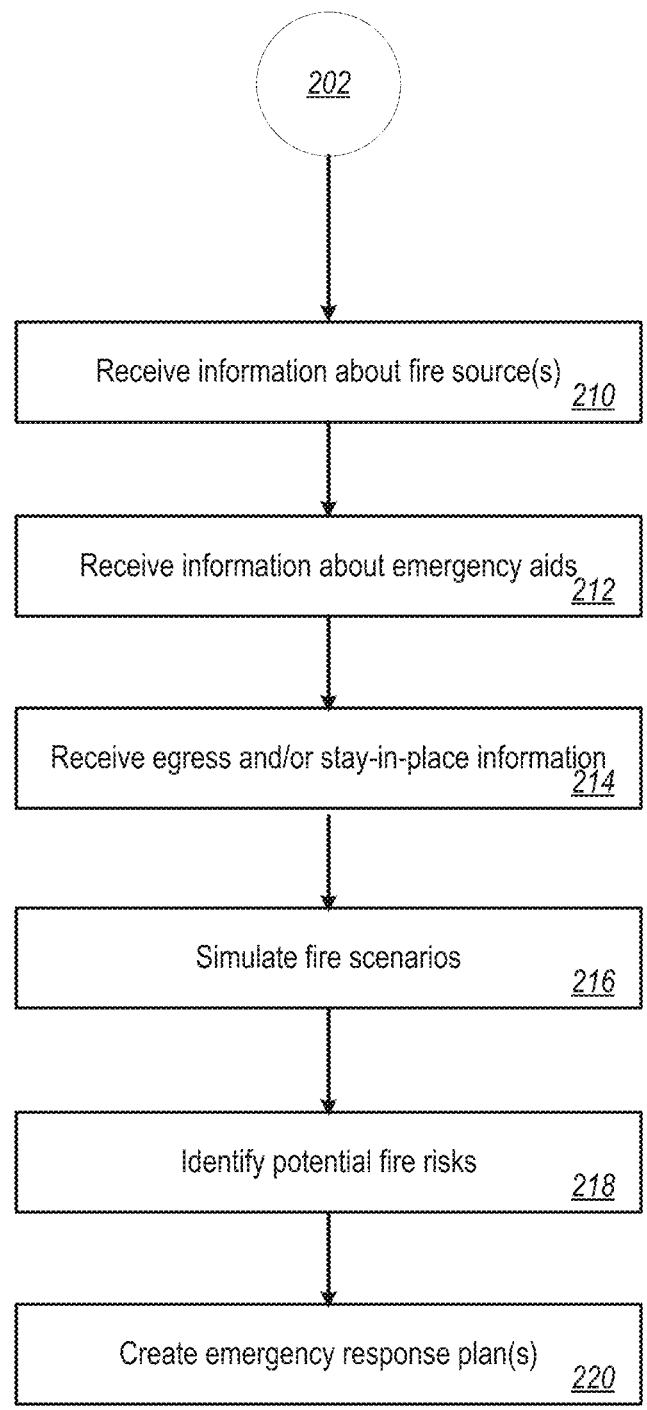

FIGS. 2A-B depict flowcharts of an example technique for operation of an egress system. FIG. 2A depicts a general overview for operation of the egress system described throughout this disclosure. First, in step 202, the system can assess information received from one or more buildings (i.e., the predictive fire pathway server 100 in FIG. 1). Based on assessing such information, the system can generate simulated training models to train relevant parties in step 204 (i.e., the training model system 120 in FIG. 1). The relevant parties can include building occupants, office managers/security offices, and/or first responders. Next, in step 206, a fire egress system can be activated (i.e., run) in real-time in response to an emergency, such as a fire (i.e., the signaling devices 108A-D and the hub 106 in FIG. 1). In step 206, a fire can be detected in the building and one of a modeled egress strategies can be selected and outputted to assist occupants in quickly and safely egressing. In some implementations, one of more of the steps 202-206 can be performed simultaneously or at different times. In some implementations, only some steps can be performed while others are not. For example, steps 202 and 204 can be performed, but step 206 may not be performed unless there is a real-time emergency in the building. Moreover, after the relevant parties are trained in step 204, step 202 can be repeated using information received and analyzed about the relevant parties' responses to the training. Iterative assessment of the buildings and training of the relevant parties can improve accuracy and effectiveness of modeled egress strategies, instructions, and simulated training models to better assist relevant parties in egressing during a real-time emergency.

FIG. 2B depicts a process for assessing the buildings (step 202). Assessing the buildings is beneficial to generate optimal simulated training models so that trainees (i.e., building occupants, first responders, etc.) are prepared to more safely and quickly egress from a building during a real-time emergency. First, the system can receive information about potential fire sources within a building (step 210). Such information can include objects and/or structures that are vulnerable to fire, such as kitchen appliances in a common break room. The system can also receive information about whether the building is made with wood and/or materials more susceptible to starting a fire and/or burning during a fire.

In step 212, the system can receive additional information about emergency aids throughout the building. This information can indicate what emergency aid devices are located within the building and where, such as fire extinguishers, sprinkler systems, OEEs, emergency stairwells, fire escapes, inflatable ladders, ropes, etc. This information can further include whether fire extinguishers are up to date, whether fire, smoke, and/or carbon monoxide detectors are properly functioning (i.e., new batteries are installed), and/or whether sprinkler systems are present and/or activated.

In step 214, the system can also receive egress and/or stay-in-place information. The egress and/or stay-in-place information can be generated by the server 100 described in reference to FIG. 1. The egress and/or stay-in-place information can include a list of potential egress routes out of the building as well as instructions to go to and/or remain in a particular area of the building until first responders arrive to rescue occupants.

The system can use the information received in steps 210-214, in addition to AI and/or predictive analytics, to simulate fire scenarios in step 216. The system can simulate fire scenarios that are generally applicable to the plurality of buildings that are being assessed. In other implementations, the system can simulate fire scenarios that are specific to a particular building. Based off the simulated fire scenarios and using AI and/or predictive analytics, the system can identify potential fire risks in step 218. The system can determine potential causes of fire within the building, how the fire can spread to different parts (i.e., floors) of the building, and other issues the fire can cause that can hinder quick and safe egress from the building.

In step 220, the system can generate emergency response plan(s). The plan(s) can be based on the simulated fire scenarios in step 216 and the identified fire risks in step 218. The system can also generate different response plan(s) based on the relevant parties. For example, the system can generate a plan that requires building occupants to seek shelter in a private office with a window that is far away from a fire. The system can also generate a plan that requires first responders to enter through the window in the private office to rescue the occupants. Moreover, the system can generate a plan that requires building managers/security officers to activate and/or deactivate an elevator and/or OEE. Once steps 210-220 are completed by the system, the system can perform steps 204-206 depicted in FIG. 2A. Training the relevant parties in step 204 can include using the simulated fire scenarios from step 216 and the emergency response plan(s) from step 220. Moreover, running the fire egress system in step 206 can include using the identified potential fire risks from step 218 and the emergency response plan(s) from step 220.

Figure 3:
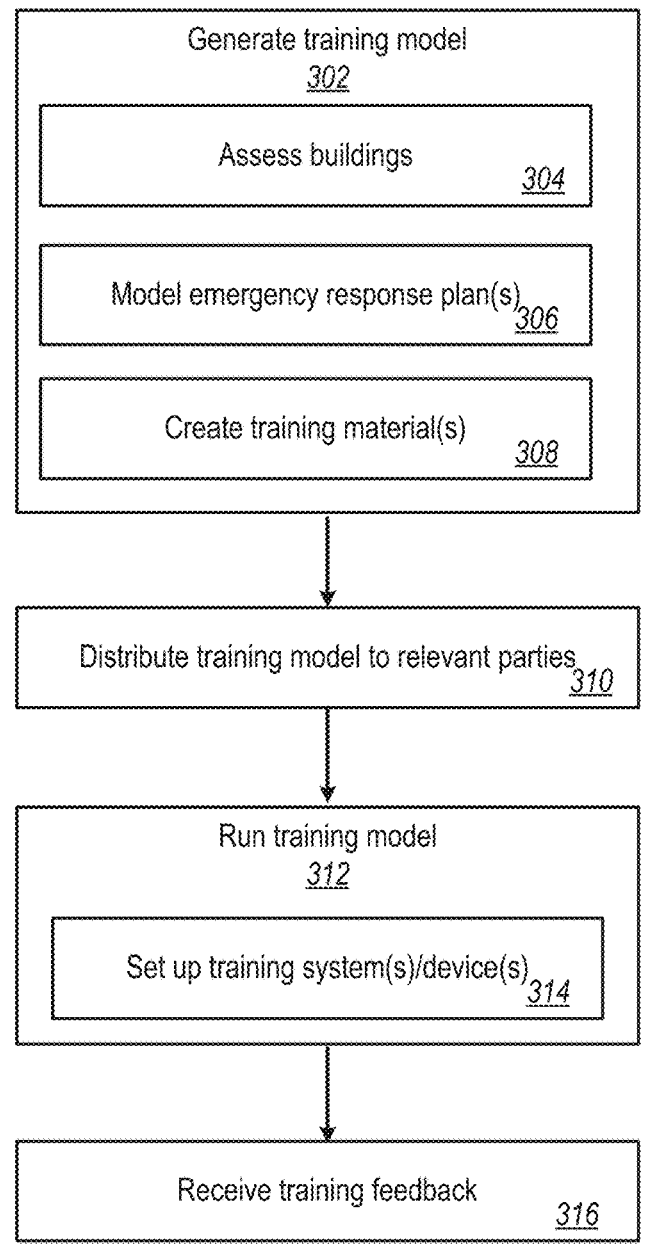
FIG. 3 depicts a flowchart of an example technique for generating and implementing a simulation training model.

FIG. 3 depicts a flowchart of an example technique 300 for generating and implementing a simulation training model. Technique 300 can be performed by a computer system, such as the training model system 120 (i.e., FIG. 1) as described throughout this disclosure. First, the system can generate a training model in step 302. Generating the model can include assessing one or more buildings (step 304), modeling emergency response plan(s) (step 306), and creating training material(s) (step 308). Assessing one or more buildings in step 304 is discussed in reference to FIGS. 2A-B. Modeling emergency response plans in step 306 can include modeling rescue plans as well as evacuation plans, the plans being specific to different parties. For example, evacuation plans can be generated for building occupants who are going to undergo the generated training model. Rescue plans can be generated for first responders who are going to undergo the generated training model. Modeling emergency response plans is also discussed in further detail throughout this disclosure. Creating the training material(s) in step 308 can include generating simulation models of different fire scenarios in different buildings. Step 308 can include employing/integrating AR, VR, MR, and/or XR into the simulated models such that trainees can experience (i.e., walk through) a fire scenario and emergency response plan. For example, the system can generate a VR replication of a particular building as part of the training material(s). A trainee would then go into this VR replication, receive one of the modeled emergency response plan(s), which can include instructions on how to egress from the VR replication of the building, and follow the plan to exit the VR replication of the building.

Once the training model is generated in step 302, the system can distribute the training model to relevant parties in step 310. Relevant parties can include building occupants, first responders, office managers/security officers, etc. Next, the training model can be run in step 312. Running the training model includes setting up a training system(s) and/or device(s) in step 314. Step 314 can include setting up/initiating VR devices, such as VR headsets and/or glasses, computer systems, and biometric sensors. For example, the simulated training model can be installed on a VR headset. A smartwatch and/or heartrate monitor can be attached to a trainee who is wearing the VR headset. The smartwatch and/or heartrate monitor can be configured to be in communication with the VR headset and/or the system described herein such that real-time biometric conditions of the trainee can be collected as the trainee undergoes the training simulation.

In step 316, the system can receive training feedback. The feedback can include biometric data about the trainee while the trainee was undergoing the training simulation. The feedback can also include an amount of time that the trainee took to undergo the training simulation. The received training feedback can then be used by the system to generate improved training models, mental models associated with each trainee and/or groups of trainees, and/or improved egress strategies/instructions (i.e., FIGS. 4-6).

Figure 4A:
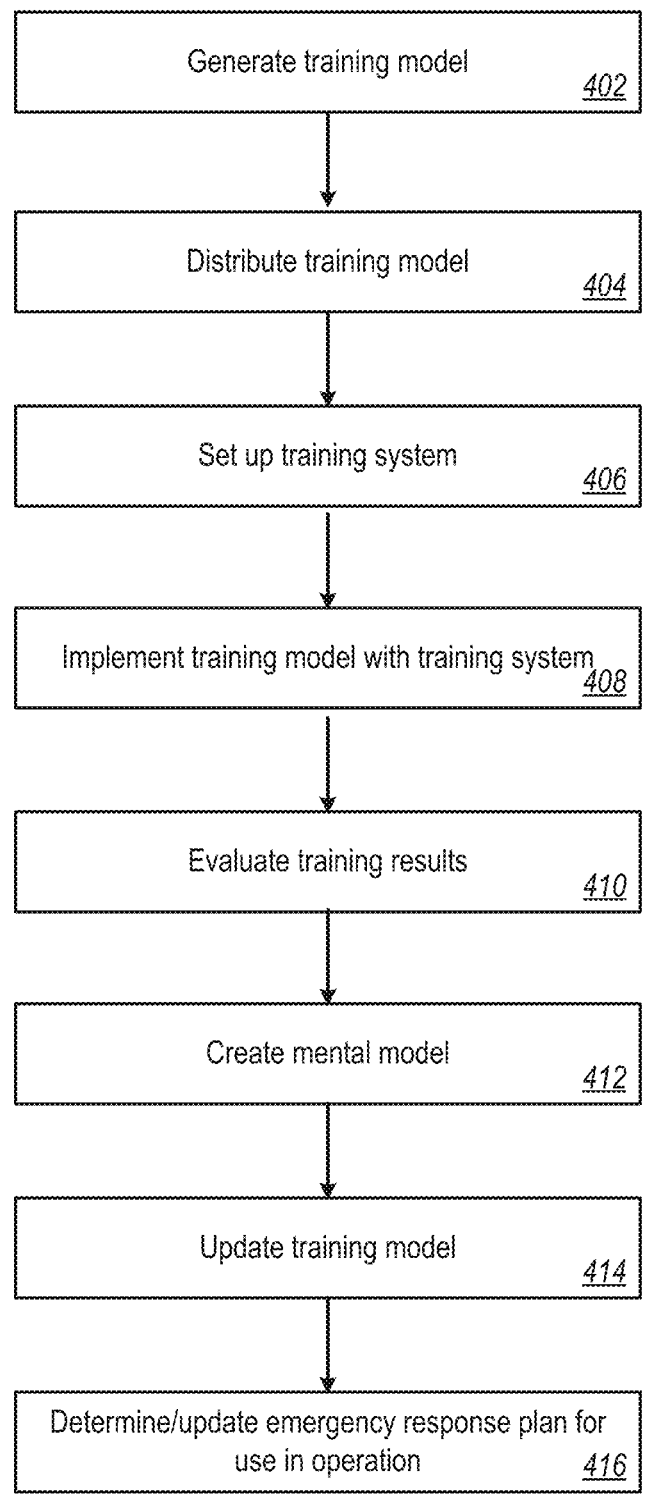
FIGS. 4A-B depict flowcharts of an example technique for generating a simulation training model.
Figure 4B:
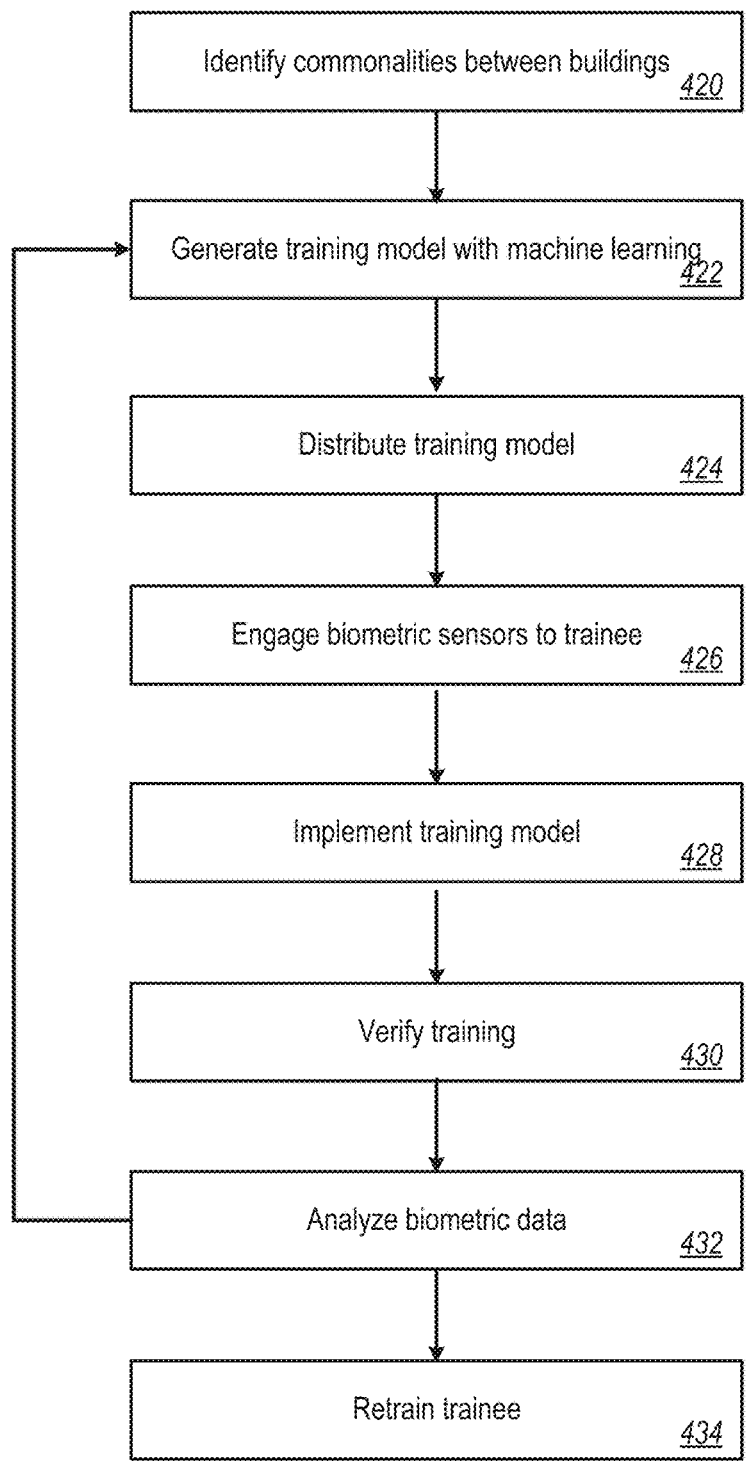

FIGS. 4A-B depict flowcharts of an example technique for generating a simulation training model. A computer system such as the training model system 120 (i.e., FIG. 1) can perform the technique disclosed in FIGS. 4A-B. Referring to FIG. 4A, the computer system can generate a training model in step 402 (i.e., FIGS. 1-3). When generating the training model, the computer system can create fire scenarios that are more complicated and/or extreme than a real-time fire emergency. Surprise factors can be incorporated into the training model to determine how trainees respond to startling/unexpected events. Doing so can prepare trainees to better cope with and respond to any type of real-time emergency. For example, a training model for first responders can incorporate wind-driven fires, intricate flow paths, and/or complex smoke flow such that the first responders learn how to deal with different types of smoke behavior and other patterns that may be disorienting. Moreover, the fire scenarios can teach first responders how to operate different equipment, including equipment they have never seen or used before. Learning how to use the different equipment through virtual environment training can better prepare the first responders rather than learning how to use the equipment for the first time on the scene during a real-time emergency.

The training model can be distributed in step 404 (i.e., FIGS. 1-3). A training system can be set up in step 406 (i.e., FIG. 3). Set up can include installing and/or uploading the training model onto a VR headset or other device, such as a tablet, computer, and/or smartphone. Setting up the training system can further include implementing wearable devices and/or sensors to detect trainee response data to the training model.

Next, the training model can be implemented with the training system in step 408. Implementing the training model includes running the training model and having trainees undergo the training model. In other words, trainees are immersed in a simulated fire scenario using virtual reality and can interact in such a virtual environment. Implementation can include individual training and/or team-based training. For example, first responders can undergo the same training model and interact with each other through the virtual environment. In some examples, a building manager/security officer can undergo the training model to learn how to orchestrate emergency response amongst other team members and/or relevant stakeholders/parties (i.e., specialized emergency responders, building managers, building engineers, etc.).

Implementing the training model further can include recording/collecting biometric data and other information about the trainees as they undergo the training model. During the implementation step, trainees may also undergo a decompression phase after going through the training model. The stress and potential horror of harrowing, life-like training scenarios created by VR can put certain trainees into a discomforting mental state. Thus, it is imperative to transition the trainees back to a comfortable and stable state of mind. Doing so can assist the trainees to overcome the stress and potential horror such that in a real-time emergency, where the intensity of the emergency may actually be less than that within the training model, the trainees will be able to better cope and respond.

In step 410, training results can be analyzed and evaluated using AI and/or predictive analytics. In this step, the computer system can evaluate how quickly a trainee made it through the training model (i.e., a fire started in an elevator bank and the trainee was instructed to close themselves in a private office at an opposite end of the building until first responders arrived), whether the trainee experienced an increased heartrate, abnormal sweating, and/or inability to follow egress instructions that are given to the trainee during the simulation. Evaluating training results is also beneficial to assess skills that a trainee (i.e., first responder) currently possesses, their weak spots, and their developmental potential. Evaluating the training results can also be performed in order to determine a range of scenarios to put the trainee in next and whether to expose the trainee to rare events from which they can develop highly expert mental models.

Based on evaluation in step 410, the computer system can create a mental model in step 412, using predictive analytics, statistical methods, and/or AI. The mental model(s) can be robust to account for unexpected behaviors and/or actions that may occur during an unpredictable emergency. By incorporating such expectancies and integrating those into the training model, trainees can more calmly undergo the training model as well as a similar emergency in real-time. As a result, during a real-time emergency, occupants and/or first responders can avoid having the stress to observe, orient, decide, and act (OODA) to an unpredicted scenario.

The mental model can be specific to a particular trainee. In other implementations, the mental model can be generated for a group/class of trainees. In yet other implementations, the mental model can be generated based on a situation or combination of events. For example, first responders can be grouped together for one mental model while building occupants can be grouped together for a second mental model. Rigor and level of reality and stress in the training model can be greater for first responders than for occupants because first responders are psychologically equipped for emergencies, by selection and training, whereas occupants typically are not. The training models for both responders and occupants can attend to the psychological needs and resilience of these respective groups. Information-based AR and MR can therefore guide people that have to stay in place, or to remain patient while queueing for elevators or stairways. How trainees respond to the training models can be beneficial for the computer system to generate mental models that will aid the trainees in more calmly dealing with decision-making during real-time emergencies. Developing robust mental models can be beneficial to instill trainees with good/better judgment during a real-time emergency. As a result, during a real-time emergency, a building occupant and/or a first responder will not have to construct their own mental models on the spot and while under the stress of the emergency. In some examples, during an emergency, first responders may not have all the necessary information to respond to the emergency and/or rescue building occupants. However, robust mental models, as developed in step 412, can incorporate predictive analytics and/or AI to prepare the first responders for dealing with different types of emergencies that may occur in real-time. As a result, even if the responders receive flawed and/or incomplete data about the emergency in real-time, the mental models and training models described throughout this disclosure can improve the responders' performance by teaching them how to act and/or make decisions in any situation.

Moreover, in reference to building occupants, the computer system can observe, predict, and decide what actions the building occupants should take during an emergency, and present those actions to the occupants via the training model. As a result, the computer system can generate mental models for the occupants in step 412 such that the occupants can better cope with high stress and uncertainty in real-time emergencies. In other words, the techniques described throughout this disclosure can lessen a psychological burden on the occupants who generally are not trained or suited for effective, coherent thought and action when faced with real-time emergencies.

In step 414, the computer system can update the training model. The mental model(s) created in step 412 can be used to make improvements to the training model. Using the mental model is beneficial because the mental model can help instill better judgment in trainees, such as first responders. For example, the improved training model can incorporate elements of the mental model that suggest alternative rescue plans that reduce a level of stress in the first responder and provide for a safer and faster entry into the building. When the first responder undergoes the improved training model, the first responder can develop better judgement and decision-making that is applicable to any emergency in real-time. As a result, in a real-time scenario, the first responder would not have to develop a mental model/decisions in the moment. Moreover, improving the training model with the mental model can assist the trainees in gaining appreciable skills by virtue of undergoing more arduous training scenarios. In some implementations, training models can be updated to be harder and/or having more extreme emergencies/conditions. In yet other implementations, updating the training model can include adding interaction amongst multiple trainees in a simulated virtual environment. For example, an improved training model can be undergone/implemented by multiple trainees simultaneously (i.e., a team of first responders). In the simulated virtual environment, the trainees can interact with each other as well as the virtual environment, which can add additional levels of complexity, stress, and challenge to dealing with an emergency situation.

Once the training model is updated in step 414, emergency response plans for use in operation of the disclosed egress system can be determined and/or updated (step 616). The emergency response plans can be updated to reflect optimal egress routes, strategies, and/or instructions based in part on how essential stakeholders (i.e., trainees) responded to the training model as well as the generated mental models. For example, if building occupants were stressed while undergoing the training model and following an egress strategy that required them to run down several flights of stairs, the computer system can determine that the optimal egress strategy for such occupants in real-time would be to direct them to an OEE. In the same example, the computer system can determine to keep the strategy to escape by the stairs for occupants who were not stressed having to escape via the stairs in the training model.

Referring to FIG. 4B, the computer system described throughout this disclosure can identify commonalities between a plurality of buildings in step 420. Step 420 can include identifying common floorplans, layouts, egress strategies, egress instructions, and occupants from the plurality of buildings. In step 422, the computer system can generate a training model, using machine learning algorithms, based at least in part on the identifications in step 420. As a result, a general training model can be generated, which can be applicable to occupants and other stakeholders in different buildings. In step 424, the training model can be distributed to the relevant stakeholders. As previously described, the training model can be installed/uploaded onto devices that the stakeholders will use for undergoing/implementing the training model. Next, one or more biometric sensors can be engaged to the stakeholders or trainees who will undergo the training model (step 426). Exemplary biometric sensors include a smartwatch and/or heart rate monitor. The biometric sensors can be configured to record information/biometric data about the trainees as they are immersed in the training model.

Next, in step 428, the training model can be implemented, as previously described. In step 430, the computer system can verify that training occurred. The computer system can receive confirmations from the devices used by the trainees to undergo/implement the training model. The confirmations can include information about how long it took a trainee to complete the training model, when the trainee completed the training model, and the trainee's biometric data. Upon receiving such information, the computer system can analyze the biometric data in step 432. As mentioned in reference to FIG. 4A, the biometric data can be analyzed to create mental models for each of the trainees. The biometric data can also be analyzed to determine how to improve/modify the training model.

Thus, after analyzing the biometric data in step 432, the computer system can return to step 422 and repeat the steps 422-432. The computer system can repeat the steps 422-432 to continuously improve the training model as well as the AI and/or predictive analytics algorithms that are used to generate the training model, egress strategies and instructions, and fire predictions. Continuous improvement can ensure the computer system can accurately predict and respond to any potential emergency scenario.

Finally, in step 434, trainees can be retrained. Retraining can occur with a previous training model, a new training model, and/or an improved/modified training model. In some implementations, trainees can be retrained until they perform at a desired level in the training model(s). For example, a building occupant can undergo multiple training models having different emergency scenarios until the occupant completes each of the training models with a heartrate that is below a predetermined threshold value. As another example, a first respond can undergo multiple training models having different emergency scenarios until the first responder adequately and correctly operates new emergency equipment. In some implementations, a building officer/manager may require occupants to undergo training at predetermined times throughout a calendar year. Each time, the occupants can be retrained as described in reference to FIGS. 4A-B.

Figure 5:
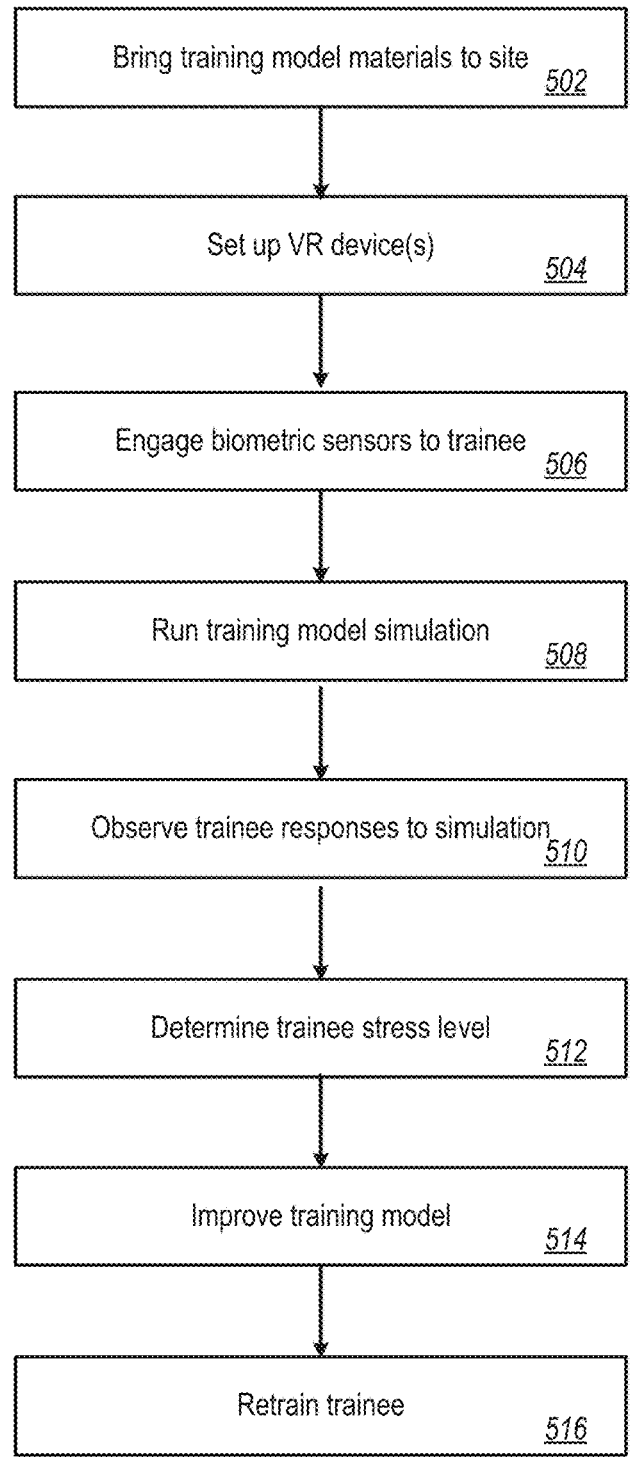
FIG. 5 depicts a flowchart of an example technique for implementing and improving a simulation training model.

FIG. 5 depicts a flowchart of an example technique for implementing and improving a simulation training model. First, the training model materials described throughout this disclosure can be brought to a training site in step 502. The training site can be a building where building occupants are required to undergo safety training. In other implementations, the training site can be a firehouse or other location where first responders undergo safety training. In yet other implementations, the training materials can be communicated, via a network, to one or more devices that are used (i.e., remotely) to train stakeholders. For example, a building occupant can be required to undergo the training model at home.

In step 504, one or more VR devices can be set up with the training materials. As described throughout this disclosure, the VR device can include a VR headset, glasses, a tablet, a smartphone, and a computer/laptop. Setting up the VR device can include installing and/or uploading the simulated training model to the device.

Prior to running the training model, one or more biometric sensors can be engaged to a trainee in step 506, as described previously. Then, in step 508, the training model can be run. While the trainee is undergoing/immersed in the training model simulation, the trainee's responses to the simulation can be observed and recorded (step 510). Step 510 can be accomplished by a computer system as described throughout this disclosure. Information about the trainee's responses can be collected via the biometric sensors and/or the VR device. Once the trainee's responses to the simulation are collected, the computer system can determine the trainee's level of stress in step 512. Determining the trainee's level of stress can be beneficial to generate a mental model for the trainee, as described throughout this disclosure (i.e., FIG. 4A). The trainee's stress level is also critical to determine whether the trainee needs to undergo additional training models, whether the trainee needs to receive different egress instructions, and/or whether the trainee would need help from other occupants or stakeholders to safely egress during an emergency. Next, in step 514, the computer system can improve the training model, as described throughout this disclosure. The trainee can then be retrained using the improved training model and/or new training models in step 516, as described throughout this disclosure.

Figure 6A:
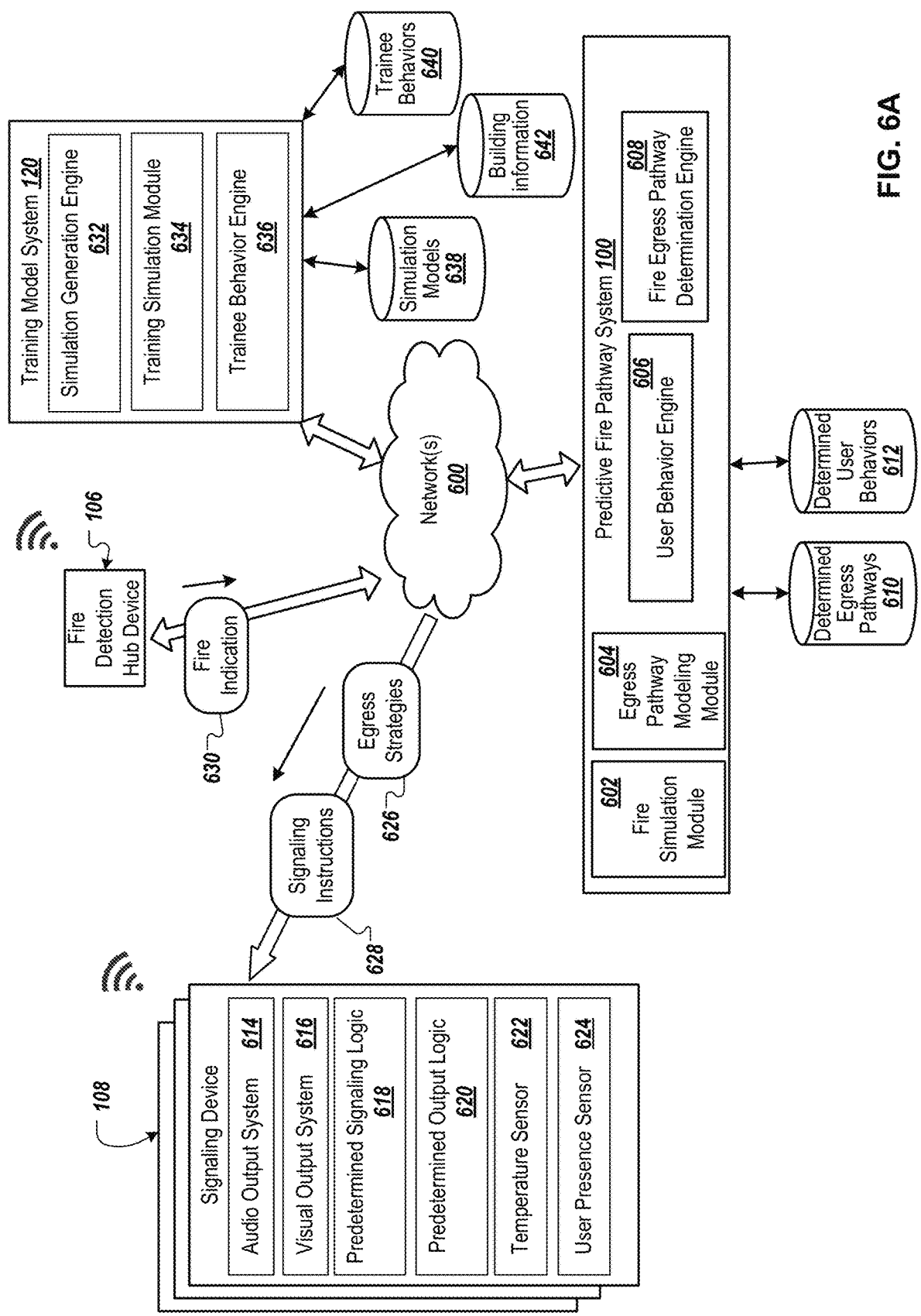
FIGS. 6A-B are example system diagrams of the embodiment of FIG. 1.
Figure 6B:
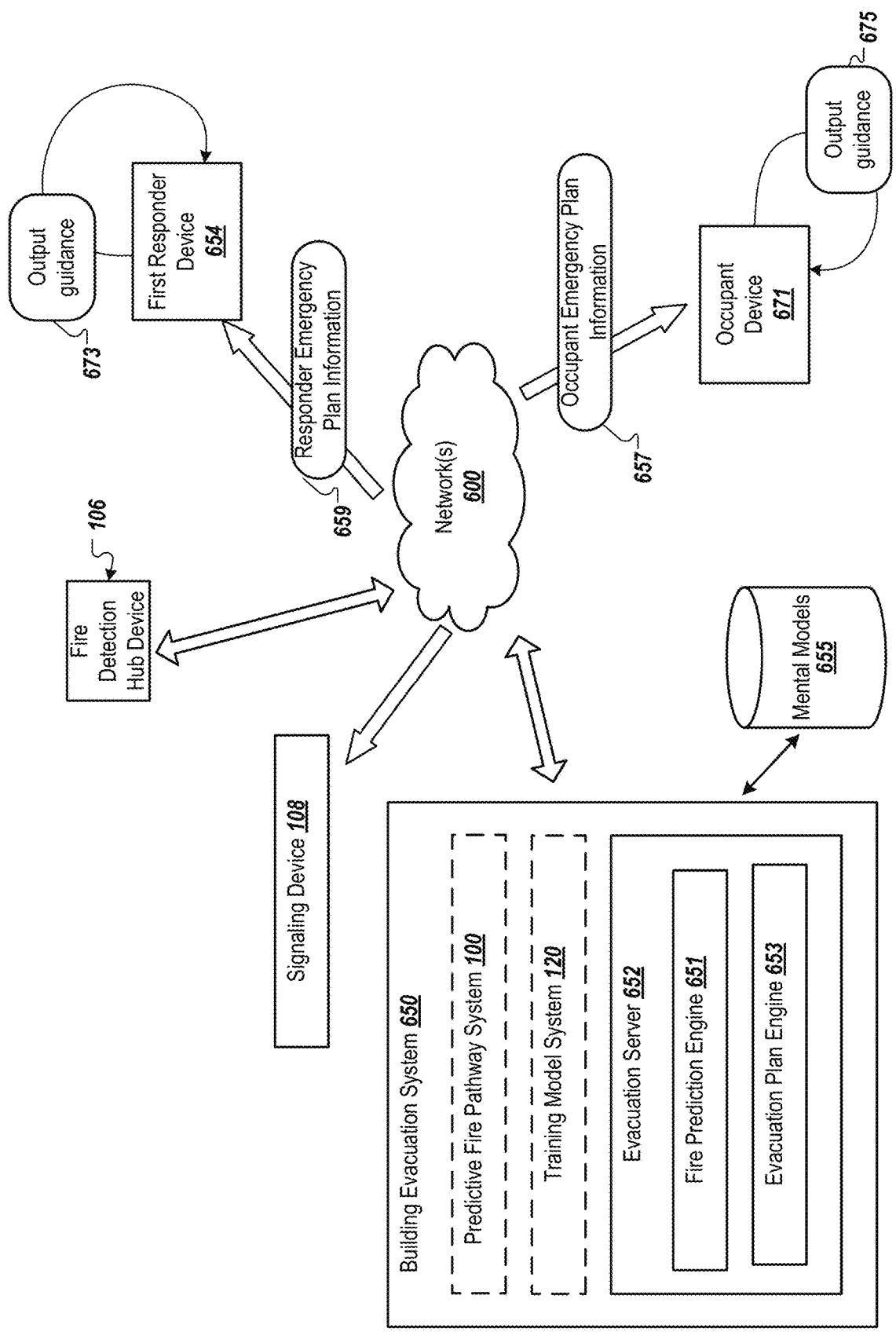
Figure 6C:
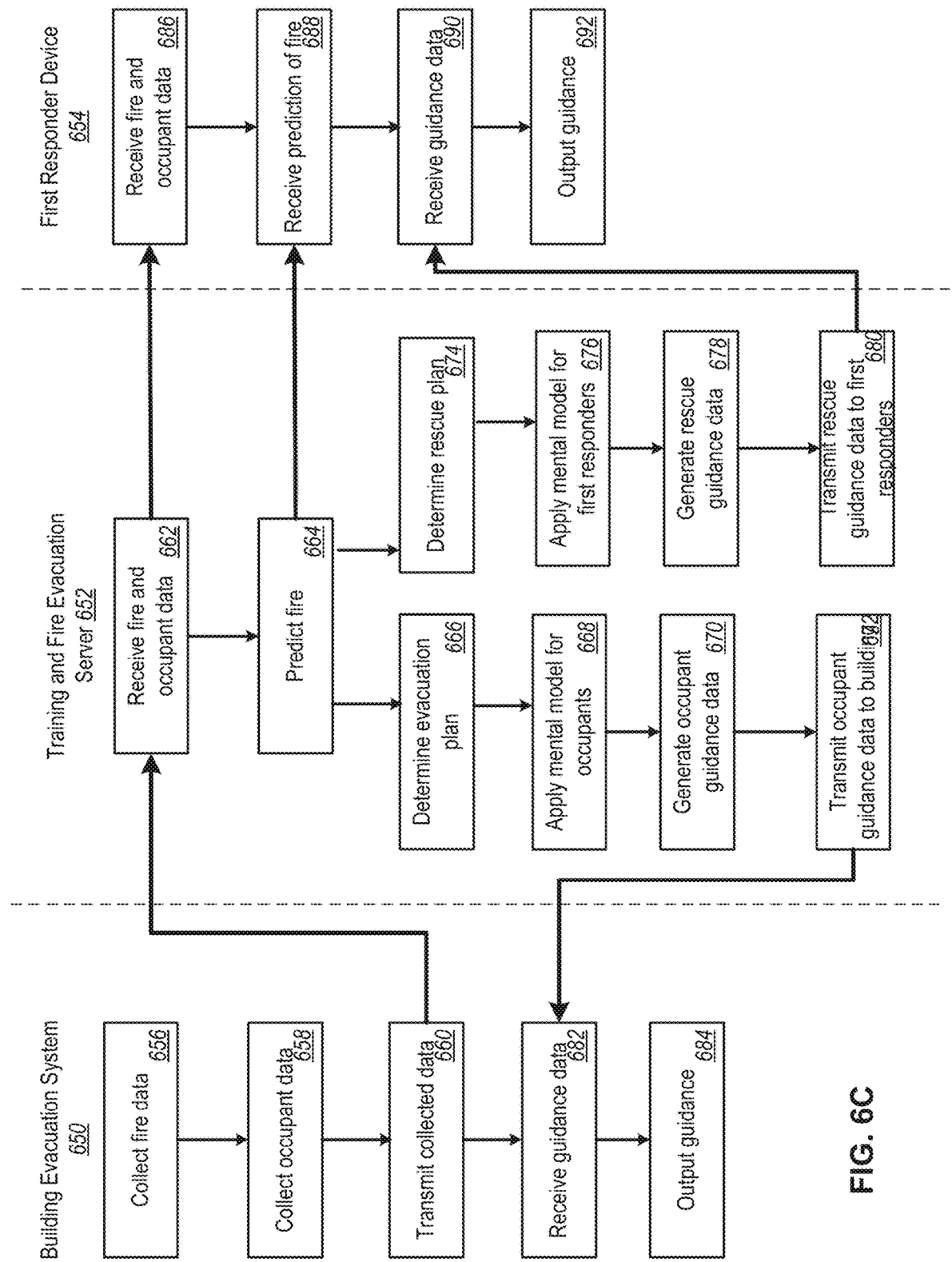
FIG. 6C is an example flowchart of interaction between components of the embodiment of FIG. 1 in real-time during an emergency.

FIGS. 6A-B are example system diagrams of the embodiment of FIG. 1. FIG. 6C is an example flowchart of interaction between components of the embodiment of FIG. 1 in real-time during an emergency. Referring to FIG. 6A, the system includes a predictive fire pathway system 100 (FIG. 1's predictive fire pathway server 100), a fire detection hub device 106 (FIG. 1's hub 106), at least on signaling device 108 (FIG. 1's signaling devices 108A-D), and a training model system 120 (FIG. 1's training model system 120) that communicate via network(s) 600. The system 100, hub device 106, signaling device 108, and training model system 120 can use one or more wired and/or wireless communications (i.e. BLUETOOTH, WIFI) in the network(s) 600.

The training model system 120 can include a simulation generation engine 632, a training simulation module 634, and a trainee behavior engine 636. As previously mentioned, the system 120 can receive building layouts and/or other building information, via the network(s) 600 from one or more buildings and/or predictive fire pathway systems 100 (i.e., FIG. 1 step J). The building layouts/information can be stored in a building information database 642. The simulation generation engine 632 can then generate at least one simulated training model based on identifying commonalities amongst the information stored in the database 642 (i.e., FIG. 1 step K). Some of these commonalities can include locations of sensors throughout the building (i.e., temperature sensors, sprinklers, etc.), egress strategies, egress instructions, building layout, and occupant information. As previously mentioned, the simulated training model can be applicable to buildings that share the commonalities. The engine 632 can also generate simulated training models specific to a particular building and/or a particular building layout. For example, first responders may receive a training model about a specific building that is on fire, which the first responders are traveling to. In other implementations, the training model applicable to several buildings can be beneficial for routine safety training procedures that are required for all building occupants (i.e., new hires) to complete. Once the training model is generated, it can be stored in a simulation models database 638.

As previously described, the training model(s) can be distributed to relevant stakeholders in buildings and undergone by those stakeholders (i.e., FIG. 1 steps L-M). The system 120 can receive biometric data from sensors worn by the stakeholders while experiencing the simulated training models (i.e., FIG. 1 step N). The received biometric data can be stored in a trainee behaviors database 640. The trainee behavior engine 636 can analyze the data stored in the database 640 and determine how stressed trainees were during the simulations. Based on the determined stress levels and whether those stress values exceed predetermined threshold values, the engine 636 can determine improvements/modifications to simulation training models. The trainee behavior engine 636 can be in communication with the simulation generation engine 632 in order to ameliorate existing simulation training models stored in the database 638 and/or generate new/improved training models. Predictive analytics, artificial intelligence, and/or other machine learning techniques can be employed by the training model system 120 in order to further improve the simulated training models. Moreover, over time, the simulation generation engine 632 can access information stored in the simulation models database 638, the trainee behaviors database 640, and/or the building information database 642 in order to generate improved simulated training models that account for any emergency/fire scenario, any building, and/or any building layout. In some implementations, the training model system 120 can also receive information from the predictive fire pathway system 100, such as determined egress pathways, in order to improve and/or generate more robust simulated training models.

The iterative process of generating and improving simulated training models, as described above, is beneficial to ensure that trainees are exposed to varying stressful emergency situations so that the trainees know how to cope and respond to such situations in real-time. This iterative process is beneficial to reduce stress and chaos that may occur in the event of a real-time emergency, such as a fire. This iterative process is further beneficial in order to determine what egress strategies and/or routes are optimal to avoid stress and/or chaos during an emergency in any building layout and/or building.

In some implementations, the hub device 106 can detect whether there is a fire in a building and provide an associated fire indication 630 to the predictive fire pathway system 100 as well the signaling device 108. The hub device 106 can be of various configurations and can include a smoke detector and/or heat sensor (i.e. temperature sensor, infrared sensor, etc.) in order to detect whether there is a fire and where in the building the fire is located. Further, the hub device 106 and/or signaling device 108 can be of various configurations, such as motion sensors, cameras, door sensors, window sensors, door locks and window locks, other security devices, etc.

The predictive fire pathway system 100 can include a fire simulation module 602, an egress pathway modeling module 604, a user behavior engine 606, and a fire egress pathway determination engine 608. The system 100 can also communicate wirelessly and/or wired with a determined egress pathways database 610 and a determine user behaviors database 612. In other implementations, the system 100 can alternatively store information associated with its functions in a cloud-based network and/or use the cloud-based network as backup storage.

The user behavior engine 606 can collect information about home occupants from the hub 106, signaling device 108, or other sources (i.e., FIG. 1 step A). For example, when the hub 106 and signaling device 108 are installed in the building, an installer (i.e., building occupant, builder, etc.) can input/transmit information about the building's occupants directly to the predictive fire pathway system 100. Some of the information that the user behavior engine 606 can collect includes an age, agility level, and any possible disabilities associated with each occupant. The user behavior engine 606 can then determine key characteristics of the occupants that may impact their ability to safely egress from the building during an emergency. For example, if an office worker is in a wheelchair, then the user behavior engine 606 can determine that this factor will change how the worker can egress from the building during a fire. In other words, it may take longer for the worker to egress and a stairwell may not be the optimal egress route. The user behavior engine 606 can also use this type of occupant information in order to suggest to a builder, building occupant, or any other relevant stakeholder about what modifications can be made directly within the building to ensure occupant safety. For example, the user behavior engine 606 can create a suggestion, communicated to the hub device 106 to then be outputted for display, that the office worker with the wheelchair should have an office space/desk closest to an elevator.

Once the user behavior engine 606 determines the user information that is key to egressing safely out of the building during an emergency, that user behavior information can be stored in the determined user behaviors database 612. The information stored in the database 612 can be updated at any time by a user inputting updated and/or new information into the hub device 106. For example, if a client visits an office for the day, one of the office occupants can update the occupant information via the hub device 106 such that when egress pathways are modeled by the module 604, the module 604 can take into consideration the fact that a visitor is now one of the occupants that would need to safely egress from the building during an emergency.

Still referring to FIG. 6, the fire simulation module 602 can simulate potential fire scenarios in the building based on a building layout, what materials the building is built with, how many floors are in the building, user behavior information, and other information as previously mentioned (i.e., FIG. 1 step B).

The egress pathway modeling module 604 can be configured to model/create potential egress strategies out of the building based on the simulated fire scenarios from the module 602 and taking into consideration the occupant information stored in the determined user behaviors database 612 (i.e., FIG. 1 step C). The module 604 can use predictive analytics and components of artificial intelligence to predict abilities of each of the occupants to exit the building during an emergency, no matter the simulated fire scenario.

The fire egress pathway determination engine 608 can be configured to select one or more of the predicted egress pathways from the module 604 that can be used during an emergency (i.e., FIG. 1 step D). In this step, the engine 608 can model the predicted egress strategies for each of the rooms/spaces in the building, thereby creating a list of key potential egress strategies that the signaling device 108 can choose from in real-time. The engine 608 can also be configured to model signaling instructions associated with each of the potential egress strategies in the list (i.e., FIG. 1 step E). In some implementations, as previously discussed, the engine 608 can list the egress strategies in order from optimal to least optimal exit strategy in any given fire scenario.

Once the engine 608 determines a list of egress strategies associated with each room/space in the building, the list of egress strategies, as well as the associated signaling instructions, can be stored in the determined egress pathways database 610. Over time, if the module 604 predicts new egress strategies and the engine 608 models, selects, and/or determines new strategies that can be implemented by the signaling device 108, then egress strategies stored in the database 610 can be updated to reflect such changes/additions. Thus, the module 604 operates to bolster functioning and effectiveness of the system 100 by adjusting the system 100 for changing circumstances in occupant status, occasions with visitors, and/or changes in the building itself (i.e., renovating a floor, adding private offices, installing new kitchen/break room appliances, adding windows that can open, installing fire escapes/emergency exit devices, etc.). As such, egress strategies can be modified rapidly with changing circumstances.

After egress strategies are determined and stored, the system 100 can communicate the egress strategies 626 and the associated signaling instructions 628 to the signaling device 108 (i.e., FIG. 1 step F).

The signaling device 108 can include an audio output system 614, a visual output system 616, a predetermined signaling logic 618, a predetermined output logic 620, a temperature sensor 622, and a user presence sensor 624. Upon receiving the egress strategies 626 and signaling instructions 628, the signaling device 108 can collect current conditions in real-time (i.e., FIG. 1 step G). The temperature sensor 622 (i.e. heat sensor, infrared sensor, etc.) can get a read on a temperature of the room/space that the signaling device 108 is located within. Based on the sensed temperature, the signaling device 108 can determine whether there is a fire in the room/space and/or whether a fire is spreading/getting closer to the room/space. Moreover, the user presence sensor 624 can determine whether an occupant is located within the room/space. If the occupant is sensed in the room/space, then the signaling device 108 can determine that it must output some instructions to that occupant to safely egress from the room/space.

The predetermined signaling logic 618 can then select an optimal egress strategy from the list of egress strategies 626 (i.e., FIG. 1 step H). This selection can be based on information sensed in real-time by the temperature sensor 622 and/or the user presence sensor 624, as previously discussed throughout this disclosure. Once an egress strategy is selected, the predetermined output logic 620 can determine which form of output should be used to output the egress instructions. This determination can be based on user information, preferences, and/or what devices are installed within the room/space that the signaling device is located in. Based on that determination, the signaling instructions can be outputted using the audio output system 614 and/or the visual output system 616 (i.e., FIG. 1 step I).

In some implementations, the signaling device 108 can include and/or be coupled to an apparatus having a user detector, fire detector, communication device, speaker, and a display device. The user detector can operate to detect user motion or presence around the signaling device 108 over time. The user motion or presence can be recorded locally in the signaling device 108 and/or in one or more remote computing devices. As described herein, the user detector can be of various types, such as motion sensors and cameras. In addition or alternatively, the user detector can include a door/window sensor, door/window locks, etc. The fire detector can operate to detect presence and location of fire. Information on the fire presence and location can be recorded locally in the signaling device 108 and/or in one or more remote computing devices. As described herein, the fire detector can be of various types, such as a smoke detector and a heat sensor (i.e., a temperature sensor, an infrared sensor, etc.). The communication device is included in the signaling device 108 and configured to enable data communication with the hub and other signaling devices. The communication device can include a wireless or wired data communication interface. can include a wireless or wired data communication interface. The speaker can operate to generate sounds, such as audible cues, horns, or verbal messages for egress guidance. The speaker can be used to supplement other fixed audio devices or act as a substitute if fixed audio devices are not functioning. Such sounds can complement visual signs in situations where smoke intensity can diminish or preclude the ability to see the visual signs. The display device can operate to display visual signs that can guide a user along a selected egress route. In some implementations, the display device includes a display screen that is provided in the signaling device 108 and displays information with visual signs thereon. In addition or alternatively, the display device can operate as a projector that projects a lighted sign on another object, such as a wall, a floor, or a ceiling.

Now referring to FIG. 6B, the system includes a building evacuation system 650, an occupant device 671, a first responder device 654, at least one of the signaling devices 108, and the fire detection hub device 106. As depicted, the systems and devices described herein can be in communication via the network 600. The building evacuation system 650 can optionally include the predictive fire pathway system 100 and the training model system 120 described throughout this disclosure. In some implementations, the systems 100 and 120 can be separate systems in communication with the building evacuation system 650 via the network 600. Moreover, the system 650 can control the one or more signaling devices 108 and/or the hub 106.

The building evacuation system 650 includes an evacuation server 652. The evacuation server 652 further includes a fire prediction engine 651 and an evacuation plan engine 653. The evacuation server 652 can be in communication with a mental models database 655 to perform one or more processes. The processes performed by each of the building evacuation system 650 and the evacuation server 652 are described in more detail in reference to FIG. 6C. The system 650 can be configured to receive real-time conditions of a fire from one or more of the signaling device 108, the hub 106, and the occupant device 671. The evacuation server 652 can use the received information to predict where the fire will spread (i.e., at the fire prediction engine 651), which predetermined evacuation plan to select and what guidance to provide to occupants, first responders, and other essential stakeholders (i.e., at the evacuation plan engine 653). Additionally, the evacuation plan engine 653 can determine what guidance to provide to stakeholders based at least in part on mental models that are stored in the mental models database 655. As described throughout this disclosure, evacuation plans and guidance can be determined based on characteristics and/or mental models associated with particular stakeholders and/or groups of stakeholders. For example, first responders receive a different evacuation plan and guidance instructions than building occupants.

Once evacuation plans and guidance are selected for each stakeholder and/or group of stakeholders, responder emergency plan information 659 can be transmitted to the first responder device 654 and occupant emergency plan information 657 can be transmitted to the occupant device 671. The first responder device 654 can output guidance 673 to the first responder. The occupant device 671 can output guidance 675 to the occupant. As described throughout this disclosure, the first responder device 654 can be a wearable device, such as a VR headset, glasses, and/or a helmet with a VR/AR device. The first responder device 654 can also be a mobile device, such as a smartphone and/or tablet. The occupant device 671 can be a wearable device, such as a smartwatch and/or glasses. The occupant device 671 can also be a mobile device, a computer, and/or a laptop.

Now referring to FIG. 6C, the building evacuation system 650, the evacuation server 652, and the first responder device 654 can be in communication, as previously described. The system 650 can collect fire data in step 656. This can include real-time information sensed by the one or more signaling devices 108 and/or the hub 106, as described throughout this disclosure. The fire data can include information about where a fire is located and how hot it is. Next, in step 658, the system 650 can collect data about building occupants. Occupant data can be received from the one or more signaling devices 108, the hub 106, and/or the occupant device 671, as described throughout this disclosure. Occupant data can include information about where the occupants are located and what conditions (i.e., handicaps) any of the occupants have. Once the fire and occupant data is collected, the system 650 can transmit the collect data in step 660 to the evacuation server 652.

Next, the server 652 can receive the fire and occupant data in step 662. Upon receiving the data, the fire prediction engine 651 (i.e., FIG. 6B) can predict the fire using AI and/or predictive analytics, as described throughout this disclosure (step 664). In this step, the engine 651 can predict where the fire is going to spread, how quickly it will spread, how hot the fire will get, and/or what damage the fire will cause.

Once the fire is predicted, the evacuation plan engine 653 (i.e., FIG. 6B) can determine an evacuation plan in step 666 for the building occupants. In step 666, the engine 653 can select one of the modeled egress strategies (i.e., FIGS. 1, 6A) for the occupants. In some implementations, the engine 653 can select more than one of the modeled egress strategies, where each selected egress strategy is chosen for a specific occupant. In this step, the engine 653 can also determine whether occupant(s) should egress or stay in place until first responders arrive at the building.

In step 668, the engine 653 can apply one or more mental models that are stored in the mental models database 655 (i.e., FIG. 6B) to the selected modeled egress strategies. The engine 653 can use a mental model associated with a particular occupant to determine how the occupant will respond to the selected modeled egress strategy. Based on how the occupant will respond to the selected evacuation plan, the engine 653 can generate occupant guidance data in step 670. As a result, such occupant guidance data can suggest instructions for the occupant to evacuate from the building, thereby eliminating a need for the occupant to make such decisions while under stress in a real-time emergency. Next, in step 672, the occupant guidance data can be transmitted to the building. The building evacuation system 650 can receive the occupant guidance data in 685. The system 650 can then output the guidance (i.e., egress instructions) in step 684. The guidance can be outputted through visual and/or audible devices installed throughout the building, mobile devices, and/or wearable devices in the building as well as on and/or carried by the occupants. As described in reference to FIG. 6B, the guidance information can be outputted at the occupant device 671. In other implementations, the guidance information can be outputted at one or more of the signaling devices 108 and/or the hub 106, as described throughout this disclosure.

Still referring to FIG. 6C, once the server 652 predicts the fire in step 664 the server 652 can also determine a rescue plan in step 674 for first responders. In step 674, the engine 653 can select one of the modeled rescue strategies (i.e., FIGS. 1, 6A) for the first responders. In some implementations, the engine 653 can select more than one of the modeled rescue strategies, where each selected strategy is chosen for a specific first responder.

In step 676, the engine 653 can apply one or more mental models that are stored in the mental models database 655 (i.e., FIG. 6B) to the selected modeled rescue strategies. The engine 653 can use a mental model associated with a particular responder to determine how the responder will respond to the selected modeled rescue strategy. Based on how the responder will respond and the selected rescue plan, the engine 653 can generate rescue guidance data in step 678. As a result, such rescue guidance data can suggest instructions for the responder to enter the building and help occupants, thereby eliminating a need for the rescuer to make such decisions while under stress in a real-time emergency. Next, in step 680, the rescue guidance data can be transmitted to the first responders.

The first responder device 654 can receive the fire and occupant data from at least one of the server 652 and/or the system 650. The device 654 can also receive the fire prediction from the server 652 in step 688. This information is important for the first responders to know what is happening at the emergency location. This information is also beneficial so that first responders can make decisions in real-time about how to enter the building and/or rescue occupants, in addition to following the rescue guidance information generated by the server 652. The device 654 receives the rescue guidance data from the server 652 in step 690.

In step 692, the device 654 can output the rescue guidance information, as described throughout this disclosure. For example, the guidance data can be outputted through visual and/or audible devices, mobile and/or wearable devices, and/or VR devices. In some implementations, the device 654 can output the fire and occupant data, the fire prediction, as well as the guidance data. In other implementations, the first responders can select what information is displayed/outputted at the device 654. In yet other implementations, the first responders can choose for different information to be displayed at the device 654 at different times. In other implementations, the device 654 can automatically output new information (i.e., an updated prediction of the fire spreading) to the first responders so that the first responders constantly receive pertinent information to respond to the emergency in real-time. Such seamless integration can assist the first responders in adequately responding to the emergency without having to make decisions in the moment and under high levels of stress.

Figure 7A:
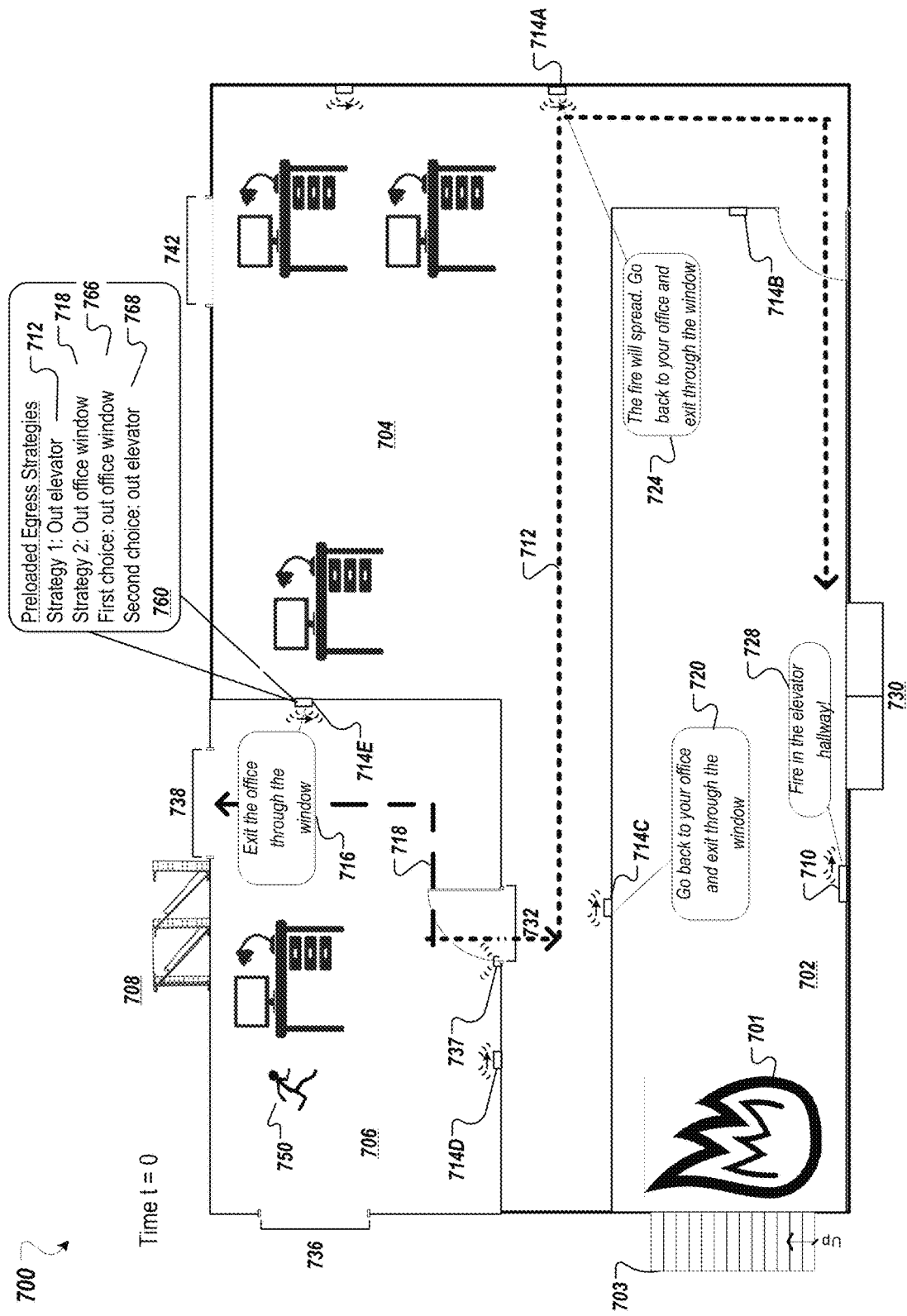

FIGS. 7A-C are conceptual diagrams of a building floor map with predicted egress strategies that are used to instruct occupants in the building about how to safely exit during an emergency. As depicted, one or more devices can be located in each of the rooms/spaces in a building 700, including hub 710 and signaling devices 714A-E. The signaling devices 714A-E and hub 710 can communicate via a wired and/or wireless connection, as previously discussed.

In some implementations, rooms, such as a private office 706, can include additional sensors, such as a sensor 737. The sensor 737 can detect a presence of a fire, a presence of an occupant, temperature of the private office 706, and other current conditions in real-time. For example, the sensor 737 can be a motion detector and/or a smart thermostat. In yet other implementations, the sensor 737 can be a smoke detector and/or a smart smoke detector, which can act as a primary sensor for determining an existence of a fire and its location. In other implementations, the sensor 737 can be a thermocouple heat sensor, which is beneficial to sense and report temperatures at various locations as a fire grows and spreads throughout the building 700. Optionally, the building 700 can include a sensor such as sensor 737 in each of the rooms/spaces in the building 700 along with additional sensors for redundancy (i.e., a sensor can be placed inside each private office at a door to each private office and a third sensor can be placed in a hallway between different spaces). In some implementations, multiple sensors can be positioned within an open office space 704 in order to be able to detect any changes in conditions in any region of the office space 704. Thermocouple heat sensors can also be placed along a stairwell 703 and throughout the building 700 with judicious placement near a ceiling height since heat rises and distributes itself. As a result, such sensors are less likely to be visible to building occupants but can still be effective in obtaining accurate temperature readings in real-time.

As discussed, the hub 710 and/or signaling devices 714A-E can also include integrated motion detectors and/or other types of sensors such that individual sensors, such as the sensor 737, are not required or heavily relied upon. In general, other devices that can communicate real-time conditions with the hub 710 and signaling devices 714A-E can include smart outlet covers, smoke detectors, sensors, etc. Moreover, any given device, such as a signaling device, can include a motion detector as well as any other devices discussed herein.

In some implementations, the hub 710 is a master monitoring system and other monitoring devices, such as the signaling devices 714A-E are secondary monitoring systems. In some implementations, each secondary monitoring system can take over control as a new master monitoring system if the hub 710 is out of commission (i.e., consumed by fire). A new master monitoring system can operate using last-received information from the hub 710 and information received from other secondary monitoring systems. In some implementations, all monitoring systems located in the building 700 can act as peer devices (i.e., pre-disaster and/or during a disaster), with no device designated as a master monitoring device or hub 710.

Additionally or alternatively, devices in the building 700 can connect to a cloud based service, to upload and download information provided by other devices, so that a given device can send and receive data even if a building or office space network is compromised, for example, by fire. During a disaster, devices may not be able to communicate on a local network, but a smart thermostat or signaling device in one room/space and the hub 710 may each be able to communicate via the cloud service (i.e., using a cellular network) and thereby exchange information with each other, using the cloud service as an intermediary.

FIG. 7A is a drawing of a floor, at time=0, in the building 700 that includes an elevator hallway 702 having an elevator 730 and the stairwell 703, the office space 704, and the private office 706. In this example, at time t=0, two egress strategies, a first strategy 712 and a second strategy 718, have been predicted, determined, and preloaded into a signaling device 714E. The signaling device 714E receives information 760 (i.e., FIGS. 1, 6) which can include (1) a list of potential egress strategies to select from (the first predicted egress strategy 712 and the second predicted egress strategy 718), (2) which strategy the signaling device 714E selects as an optimal egress strategy, a first choice 766, and (3) which strategy would be second best in case of an error in the signaling device 714E's selection, a second choice 768.

Importantly, in high-rise buildings, there typically are no more than one or two possible egress routes. Often during emergencies such as fires, the elevator 730 is inoperative, leaving building occupants with an option to take the stairwell 703 or jump out of a window, such as window 738. In predicting fire scenarios and determining optimal egress strategies, the system disclosed throughout this disclosure can assess whether it is feasible for occupants to exit through the window, such as the window 738. In the example depicted in FIG. 7A, the window 738 has a fire escape 708. This emergency device can make escape through the window 738 possible, thereby increasing a number of potential and safe egress routes out of the building 700 during an emergency. Other potential emergency devices can include an inflatable ladder and/or slide and/or a rope. In other implementations (not depicted), where the building 700 does not have a window that occupants can exit through, the information 760 may include only one predicted egress strategy and/or a strategy to remain in the building 700 until first responders come and rescue the occupants. For example, if a fire 701 blocks exit through the stairwell 703, the elevator 730 is inoperative during an emergency, and there is no fire escape 708 or emergency device to exit through any of the windows 736, 738, or 742, then the first and only predicted egress strategy 712 can instruct occupants to go into the private office 706 and close a door 732 until first responders come to the building 700.

Referring back to the example depicted in FIG. 7A, in some implementations, the private office 706 can include LED lights above the door 732 and above the windows 736 and 738, in addition to a speaker (i.e., integrated into the signaling device 714E), and sensors such as the sensor 737, which can be a thermocouple heat sensor. Lights, speakers, and/or sensors can also be co-located without wall outlets/sockets. All these devices can be located strategically, including near exit points themselves. These devices can be connected wirelessly or via wires to the hub 710 and/or other signaling devices 714A-E and other devices placed strategically throughout the building 700. This configuration can be applied to all the rooms/spaces in the building 700 and/or each room/space can have a different configuration of devices.

In this example, the fire 701 occurs in the elevator hallway 702, near the stairwell 703. Signaling device 714E in the private office 706 can receive a current condition of the fire 701 from the hub 710 that is located in the elevator hallway 702. The hub 710 can determine that a fire is present in the elevator hallway 702 by using sensors (i.e., temperature, infrared) that measure current conditions in real-time. The hub 710 can also be in communication with sensors in the hallway 702 that are configured to determine real-time conditions and transmit those conditions to the hub 710 and the other signaling devices 714A-E. The presence of the fire 701 can be determined, for example, based on one or more received temperature readings being more than a threshold temperature.

As another example, the hub 710 can receive a fire indication signal from one or more smoke detection devices located in the hallway 702. Other fire detection approaches can include IR (Infra-Red) fire detection and rate of rise temperature detection. Fire indication information can indicate which location(s) in the building 700 is on fire (or sufficiently close to a fire so as to be avoided by occupants of the building 700).

Once the signaling device 714E receives a notification that the fire 701 is present and where it is located, the signaling device 714E selects one of the strategies 718 and 712 for an occupant 750 to safely egress from the building 700, using techniques previously mentioned (i.e., FIG. 1). In this example, the signaling device 714E selected the second strategy 718, which then is reflected as the signaling device 714E's first choice 766. The second strategy 718 is to direct the occupant 750 out the window 738. Note, none of the strategies include exiting via the stairwell 703, because the server 100 as described in reference to FIG. 1 determined that the fire 701 started in a location that obstructs any access to the stairwell 703. Therefore, a strategy to use the stairwell 703 is not possible.

In the example of FIG. 7A, at time t=0, the signaling device 714E selected the second egress strategy 718 because based on real-time conditions of the fire 701 and/or conditions of the occupant 750, the occupant 750 may not have enough time to safely egress from the building 700 if the occupant 750 is instructed to take the first egress strategy 712 via the elevator 730. In this example, the server 100 described in reference to FIG. 1 may have received information that the elevator 730 remains in operation during an emergency. The server 100 may also have determined that some occupants, such as younger, more agile occupants and/or occupants located in the office space 704 can safely and quickly egress via the elevator 730, before the fire 701 spreads to the elevator 730. The server 100 had already simulated fires like that depicted in FIG. 7A and determined using predictive analytics how the occupant 750 would egress based on that occupant's age, agility, and other information. Thus, the server 100 may have determined that the occupant 750 would not be capable of safely egressing via the elevator 730 in a fire scenario like the one depicted in FIG. 7A. Therefore, all the signaling device 714E had to do in real-time was determine which of the modeled egress strategies would match up with the current, real-time conditions of the fire 701 in this scenario.

In some implementations, a temperature along the first egress strategy 712 can reach an untenable level even if a point along the strategy 712 towards the elevator 730 is not yet too hot. Thus, the safest exit is via the second egress strategy 718, out the window 738. The signaling device 714E can make this determination and strategy selection in real-time based on collecting temperature readings from other devices/sensors along each of the egress strategies 712 and 718. In some implementations (not depicted), a door that is opened and/or closed can also change the signaling device 714E's determination of which egress strategy to select. For example, if a fire starts in the private office 706 and an occupant is in the office space 704, wherein the door 732 is closed, a signaling device in the office space 704 can determine that there is enough time for the occupant to escape through the elevator hallway 702, via the stairwell 703 and/or the elevator 730. The signaling device in the office space 704 can make this determination based on the fact that the door 732 is closed (i.e., sensors, like the sensor 737, placed around the door 732 determine whether it is open or closed), which can increase the amount of time it would take for (1) the fire to spread from the private office 706 and into the office space 704 and (2) a temperature of the office space 704 to raise to an untenable level. Moreover, if the door is made of hollow-core or solid-core construction, that condition can also change the signaling device's determination of whether an egress strategy via the elevator 730 and/or the stairwell 703 is appropriate. It is worth noting that such a determination can also be made by the server 100 as depicted in FIG. 1, step B when simulating fire scenarios. In another example of a similar situation, if the door 732 is open, then the signaling device in the office space 704 can determine that the fire will quickly spread into the office space 704 and the temperature in the office space 704 will rapidly increase to an untenable level before the occupant can escape from the office space 704. Consequently, the occupant in the office space 704 may be directed to exit through the window 742, if the window has an emergency device (i.e., fire escape) for safe exit.

In a scenario such as that depicted in FIGS. 7A-C, if all occupants are in the private office 706 and/or the office space 704 when the fire 701 is in the elevator hallway 702, signaling devices in spaces 706 and 704 can work together to determine which egress strategy is optimal for all occupants to exit safely together. This determination can depend on the number of occupants, their ages and physical abilities, and a particular layout of spaces/rooms. Signaling devices in different rooms can select the same egress strategy out of the building 700 but can provide occupants in each of the rooms/spaces with particular instructions to exit those rooms and meet, for example, in the office space 704 to finish exiting together. For example, this would be advantageous where a disabled occupant needs help egressing out of the building 700.

In other scenarios, one occupant can receive instructions from a signaling device that direct the occupant to another occupant who is disabled or in need of some form of assistance to safely egress out of the building 700 (i.e., FIG. 1). The signaling devices can identify which occupants are in what rooms/spaces in real-time. The disclosed system can access information stored about each of the occupants. That stored information can form profiles for each occupant of the building 700 and can include an age of the occupant, any disabilities, an agility level, etc. The signaling devices and/or the disclosed system can use such information (i.e., occupant profiles) to determine how each occupant can safely egress from the building 700 and whether that occupant would need assistance from another occupant in the building 700. If assistance would be needed, the disclosed system can determine egress strategies that involve one or more occupants getting to and assisting the disabled occupant out of the building 700, both safely and quickly. Based on these determinations, the signaling devices can receive such egress strategies and their associated instructions. During a fire scenario, the signaling devices can then select an optimal egress strategy, whether it requires occupants to egress individually, in pairs, and/or in teams, and provide the associated instructions to occupants in the building 700.

In yet other implementations, visitor information (i.e., age, agility level, familiarity with the building 700, disabilities, etc.) can be provided to the disclosed system. This information can be provided by an occupant of the building 700 via a user computing device, a signaling device, and/or the hub 710. Once the visitor information is received by the disclosed system, the disclosed system can use such information to determine potential egress strategies for that visitor and whether the visitor would need assistance to egress in the event of a fire.

In yet other scenarios (not depicted), the signaling device 714E may select the second strategy 718 but something that is unpredicted can occur, such as the window 738 blowing out and/or the fire escape 708 breaking in the time it took the occupant 750 to move from a desk to the window 738. If such an unpredicted event was not previously predicted and considered in determining which egress strategy to select in real-time, then the signaling device 714E can make a correction and select a new egress strategy within seconds. In this case, where the signaling device 714E initially selected the second strategy 718, the signaling device can now make a selection correction and select the first strategy 712. In that case, the signaling device 714E can provide updated instructions to guide the occupant 750 out the elevator 730 rather than the window 738. Regardless, the use of predictive analytics, an abundance of data, and AI in the system and techniques described throughout this disclosure greatly reduce the need for correcting an egress strategy selection in real-time.

Still referring to FIG. 7A, once the signaling device 714E selects an egress strategy (in this case, it is the second strategy 718), the occupant 750 is instructed by the signaling device 714E to "exit the office through the window" (716). In this example, the outputted instructions are verbally communicated to the occupant 750. In other implementations, the outputted instructions can be communicated to the occupant 750 by using lights and/or LED strips that illuminate a path out of the building 700. In this example, multiple other signaling devices can also produce audio outputs to remind the occupant 750 to exit through the window 738 (i.e., signaling device 714C outside the private office 706 verbally outputs "Go back to your office and exit through the window" (720), signaling device 714A in the office space 704 verbally outputs "The fire will spread. Go back to your office and exit through the window" (724), and the hub 710 in the elevator hallway 702 near the elevator 730 verbally outputs "Fire in the elevator hallway!"). This is beneficial in the event that the occupant 750 leaves the private office 706 despite instructions signaling for the occupant 750 to leave through the window 738 in the private office 706. FIGS. 7A-C indicate examples of outputted instructions but in each implementation of the disclosed system, the instructions can vary, as demonstrated.

The signaling devices 714A-E can emit multi-colored, strobing, LED (Light Emitting Diode) laser light, and can be mounted low, at exit points (i.e., door, window) in each room/space. LED guiding lights can be mounted low in outlet-type components and/or along pathways leading to egresses from the building 700. As mentioned, the signaling devices 714A-E can also emit various audio and visual cues to occupants, for example. For instance, the signaling device 714E can include flashing lights that may indicate a direction the occupant 750 is to take to proceed to (or stay on) the selected egress strategy 718 out the window 738. A series of flashing lights (i.e., in a hallway) can also indicate a presence and direction of the selected egress strategy. Moreover, the signaling devices 714A-E can be placed on doors and windows to indicate the presence of respective doors and windows and to indicate whether a given door or window is part of an egress route. Different colors can indicate inclusion or exclusion of a given door, window, or pathway on an egress route.

For example, a flashing red signal (i.e., a red "X") on a doorway may indicate that the doorway is to be avoided (and the door kept shut). In the implementation depicted in FIG. 7A, the signaling device 714D or signaling device 714E can project a flashing red "X" over the door 732 so that the occupant 750 understands not to exit the private office 706. In another implementation, a flashing green light may indicate that a given door, window, or path segment is part of the selected egress route. In the example of FIG. 7A, the signaling device 714E can project the flashing green light on the window 738 to instruct the occupant 750 that he must exit through that window 738.

Audio instructions that are outputted by the signaling devices 714A-E can include a fire status description (i.e. "a fire has been detected by the stairwell"), directional clues (i.e. "go out of the door and to your left"), or more detailed instructions (i.e. "place a wet towel under the door and leave the door closed"). Audio instructions can be specific to the particular room/space in which an audio signaling device is located, based on the location of the room/space, the location of the detected fire, and a selected egress strategy.

Other types of signaling instructions and corresponding signals can be generated in the building 700. For example, information can be sent to mobile devices and/or wearable devices of occupants of the building 700 that directs the occupants to and on the selected egress route(s). The hub 710, secondary monitoring systems, and/or an application running on a mobile device may know where the mobile device (and associated user) are within the building 700, with respect to the fire 701 and the selected egress route(s). Such knowledge can be used to tailor instructions that are sent to and displayed (or played) on a given mobile device.

Other devices in the home may receive and present information related to the fire 701 and recommended evacuation of the building 700. For example, the hub 710 can communicate with various computing devices or displays located within the building 700. For example, the hub 710 can send information or signaling instructions to one or more desktop computing devices, smart televisions, or other devices located within the building 700. The computing devices can be configured to display information (i.e., a fire warning, egress route information), based on information received from the hub 710. In some implementations, the hub 710 can remotely control (i.e., turn on) devices that include a display, and instruct the devices to display (and/or play) information useful for evacuation of the building 700, such as egress route information that is specific to the location of the fire 701 and the location of the respective device. For example, the hub 710 can instruct office worker's computers that are connected to a network to display information useful for evacuation, such as notifying the workers that a fire was detected and how the workers should proceed to safety and/or evacuation.

FIG. 7B is a depiction of the building 700 at time t=1. This example demonstrates where a hypothetical occupant 770 would be had he taken the first predicted egress strategy 712 to exit through the elevator 730 of the building 700. As depicted, the fire 701 has moved closer to the elevator 730. Therefore, the signaling device 714E accurately predicted, at time t=0, where the fire 701 would spread at time t=1 to then select the optimal egress strategy (the second strategy 718 out the window 738) to safely exit the building 700.

FIG. 7C is a depiction of the building 700 at time t=2. This example demonstrates that, at time t=2, the hypothetical occupant 770 would be running into the fire 701 that has now spread out of the hallway 702 and closer to the office space 704 had the hypothetical occupant 770 been instructed to take the first predicted egress strategy 712 to exit through the elevator 730. However, at time t=2, the occupant 750 has safely exited the building 700 through the window 738 by the fire escape 708 by following the signaling device 714E's instructions 752 that are associated with the selected second egress strategy 718.

Figure 8:
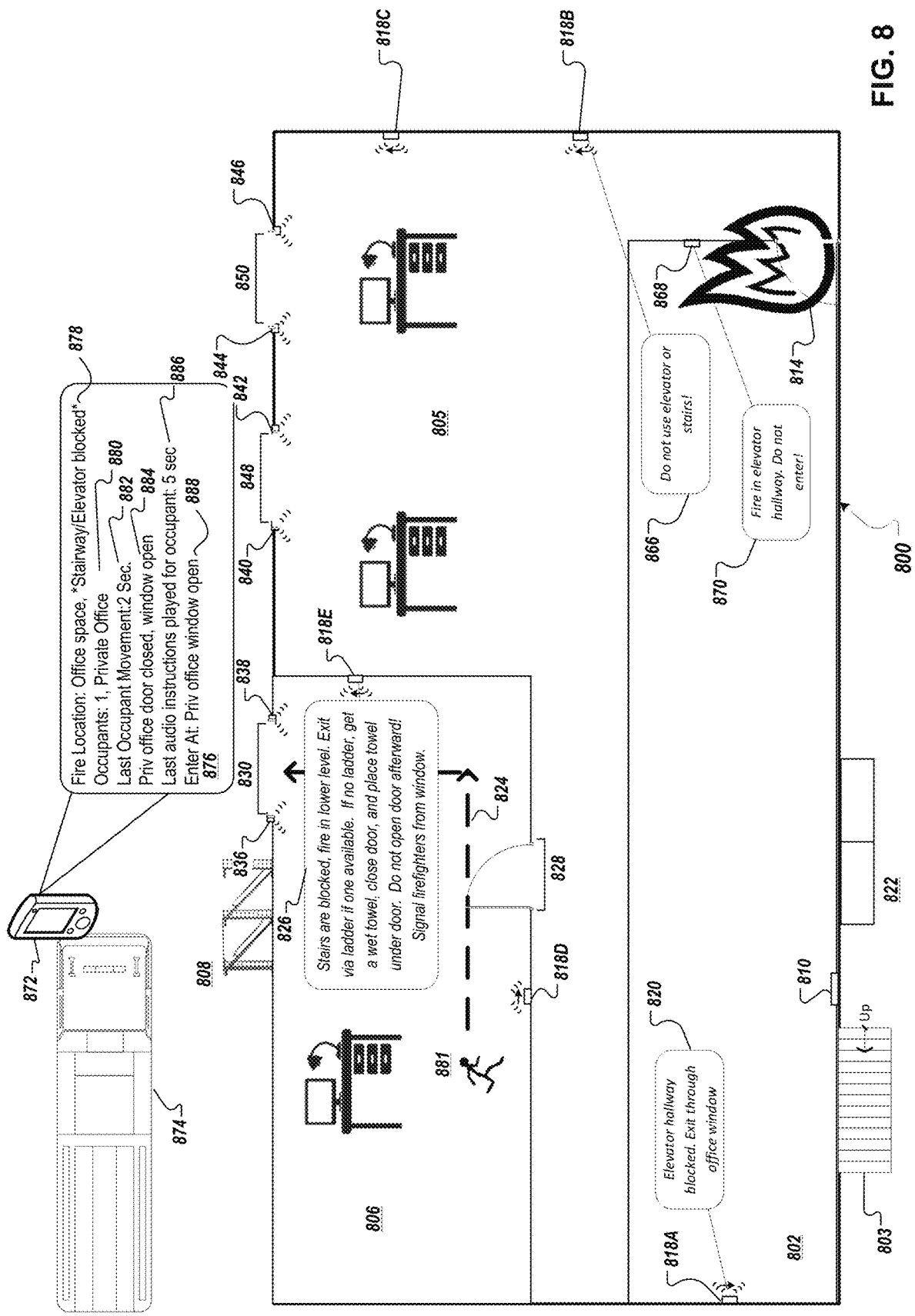
FIG. 8 is a conceptual diagram of yet another example floor map for which a predicted egress strategy is selected and used during an emergency.

FIG. 8 is a conceptual diagram of yet another example floor map for which a predicted egress strategy is selected and used during an emergency. This figure is another implementation of the scenario depicted in FIGS. 7A-C. In this implementation, a hub 810 can determine, and communicate to signaling devices 818A-E, that a fire 814 is blocking entry to an elevator hallway 802. Consequently, exiting via an elevator 822 and/or a stairwell 803 is not possible. The signaling device 818E can select an egress strategy from a list of preloaded, predicted egress strategies associated with exiting a private office 806 and instruct an occupant 881 in the private office 806 to exit through a window 830. The occupant 881 can receive an audio message 826 from the signaling device 818E that instructs the occupant 881 about what to do as part of the selected egress strategy. For example, the audio message 826 can direct the occupant 881 to use a ladder (i.e., fire escape 808), if available, to exit through the window 830. If the ladder is not available, the audio message 826 can direct the occupant 881 to get a wet towel, place it under a door 828, close the door 828 (and not subsequently open it), and signal firefighters/first responders from a window (i.e. the window 830). These types of audio instructions are beneficial in scenarios in which the only other possible egress route is blocked off by the fire 814. This is likely in a high-rise building because there are limited possible egress routes available. These audio instructions are also beneficial in scenarios in which fire fighters and/or other emergency assistance/first responders are on their way to help the occupant 881.

Referring back to the example depicted in FIG. 8, the signaling device 818E may also know that the door 828 is currently open (i.e., based on information provided by one or more sensors surrounding the door 828), and can direct the occupant 881 to get the wet towel based on the door 828 being currently open. If the signaling device 818E knows that the door 828 is currently closed, it can play an audio message that directs the occupant 881 to keep the door 828 closed. Moreover, the signaling device 818E may determine that the occupant 881 does not have access to a wet towel, and therefore may instruct the occupant 881 to just close the door 828.

Other signals can be emitted in the private office 806 to direct the occupant 881 on what to do during the emergency. For example, the signaling device 818E and a signaling device 818D can direct the occupant 881 towards the window 830 by emitting directional lights as disclosed throughout this disclosure. Further, devices 836 and 838 can also emit signals to indicate the presence of the window 830 (i.e., flashing lights, symbols above the window 830 indicating that the window 830 is the appropriate exit, green lights to indicate that the occupant 881 should go through the window 830, etc.).

Guidance similar to that provided in the private office 806 can be provided in other rooms/spaces throughout the building 800. For example, devices 840 and 842 and 844 and 846 can indicate the presence of a window 848 or a window 850, respectively. Signaling device 818C can emit a directional signal directing occupants to the window 848 and the window 850, and can play an audio recording (i.e., messages, instructions, etc.) that directs occupants to not use the elevator 822 and/or the stairwell 803. As previously mentioned, each signaling device can select an egress strategy from the list of predicted, preloaded egress strategies associated with the room that each signaling device is located in. Therefore, in the example above, the signaling device 818C located in an office space 805 can select an egress strategy from the list of predicted strategies associated with the office space 805 that directs an occupant in the office space 805 out through any of the windows 830, 848, and 850. The signaling device 818C can use the same current conditions collected from other signaling devices and sensors throughout the building 800 as the signaling device 818E in the private office 806 to determine that an egress strategy out through the elevator 822 and/or the stairwell 803 would not be the optimal and safest exit route.

Other signals can be played throughout the building 800. For example, signaling device 818B can play an audio messages 866 directing occupants to not use the elevator 822 or the stairwell 803. A device 868 can also play an audio message 870 directing occupants to not enter the elevator hallway 802. The various signals played by various devices in the building 800 can be emitted in response to egress strategies that each of the signaling devices 818A-E select.

In some implementations, as depicted in FIG. 8, fire fighter or other safety personnel can receive information provided by the hub 810. The hub 810 can send information to a fire fighter system or device and/or to a cloud service to enable the fire fighter system or device to retrieve the information from the cloud service. In some implementations, any of the signaling devices locate in the building 800 can transmit information and communicate with the fire fighter system. Information obtained from the hub 810 can be displayed, for example, on a fire fighter device 872, which can be a mobile device, as shown (i.e., in a fire truck 874 that is en route to the building 800).

The fire truck 874 may be en route, based on receiving an alarm from the hub 810. Information 876 displayed on the fire fighter device 872 includes fire location and blockage information 878, number and location of occupants 880 (i.e., for an occupant 881), last occupant movement information 882, status 884 of doors and windows in the building 800, a timeframe 886 of when last audio instructions were played for occupants in the building 800, and an entrance suggestion 888 so that the safety personnel know how to safely enter the building 800. In addition or alternatively, the information 876 can include location(s) of fire hydrants and/or sprinklers. The information 876 can be used by the fire fighters to better respond to the fire situation and to safely enter the building 800.

The number and location of occupants 880 and the last occupant movement information 882 can be generated based on motion detection devices in the building 800. Such devices can be integrating into the signaling devices 818A-E or can be standalone/independent devices, such as devices 836, 838, 840, 842, 844, and 846. Fire fighters can tailor their emergency response based on information that indicates who may be in the building 800 and where they are located. Occupant movement information can be generated and sent to a cloud service, on a periodic basis, for example. Security measures can be implemented so that occupant movement information is only accessed by authorized personnel, and optionally, only in cases of an emergency (i.e., only fire fighters can view occupant status information and only after an alarm has been received from the hub 810 or any of the signaling devices 818A-E). For some cases, the hub 810 may know that no occupant movement has been detected, i.e., within the last forty-eight hours, which may indicate that the building 800 is not occupied. Such information can be shared with the fire fighter system, so that fire fighters know that the building 800 may not be occupied and thus can determine whether they need to endanger themselves by entering the building 800 (or a certain floor of the building 800).

In some scenarios (not depicted), the building 800 can be vacant but the fire fighters still need to enter the building 800 to extinguish the fire before it spreads to other buildings, structures, and/or surrounding area(s). Consequently, the disclosed system can assist the fire fighters in assessing the danger of entering the burning building 800. For example, thermocouples and/or other types of sensing devices (i.e., smoke detectors, temperature readers, etc.) placed throughout the building 800 can be used to capture real-time conditions of a fire as it spreads through the building 800. The captured real-time conditions can be used by the disclosed system to determine whether the fire has spread. Consequently, the disclosed system can use this information to determine which windows, doors, exits, and/or entry points are still open and safe options for fire fighters to use when entering the building 800. Upon making this determination, the disclosed system can provide the possible entry points to the fire fighter system disclosed throughout and the fire fighters can then choose an entry point to safely enter the building 800.

While the fire fighters are in transit to the building 800, the fire fighter system can also receive a building/office layout for the building 800 from the disclosed system. The fire fighter system can also receive real-time updates about the fire pathway so that the fire fighters can use this information to determine which entrance to take into the building 800 and/or a particular floor in the building 800. It is also possible that the fire fighter system can automatically determine which entrance to take into the building 800 and then provide that information along with associated instructions to the fire fighters. Moreover, predictive analytics and AI can be used to predict flashovers. Flashovers are caused by radiative heat transfer from ignited materials in the interior of a room to its bounding surfaces in which pyrolysis on those surfaces releases particles and gases leading to sudden explosion. Therefore, by predicting where and when in the building 800 there may be flashovers, the disclosed systems can better determine an optimal and safe strategy/pathway for the fire fighters to enter the building 800. This can be beneficial to fire fighters whether they are entering a vacant burning building to prevent the fire from spreading and/or entering a burning building to save its occupants.

Referring back to FIG. 8, the fire fighter system can share information with the hub 810 and the signaling devices 818A-E, and the hub 810 may tailor guidance based on the received information. For example, an estimated fire fighter response time may be sent by a fire fighter system in response to an alarm received from the hub 810. The hub 810 and/or each of the signaling devices 818A-E can receive the estimated fire fighter response time. Based on the estimated response time, one or more of the signaling deices 818A-E can output additional instructions to the occupants (i.e., occupant 881). For example, if the expected response time is less than a threshold amount (i.e., less than two minutes), the signaling device 818E can play an audio message that directs the occupant 881 to open the window 830 and wave something out the window 830 to attract fire fighter attention. In other implementations, the signaling device 818E can be configured to start playing a sound or audio message to draw attention of fire fighters based on an estimated fire fighter response time. Estimated response times may be dynamically received, as mentioned, or may be predetermined and available to the signaling devices 818A-E and the hub 810 before the emergency.

Occupant movement information and information about known occupants may be used by signaling devices 818A-E to tailor guidance to occupants in the building 800. For example, if an occupant is detected in a room (i.e. the private office 806), then one or more signaling devices 818A-E can play audio messages in other rooms/spaces that indicate that the occupant may still be in a particular room and in need of assistance. In yet other implementations, and as previously discussed, information about known occupants can be used by the signaling devices 818A-E to determine a selection of the optimal egress strategy from the list of predicted, preloaded egress strategies.

In some implementations, after fire fighter arrival, movement of fire fighters within the building 800 can be determined by movement detection devices in the building 800. Location information of fire fighters (and occupants) can be made available to and presented on the fire fighter device 872, for assisting the fire fighter team during the emergency response.

The entrance suggestion 888 can be determined by the signaling devices 818A-Es' selection of optimal egress strategies. For example, in FIG. 8, the signaling device 818E selected an egress strategy that prompts the occupant 881 to exit through the window 830 if there is a ladder (i.e., the fire escape 808), and if there is not, to wave something out of the window 830 to attract the attention of fire fighters. The signaling device 818E communicates with the fire fighter device 872 that the occupant 881 will be exiting through the window 830 (entrance suggestion 888). Receiving this information at the fire fighter device 872 makes for faster and safer response time during an emergency. In other words, when fire fighters arrive at the building 800, they will not have to spend valuable time determining what is the best entrance into the burning building 800 and where the occupant 881 is located in the building 800. In scenarios where a signaling device must make one course correction, the information about the entrance suggestion 888 can be updated and transmitted to the fire fighter device 872 in real-time such that no time is lost for the fire fighters to safely assist the occupant 881. In some implementations, as depicted in FIG. 8, the entrance suggestion 888 can also provide some sort of indicator to make it easier for the fire fighters to identify the entrance point when they arrive at the scene. For example, in FIG. 8, the fire fighter device 872 receives information that the window 830 is open. In other examples, the device 872 can receive information about what corner/area/front/back/side of the building 800 that the fire fighters should enter, what floor of the building 800, whether a door or window is open or closed, whether something is coming out of the door or window to indicate it as an entrance, whether lights emitted from inside the building 800 indicate an entrance (i.e., LED light strips attached on top of the molding of a window), etc.

FIG. 9 depicts a flowchart of an example technique for predicting egress strategies and selecting the optimal egress strategy during an emergency. The technique described can be performed by the predictive pathway server 100 and each of the signaling devices 108A-D of FIG. 1. First, in step 902, the server receives building layout and user occupant information. As discussed, this information can be inputted by occupants through the hub device (i.e., FIG. 1 step A). This information can also be transmitted directly to the server by a builder when the building is being constructed and/or when the signaling devices and hub are being installed in the building.

Next, in step 904, the server can simulate fire scenarios in the building based on the information received in step 902 (i.e., FIG. 1, step B). The server also performs predictive analytics on an ability for occupants to safely egress from rooms/spaces in the building in step 906 (i.e., FIG. 1, step C). Based on the simulations and predictive analytics, the server can then model egress strategies in step 908 (i.e., FIG. 1, step D). As previously described, the server can create a list of egress strategies for each room/space in the building that are based on the ability of occupants in the building to safely egress from the building during an emergency.

Once egress strategies are modeled, the server can model signaling instructions that are associated with each of the modeled egress strategies in step 910 (i.e., FIG. 1, step E). In this step, the server can create both audio and visual signaling instructions or one or the other. Next, in step 912, the server can transmit the modeled egress strategies and associated signaling instructions to each signaling device (i.e., FIG. 1, step F). Each signaling device receives the list of modeled egress strategies and signaling instructions that are associated with the particular room/space that the signaling device is located in (914). For example, if the signaling device is located in the kitchen/common break room, then it will only receive a list of predicted egress strategies and signaling instructions for an occupant to exit from the kitchen/common break room. Likewise, if multiple signaling devices are located within a general office space, those signaling devices will receive a list of egress strategies and associated signaling instructions for an occupant to exit from the general office space.

Once each signaling device preloads the list of egress strategies, the signaling devices can receive current conditions in real-time in step 916 (i.e., FIG. 1, step G). As previously discussed, each signaling device can detect current conditions itself and/or it can communicate, wireless or wired, with the hub, other signaling devices, and/or other devices in the building (i.e., smart thermostat, temperature sensors, smoke detector, motion detector, etc.) about current conditions in any room in the building. Based on the current conditions, for example, a fire started in the kitchen, the signaling device can select an optimal egress strategy from the preloaded list of egress strategies in step 918 (i.e., FIG. 1, step H). The primary goal is that due to the simulations and predictive analytics performed beforehand by the server in steps 904-906, the signaling devices can select the optimal egress strategies without having to correct those selections in real-time.

Once an egress strategy is selected, the signaling device outputs the selected egress strategy based on the associated signaling instructions in step 920 (i.e., FIG. 1, Step I). As discussed, the signaling device can emit a signal, such as lights and/or audio, that indicate to the occupant the directions to take to exit the building quickly and safely. In some implementations, the associated signaling instructions can be outputted via output devices including but not limited to visual and/or audio fixtures in the building, one or more mobile devices (i.e., smartphone), one or more computing devices, computers, and/or laptops, one or more wearable devices (i.e., smartwatch), and/or one or more fixed VR devices (i.e., VR headset, VR glasses, TV, etc.).

Figure 10A:
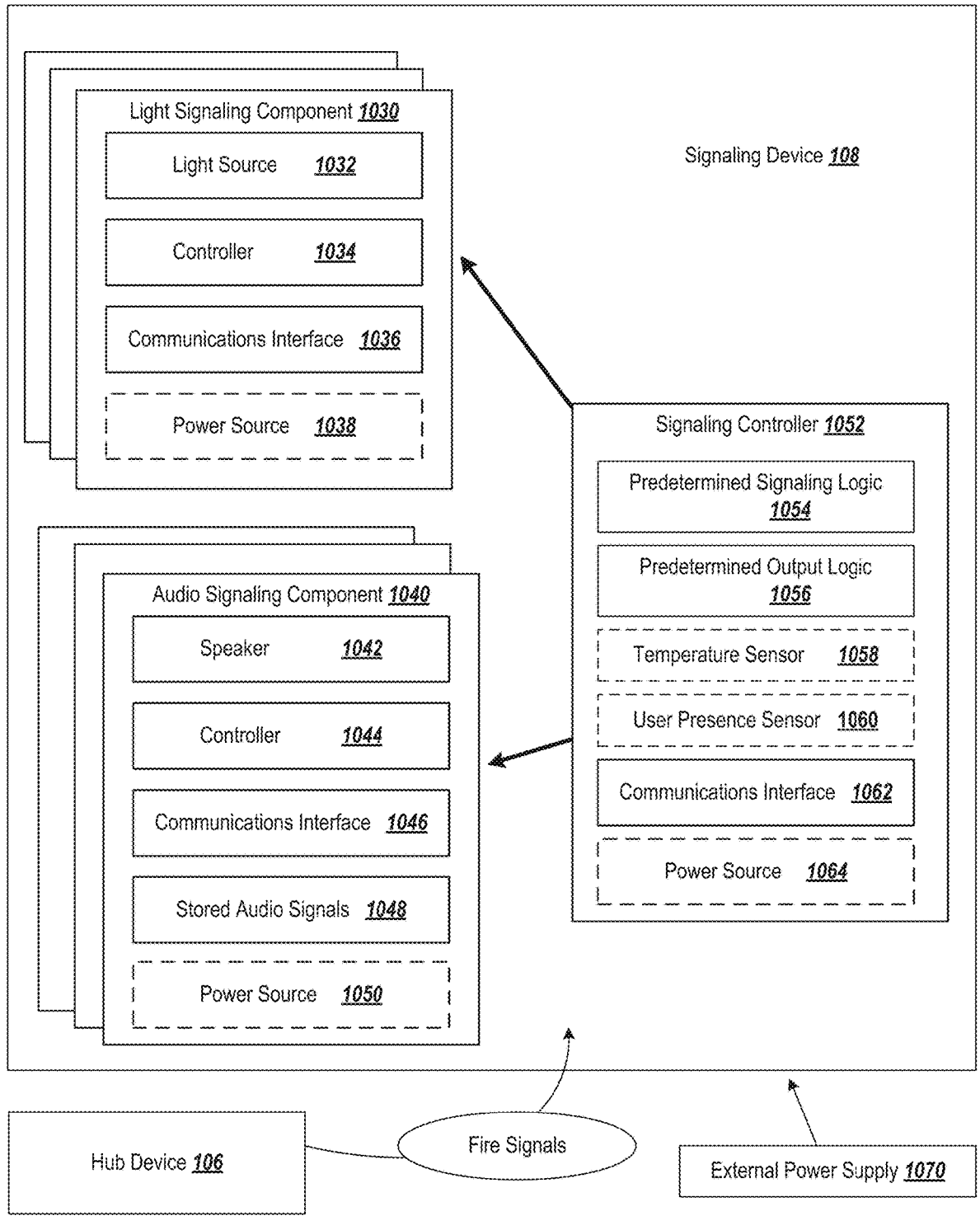
FIGS. 10A-B depict exemplary systems for providing emergency guidance and advisement.

FIG. 10A depicts another example system for providing emergency guidance and advisement. The signaling device 108 of FIG. 1 is used as an example in FIG. 10A. The signaling device 108 can be a singular device, as depicted in FIG. 10A, or it can optionally be spread out physically with separate components that can be in wired or wireless communication with each other (i.e., FIG. 10B). In this example in FIG. 10A, the signaling device 108 includes a light signaling component 1030, an audio signaling component 1040, and a signaling controller 1052. In some implementations, the signaling controller 1052 can have a one-to-one ratio of communication. Alternatively, in some implementations, the signaling controller 1052 can have a one-to-multiple ratio of communication. The audio signaling component 1040 and/or the light signaling component 1030 can optionally be integrated into/part of a same housing unit and/or circuit board as each other, the signaling controller 1052, and/or the entire signaling device 108 as a whole. Alternatively, and in some preferred implementations, each of the components in FIGS. 10A, 1030, 1040, and 1052, can be housed separately (i.e., separate devices; i.e., FIG. 10B). In yet other implementations, the controller 1052 can be in the same housing with the light signaling component 1030 and the audio signaling component 1040 can be housed separately. In other implementations, the controller 1052 and the audio signaling component 1040 can share the same housing unit/circuit board while the light signaling component 1030 is arranged separately. Moreover, in some implementations, the components 1030 and 1040 can be housed in the same unit and the signaling controller 1052 can be housed separately.

In the example of FIG. 10A, the components 1030 and 1040 are housed in the same unit (i.e., the signaling device 108) as the signaling controller 1052. Optionally, the signaling device 108 can have an external power supply 1070 (i.e., lithium battery). The signaling device 108 can also receive fire signals from the hub device 106 as described throughout this disclosure (i.e., FIG. 1). The signaling controller 1052 can communicate directly with the light signaling component 1030 as well as the audio signaling component 1040.

The signaling controller 1052 can include a predetermined signaling logic 1054, a predetermined output logic 1056, a temperature sensor 1058, and a user presence sensor 1060, as previously discussed in reference to FIG. 6. In some implementations, the controller 1052 may not have sensors 1058 and 1060, and can instead collect sensor information regarding a temperature and/or user presence from sensors placed throughout the building and/or other signaling devices in the building. The controller 1052 further can include a communications interface 1062 to facilitate communication (i.e., wired or wireless) with the other components, 1030 and 1040, comprising the signaling device 108. The communications interface 1062 can also facilitate communication between the signaling device 108, the hub device 106, other signaling devices throughout the building, and sensors in the building. The signaling controller 1052 can also optionally include a power source 1064 (i.e., battery) in order to power the signaling controller 1052 and/or the signaling device 108.

The light signaling component 1030 can include a light source 1032, a controller 1034, a communications interface 1036, and an optional power source 1038. The light source 1032 can be any form of lighting, including but not limited to an LED light strip (i.e., FIG. 10B). The light source 1032 can emit different colors, patterns, symbols based on signaling instructions communicated to the light signaling component 1030 by the signaling controller 1052. The controller 1034 can be configured to activate the light source 1032 based on receiving an activation signal/instruction from the signaling controller 1052. The communications interface 1036 is configured to allow the light signaling component 1030 to communicate with the signaling controller 1052. As mentioned, the power source 1038 can power the light signaling component 1030. In some implementations, the component 1030 may not include the power source 1038 and can instead rely on power from the external power supply 1070 that provides power to the signaling device 108 as a whole.

The audio signaling component 1040 can include a speaker 1042, a controller 1044, a communications interface 1046, stored audio signals 1048, and an optional power source 1050. The speaker 1042 can be any form or mechanism to output audio cues/instructions (i.e., FIG. 10B). The speaker 1042 can emit audio/verbal instructions to a user in the building based on signaling instructions communicated to the audio signaling component 1040 by the signaling controller 1052. The controller 1044 can be configured to activate the speaker 1042 based on receiving an activation signal/instruction from the signaling controller 1052. The communications interface 1046 is configured to allow the audio signaling component 1040 to communicate with the signaling controller 1052. The audio signaling component 1040 can further include the stored audio signals 1048, which can include a plurality of verbal instructions that are associated with each possible egress strategy out of a room that the signaling device 108 is located within. Therefore, when the signaling controller 1052 transmits an activation signal to the audio signaling component 1040, the activation signal can indicate which of the stored audio signals from the stored audio signals 1048 should be played. Then, the controller 1044 can activate the speaker 1042 by having the speaker output the selected audio signals from the stored audio signals 1048. As mentioned, the power source 1050 can power the audio signaling component 1040. In some implementations, the component 1040 may not include the power source 1050 and can instead rely on power from the external power supply 1070 that provides power to the signaling device 108 as a whole.

Figure 10B:
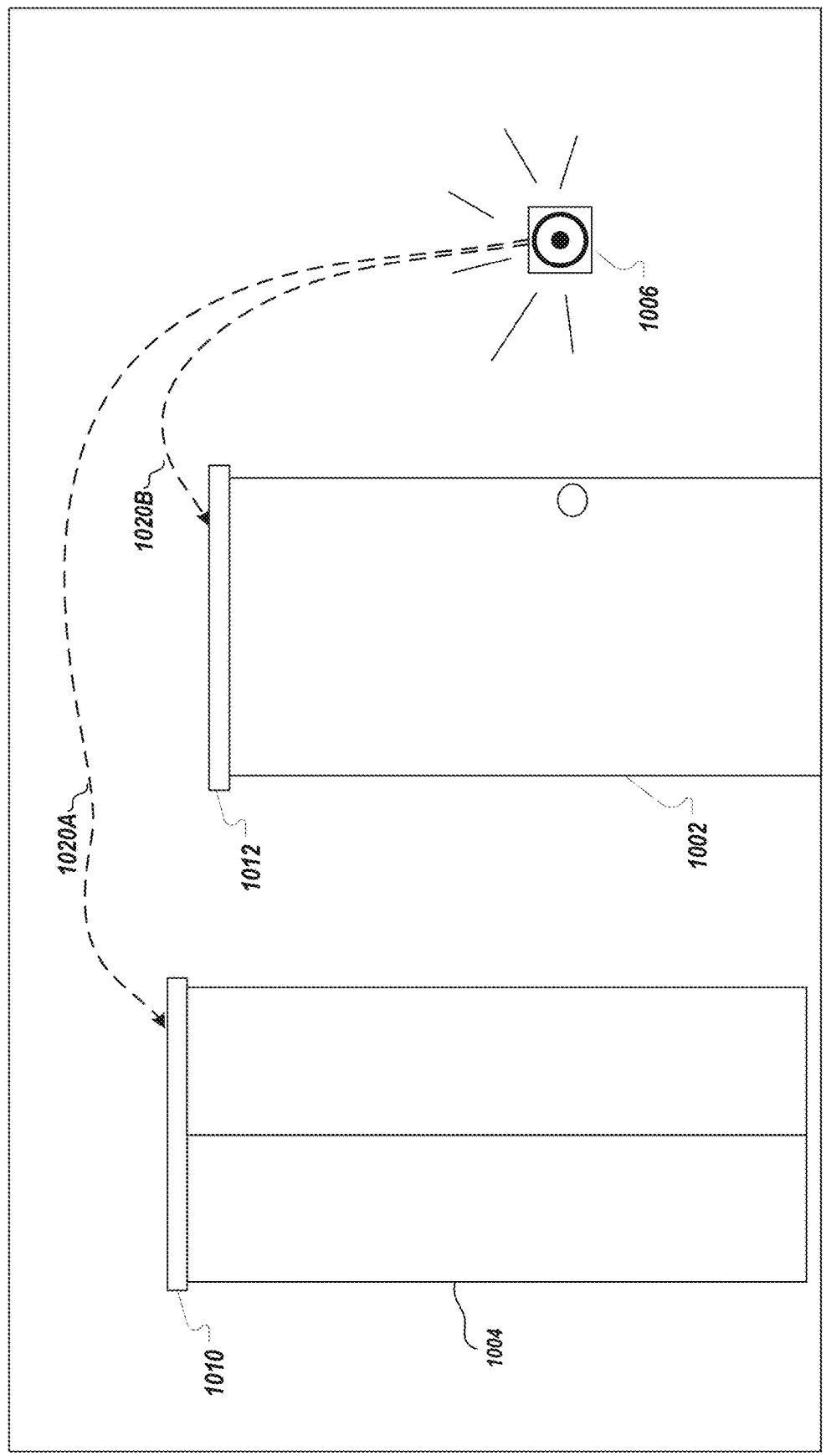

FIG. 10B depicts an example system for providing emergency guidance and advisement. In this example private office 1000, a door 1002 leading into another part of a building office space is fitted with a first LED strip 1012. The first LED strip 1012 can be attached on top of a molding of the door 1002 or anywhere else along a perimeter of the door 1002. A window 1004 is also fitted with a second LED strip 1010, which can be attached on top of a molding of the window 1004 or anywhere else along a perimeter of the window 1004. This way, the first and second LED strips 1012 and 1010 are not visible to an occupant or at least are not prominently displayed in the private office 1000.

In this example, a signaling device 1006 is also configured to a wall of the private office 1000. The signaling device 1006 can be retrofitted into an existing socket in the wall. In other implementations, the signaling device 1006 can be a plug-in that is inputted into an outlet in the room 1000. Here, the signaling device 1006 supports audio output. Thus, the signaling device 1006 communicates with the first and second LED strips 1012 and 1010 to display additional and/or alternative signals to an occupant during an emergency. The strips 1012 and 1010 and the signaling device 1006 can communicate through a wired and/or wireless connection, as previously discussed throughout this disclosure, wherein a communication signal (i.e., activation signal) between the signaling device 1006 and the first LED strip 1012 is signal 1020B and a communication signal between the signaling device 1006 and the second LED strip 1010 is signal 1020A. During an emergency and once the signaling device 1006 selects an optimal egress strategy, the signaling device 1006 can communicate visual signaling instructions to the first and second LED strips 1012 and 1010 via the signals 1020B and 1020A, respectively.

For example, if the selected egress strategy requires the occupant to exit through the door 1002, the signaling device 1006 can prompt (i.e., send an activating signal) the first LED strip 1012 to turn green, depict arrows, and/or flash. The signaling device 1006 can also prompt the second LED strip 1010 to turn red and/or depict "X" signals so that the occupant understands not to exit through the window 1004. The signaling device 1006 can optionally output audio messages instructing the occupant about how to exit in addition to the first and second LED strips 1012 and 1010 displaying visual signals for exiting the private office 1000.

Figure 11:
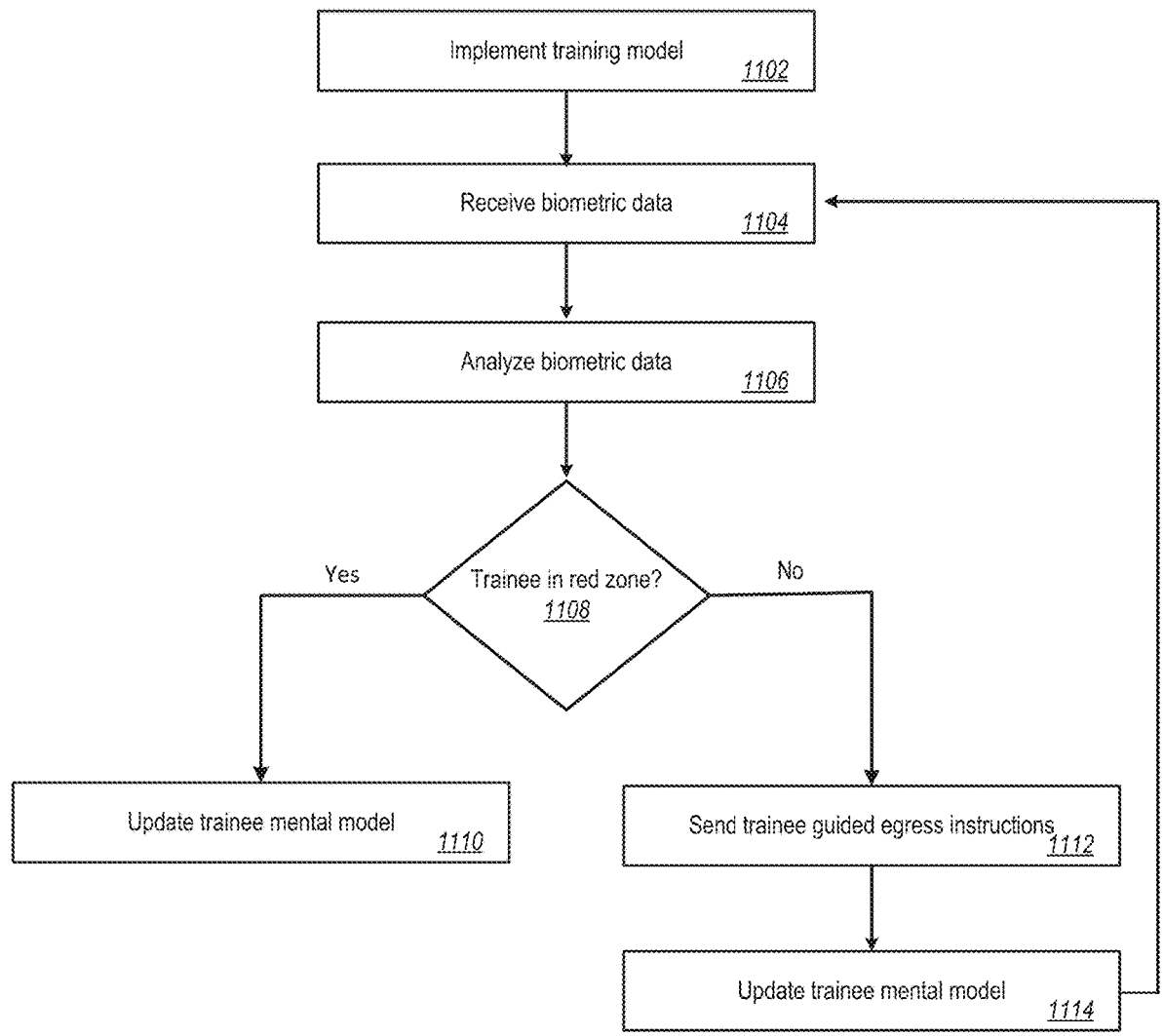
FIG. 11 depicts a flowchart of an example technique for activating emergency guidance during a simulation training model.
Figure 12:
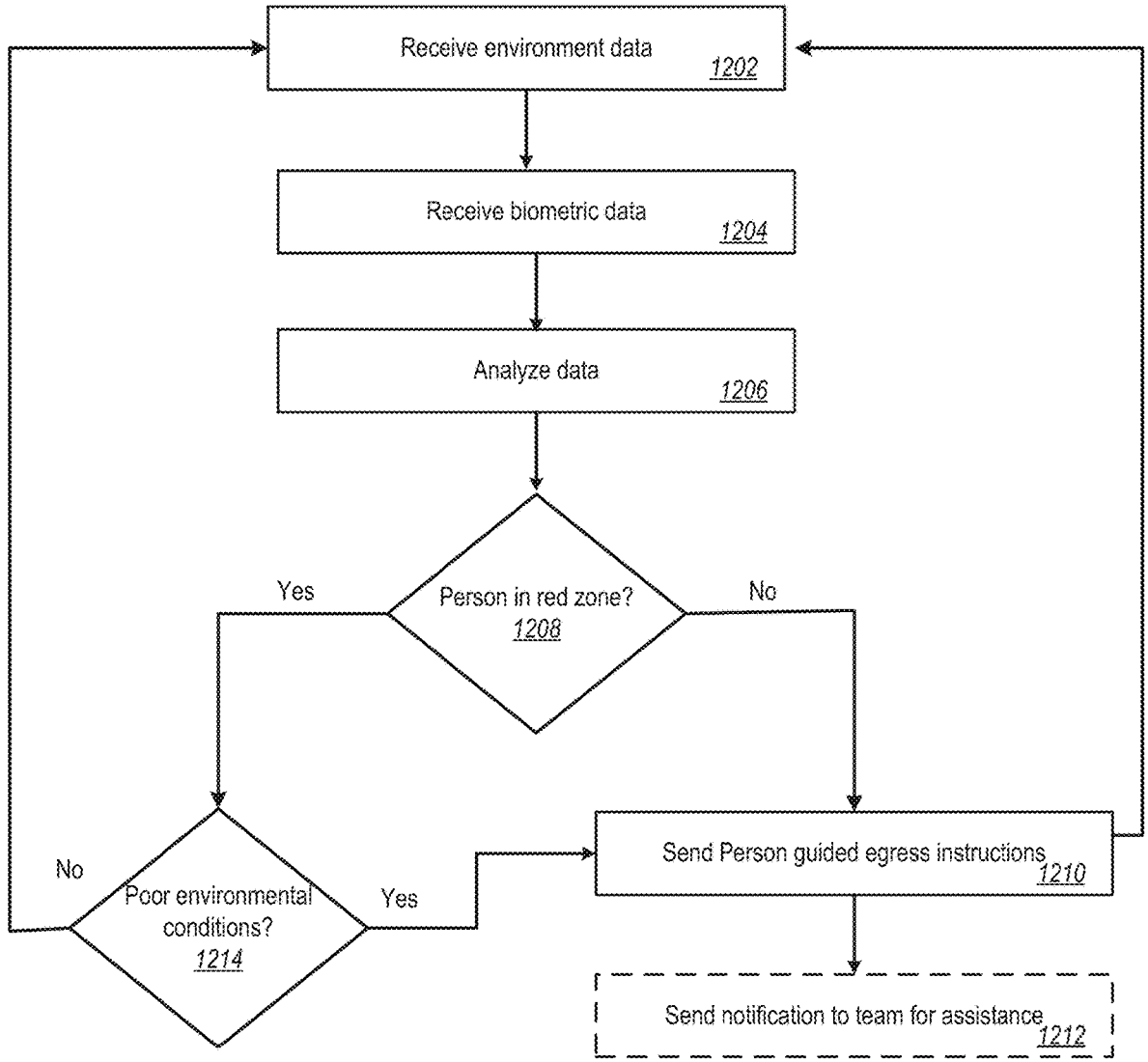
FIG. 12 depicts a flowchart of an example technique for activating emergency guidance during an emergency.

FIG. 11 depicts a flowchart of an example technique for activating emergency guidance during a simulation training model. FIG. 12 depicts a flowchart of an example technique for activating emergency guidance during an emergency. Typically, a person (i.e., first responder) undergoes a process of observing, orienting, deciding, and acting when placed in an emergency. However, some emergencies can present unexpected behaviors relative to a physical environment (i.e., a lot of smoke builds up in a room) that are challenging to predict and immediately respond to by the first responder. Implementing the techniques described herein with AI and/or predictive analytics can assist the first responder and other essential stakeholders in acting during such emergencies. The techniques described herein direct a computing system (i.e., the predictive fire pathway server 100 in FIG. 1 and the training model system 120 in FIG. 1) to observe, predict, and decide for the person in an emergency. The person then acts according to the instructions or decision of the computing system. As a result, a burden is lessened on the person or other stakeholders in an emergency who are not trained or suited for effective, coherent, and independent thinking and acting during a high stress and unpredictable emergency. As described in reference to FIGS. 11-12, the disclosed system can activate (i.e., switch on) a guidance mode in which the computing system provides the person with necessary guidance during an emergency.

Now referring to FIG. 11, in step 1102, a training model can be implemented, as described throughout this disclosure. The disclosed system can receive biometric data about a trainee undergoing the training model, as described throughout this disclosure (step 1104). In some implementations, the system can receive biometric data that is a heartrate of the trainee. The system can then analyze the biometric data in step 1106. In the example in which the biometric data is heartrate information, the system can determine whether the trainee's heartrate is in a desired zone. For example, where the trainee's heartrate is between 115 beats per minute and 145 beats per minute, the trainee can be classified as being in a red zone. In the red zone, typically a person's mind and body are geared for action. The person can observe, orient, decide and act on their own, despite surrounding environmental conditions or unexpected behaviors during the emergency. When the trainee is in the red zone, the computing system disclosed herein does not need to provide the trainee with guidance instructions because the trainee is able to address the situation on their own. In other words, guidance can be deactivated or turned off. Optimally, the trainee should be in the red zone during training as well as in a real-time emergency.

Where the trainee's heartrate is between 145 beats per minute and 175 beats per minute, the trainee can be classified as being in a grey zone. In the grey zone, typically a person experiences tunnel vision, deficit in depth perception, and a severe decline in motor skills. At this point, the trainee may need guidance from the computing system described herein. For example, appropriate guidance can be audio signals that notify the trainee of where there is danger and/or what egress pathways are obstructed by fire. In other words, guidance can be activated or turned on.

Where the trainee's heartrate is above 175 beats per minute, the trainee can be classified as being in a black zone. In the black zone, typically a person loses rational thought and decision-making capabilities. At this point, the person can be acting with "fight or flight" logic, which results in instinctive actions that may not be the smartest or safest actions to take during the emergency. At this point, the trainee needs guidance from the computing system described herein. For example, appropriate guidance can be instructions that tell the trainee where to go and/or what to do. When the trainee is in the black zone, the most amount of guidance can be provided. Therefore, guidance is activated or turned on.

Still referring to FIG. 11, after analyzing the biometric data and determining what zone the trainee is in (step 1106), it can be determined whether the trainee is in the red zone (step 1108). If the trainee is in the red zone, then the trainee's mental model can be updated in step 1110. The mental model can be updated with information indicating that the trainee can make optimal tactical decisions on their own in a simulated fire scenario. The mental model can also be updated with information indicating whether the trainee is in the middle instead of at the top (145 beats per minute) of the red zone. If the trainee is at the middle of the red zone, then the trainee is acquiring "stress inoculation." Stress inoculation occurs over time after frequent training and being immersed in fire scenarios of different difficulties. If the trainee is getting comfortable with fire scenarios of differing difficulty levels, then the trainee should receive more challenging and complex scenarios in future training to ensure continuous development of robust mental models, decision-making, and physical skills.

If, on the other hand, the computing system described throughout this disclosure determines that the trainee is not in the red zone (i.e., the trainee is transitioning to a lower level of the grey zone) (step 1108), then the system can send guided egress instructions to the trainee in step 1112. As mentioned above, if the trainee is in the grey zone, the system can provide audio outputs to a computing device, wearable device, and/or signaling device in the simulated environment. The audio outputs can be sounds or alerts indicating what areas of the simulated environment are obstructed by fire. Thus, when the trainee is in the grey zone, minimal guidance can be provided such that the trainee can still practice aspects of observing, orienting, deciding, and acting on their own.

Still referring to step 1112, if the trainee ever falls into the black zone, the system can provide more robust guidance instructions to the trainee. For example, the system can provide audio output that tells the trainee every action to take in the simulated environment. As a result, the system, using AI, predictive analytics, and the techniques described throughout this disclosure, can observe, predict, and decide for the trainee. The trainee can then act accordingly. Once the trainee receives guided instructions in step 1112, the trainee's mental model can be updated in step 1114. The mental model can be updated with information indicating that the trainee needed some form of computer-generated guidance to make it through the fire simulation model. This information is beneficial in order to assess the trainee's ability and skills in addressing high stress situations and emergencies. In a real-time emergency, the system described throughout can provide guidance instructions to the trainee such that in the real-time emergency, the trainee does not fall into the grey or black zones like they did in the training model. Moreover, this information is beneficial to provide additional training scenarios to the trainee that further develop the trainee's ability to observe, orient, decide, and act on their own, without guided instructions and get into the red zone. The training described herein is advantageous to prevent the trainee from ever falling below the red zone, whether during a training simulation or during a real-time emergency.

Once guided instructions are sent to the trainee in step 1112 and the trainee's mental model is updated in step 1114, steps 1104-1108 can be repeated. These steps can be repeated for a duration of the training model (i.e., until the trainee completes the training simulation). Repeating these steps is beneficial to determine how the trainee responds to the guided instructions. For example, if the trainee receives minimal guidance in step 1112 and their heartrate lowers enough to place them in the red zone, then the trainee's mental model can be updated with information indicating that the trainee can still observe, orient, decide, and act on their own with the aid of minimal guidance. Moreover, this information can indicate that with additional training models, the trainee can get into the red zone and observe, orient, decide, and act on their own without guidance during a real-time emergency. If, on the other hand, the trainee's heartrate does not lower or the trainee goes into the black zone after receiving minimal guidance in step 1112, then the trainee's mental model can be updated with information indicating that the trainee needs robust (i.e., step-by-step) guidance instructions during an emergency and/or that the trainee needs to undergo additional training models of varying levels of difficulty and complexity.

FIG. 12 depicts a flowchart of an example technique for activating emergency guidance during an emergency. During a real-time emergency, no matter how well trained a person, such as a first responder, is, unexpected conditions or behaviors in the physical environment can obstruct the person's ability to observe, orient, decide, and act on their own. In such situations, the computing system described herein can take over and automatically provide some level of guidance to the first responder to assist in their ability to decide and act.

First, in step 1202, the system described herein can receive environmental data. The environmental data can be captured by one or more sensors (i.e., temperature sensor, camera, etc.) and/or one or more devices (i.e., signaling device, fire alarm system, computing device, etc.) in real-time and communicated wirelessly to the system. The environmental data can indicate information such as temperature of a room, location of a fire, temperature of the fire, and/or an amount of smoke in the room. The system can receive environmental data pertaining to a particular room that the person (i.e., first responder, building occupant, other essential stakeholder) is in. The system can also receive environmental data pertaining to the entire building. Moreover, in step 1204, the system can receive biometric data about the person, as described throughout this disclosure. Steps 1202 and 1204 can be performed simultaneously or in any order.

Once the system receive environmental and biometric data, the system can analyze the data in step 1206. Analyzing the data can include determining whether the fire has moved along a path that the person is taking to egress or enter the building. Analyzing the data can also include determining a stress level of the person and/or what zone they are operating in, as previously described. The system can also analyze the environmental data with the biometric data to determine whether a condition in the physical environment is causing the person to experience a higher level of stress or higher heartrate.

Based on determinations made in analyzing the data in step 1206, the system can next determine whether the person is in the red zone in step 1208. If yes, the system can determine whether, nevertheless, there are poor environmental conditions in step 1214. Poor environmental conditions can include an increased amount of smoke that obstructs the person's view of the physical environment, thereby making it more challenging for the person to decide how to act. If there are poor environmental conditions, then the system described herein can provide some guided egress instructions to the person (step 1210). These instructions can notify the person of obstructions that the person cannot see because of the poor environmental conditions surrounding them. Since these instructions can provide minimal guidance, the person can still decide and act on their own. The system can optionally send a notification to one or more other people in the physical environment in step 1212. The notification can be received at a wearable device, a user computing device, and/or a signaling device positioned within the physical environment. The notification can prompt the one or more people to assist the person. The notification can also provide an indication to the one or more people about the poor environmental condition. The one or more people can be other building occupants, team members of the first responder, a building manager/emergency coordinator, and/or other essential stakeholders.

If there are no poor environmental conditions in step 1214, then the steps 1202-1208 can be repeated. These steps can be repeated for as long as it takes the person to get to a safe place in the physical environment. Repeating these steps is beneficial to ensure that the person can safely act in the real-time emergency. As a result, the computing system described herein can jump in at any moment in time in which a poor environmental condition, for example, is detected or the person moves into the grey or black zone to assist the person.

Still referring to FIG. 12, if the person is found to be outside of the red zone in step 1208, then the system can send the person guided egress instructions in step 1210, as described previously in reference to FIG. 11. The system can also optionally sent a notification to the one or more other people in the physical environment in step 1212, as described above. After sending the guided instructions to the person in step 1210, the steps 1202-1208 can be repeated for the reasons previously described.

The computing devices described in this document that may be used to implement the systems, techniques, machines, and/or apparatuses can operate as clients and/or servers, and can include one or more of a variety of appropriate computing devices, such as laptops, desktops, workstations, servers, blade servers, mainframes, mobile computing devices (i.e., PDAs, cellular telephones, smartphones, and/or other similar computing devices), computer storage devices (i.e., Universal Serial Bus (USB) flash drives, RFID storage devices, solid state hard drives, hard-disc storage devices), and/or other similar computing devices. For example, USB flash drives may store operating systems and other applications, and can include input/output components, such as wireless transmitters and/or USB connectors that may be inserted into a USB port of another computing device.

Such computing devices may include one or more of the following components: processors, memory (i.e., random access memory (RAM) and/or other forms of volatile memory), storage devices (i.e., solid-state hard drive, hard disc drive, and/or other forms of non-volatile memory), high-speed interfaces connecting various components to each other (i.e., connecting one or more processors to memory and/or to high-speed expansion ports), and/or low speed interfaces connecting various components to each other (i.e., connecting one or more processors to a low speed bus and/or storage devices). Such components can be interconnected using various busses, and may be mounted across one or more motherboards that are communicatively connected to each other, or in other appropriate manners. In some implementations, computing devices can include pluralities of the components listed above, including a plurality of processors, a plurality of memories, a plurality of types of memories, a plurality of storage devices, and/or a plurality of buses. A plurality of computing devices can be connected to each other and can coordinate at least a portion of their computing resources to perform one or more operations, such as providing a multi-processor computer system, a computer server system, and/or a cloud-based computer system.

Processors can process instructions for execution within computing devices, including instructions stored in memory and/or on storage devices. Such processing of instructions can cause various operations to be performed, including causing visual, audible, and/or haptic information to be output by one or more input/output devices, such as a display that is configured to output graphical information, such as a graphical user interface (GUI). Processors can be implemented as a chipset of chips that include separate and/or multiple analog and digital processors. Processors may be implemented using any of a number of architectures, such as a CISC (Complex Instruction Set Computers) processor architecture, a RISC (Reduced Instruction Set Computer) processor architecture, and/or a MISC (Minimal Instruction Set Computer) processor architecture. Processors may provide, for example, coordination of other components computing devices, such as control of user interfaces, applications that are run by the devices, and wireless communication by the devices.

Memory can store information within computing devices, including instructions to be executed by one or more processors. Memory can include a volatile memory unit or units, such as synchronous RAM (e.g., double data rate synchronous dynamic random access memory (DDR SDRAM), DDR2 SDRAM, DDR3 SDRAM, DDR4 SDRAM), asynchronous RAM (e.g., fast page mode dynamic RAM (FPM DRAM), extended data out DRAM (EDO DRAM)), graphics RAM (e.g., graphics DDR4 (GDDR4), GDDR5). In some implementations, memory can include a non-volatile memory unit or units (e.g., flash memory). Memory can also be another form of computer-readable medium, such as magnetic and/or optical disks.

Storage devices can be capable of providing mass storage for computing devices and can include a computer-readable medium, such as a floppy disk device, a hard disk device, an optical disk device, a Microdrive, or a tape device, a flash memory or other similar solid state memory device, or an array of devices, including devices in a storage area network or other configurations. Computer program products can be tangibly embodied in an information carrier, such as memory, storage devices, cache memory within a processor, and/or other appropriate computer-readable medium. Computer program products may also contain instructions that, when executed by one or more computing devices, perform one or more methods or techniques, such as those described above.

High speed controllers can manage bandwidth-intensive operations for computing devices, while the low speed controllers can manage lower bandwidth-intensive operations. Such allocation of functions is exemplary only. In some implementations, a high-speed controller is coupled to memory, display (e.g., through a graphics processor or accelerator), and to high-speed expansion ports, which may accept various expansion cards; and a low-speed controller is coupled to one or more storage devices and low-speed expansion ports, which may include various communication ports (e.g., USB, Bluetooth, Ethernet, wireless Ethernet) that may be coupled to one or more input/output devices, such as keyboards, pointing devices (e.g., mouse, touchpad, track ball), printers, scanners, copiers, digital cameras, microphones, displays, haptic devices, and/or networking devices such as switches and/or routers (e.g., through a network adapter).

Displays may include any of a variety of appropriate display devices, such as TFT (Thin-Film-Transistor Liquid Crystal Display) displays, OLED (Organic Light Emitting Diode) displays, touchscreen devices, presence sensing display devices, and/or other appropriate display technology. Displays can be coupled to appropriate circuitry for driving the displays to output graphical and other information to a user.

Expansion memory may also be provided and connected to computing devices through one or more expansion interfaces, which may include, for example, a SIMM (Single In Line Memory Module) card interfaces. Such expansion memory may provide extra storage space for computing devices and/or may store applications or other information that is accessible by computing devices. For example, expansion memory may include instructions to carry out and/or supplement the techniques described above, and/or may include secure information (e.g., expansion memory may include a security module and may be programmed with instructions that permit secure use on a computing device).

Computing devices may communicate wirelessly through one or more communication interfaces, which may include digital signal processing circuitry when appropriate. Communication interfaces may provide for communications under various modes or protocols, such as GSM voice calls, messaging protocols (e.g., SMS, EMS, or MMS messaging), CDMA, TDMA, PDC, WCDMA, CDMA2000, GPRS, 4G protocols (e.g., 4G LTE), and/or other appropriate protocols. Such communication may occur, for example, through one or more radio-frequency transceivers. In addition, short-range communication may occur, such as using a Bluetooth, Wi-Fi, or other such transceivers. In addition, a GPS (Global Positioning System) receiver module may provide additional navigation and location-related wireless data to computing devices, which may be used as appropriate by applications running on computing devices.

Computing devices may also communicate audibly using one or more audio codecs, which may receive spoken information from a user and convert it to usable digital information. Such audio codecs may additionally generate audible sound for a user, such as through one or more speakers that are part of or connected to a computing device. Such sound may include sound from voice telephone calls, may include recorded sound (e.g., voice messages, music files, etc.), and may also include sound generated by applications operating on computing devices.

Various implementations of the systems, devices, and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) can include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor.

To provide for interaction with a user, the systems and techniques described here can be implemented on a computer having a display device (e.g., LCD display screen, LED display screen) for displaying information to users, a keyboard, and a pointing device (e.g., a mouse, a trackball, touchscreen) by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, and/or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

The above description provides examples of some implementations. Other implementations that are not explicitly described above are also possible, such as implementations based on modifications and/or variations of the features described above. For example, the techniques described above may be implemented in different orders, with the inclusion of one or more additional steps, and/or with the exclusion of one or more of the identified steps. Additionally, the steps and techniques described above as being performed by some computing devices and/or systems may alternatively, or additionally, be performed by other computing devices and/or systems that are described above or other computing devices and/or systems that are not explicitly described. Similarly, the systems, devices, and apparatuses may include one or more additional features, may exclude one or more of the identified features, and/or include the identified features combined in a different way than presented above. Features that are described as singular may be implemented as a plurality of such features. Likewise, features that are described as a plurality may be implemented as singular instances of such features. The drawings are intended to be illustrative and may not precisely depict some implementations. Variations in sizing, placement, shapes, angles, and/or the positioning of features relative to each other are possible.

What is claimed is:

1. An emergency evacuation training system comprising:
an output device configured to output a training simulation model to a user during a time when no emergency is detected in a building that the user is associated with;
an input device configured to obtain training results of the user in response to participating in the training simulation model;
a biometric sensor configured to measure biometric characteristics of the user while the user is participating in the training simulation model; and
a training computing system configured to perform operations comprising:
generating the training simulation model that provides one or more possible emergency evacuation plans based on a user type for the user to practice, wherein the user type comprises at least one of a building occupant or a first responder, the one or more possible emergency evacuation plans comprising at least one egress plan and a plan to stay-in-place, wherein the training simulation model is configured to train the user to remain calm when presented with an instruction to follow the plan to stay-in-place during a future emergency in the building;
generating instructions for executing the training simulation model at the output device, wherein the instructions comprise presenting the training simulation model with augmented reality (AR) to train the user;
transmitting the instructions to the output device, wherein transmitting the instructions causes the output device to execute the training simulation model with the AR;
receiving, from the input device, data indicating the training results of the user;
receiving, from the biometric sensor, data indicating the biometric characteristics of the user while the user is participating in the training simulation model;
determining a training performance of the user based on the training results and the biometric characteristics that are generated by the biometric sensor, wherein the training performance indicates a stress level of the user in response to following the instruction to stay-in-place; and
iteratively adjusting the training simulation model based on the determined training performance of the user.

2. The system of claim 1, wherein generating the training simulation model is further based on evacuation information of associated with the building, wherein the evacuation information comprises locations of fire detectors and smoke detectors, occupant information, information about evacuation guidance devices, locations and types of emergency equipment, information about a sprinkler system, and information about elevators.

3. The system of claim 1, wherein the output device comprises at least one of a mobile device, a virtual reality ("VR") device, an AR device, or a wearable device.

4. The system of claim 1, wherein the biometric sensor comprises at least one of a wearable device, a heartrate monitor, a smartwatch, or smart clothing.

5. The system of claim 1, wherein the biometric characteristics comprise at least one of a heartrate, an EKG value, or an amount of sweat.

6. The system of claim 1, wherein the training results comprise information that indicates (i) whether the user completes at least one of the emergency evacuation plans, (ii) how fast the user completed the plan, (iii) whether the user received guidance to complete the plan, and (iv) what guidance the user received.

7. The system of claim 1, wherein the training computing system is configured to perform operations further comprising transmitting the adjusted training simulation model to the output device, wherein the output device executes the adjusted training simulation model for retraining of the user.

8. The system of claim 1, wherein generating the training simulation model comprises:
identifying one or more commonalities from evacuation information associated with a plurality of buildings, wherein the plurality of buildings comprises the building; and
generating the training simulation model based on the identified commonalities, the training simulation model being used to train the user to egress from any of the plurality of buildings during a future emergency.

9. The system of claim 8, wherein the one or more identified commonalities include at least one of locations of sensors in a building, egress strategies, egress instructions, or building layouts.

10. The system of claim 1, wherein the training computing system is configured to perform operations further comprising generating a mental model of the user based on the training performance, wherein the mental model indicates, based on the stress level of the user, how long it took the user to complete the training simulation model and what guidance the user received to assist the user in completing the training model.

11. The system of claim 1, wherein the user is at least one of a first responder, a building occupant, a building security officer, or an emergency incident commander.

12. The system of claim 1, wherein determining the training performance comprises determining whether the stress level of the user exceeds a predetermined threshold stress level.

13. The system of claim 12, wherein the stress level of the user is based, at least in part, on a duration of time for the user to complete the training simulation model, wherein the stress level is increased based on a determination that the duration of time exceeds a predetermined threshold amount of time expected for completing the training simulation model.

14. The system of claim 1, wherein during a real-time emergency in the building, the training computing system is configured to:
transmit the instructions to execute the training simulation model to an output device of a first responder while the first responder is traveling to the building, wherein transmitting the instructions to the output device of the first responder causes the output device of the first responder to execute the training simulation model with the AR while the first responder is traveling to the building and before the first responder arrives at the building.

15. The system of claim 14, wherein the training simulation model executed at the output device of the first responder provides instructions about how to enter the building, reach occupants in the building, and assist the occupants to reach safety.

16. The system of claim 1, wherein iteratively adjusting the training simulation model comprises increasing a complexity level of the training simulation model based on the stress level of the user being less than a threshold value.

17. The system of claim 1, wherein iteratively adjusting the training simulation model comprises decreasing a complexity level of the training simulation model based on the stress level of the user being greater than a threshold value.

18. The system of claim 1, wherein:
determining the training performance of the user comprises determining that a heartrate of the user that was detected by the biometric sensor exceeds a threshold value, and
the operations further comprise:
generating one or more additional training simulation models for the user based on a determination that the heartrate of the user exceeds the threshold value.

19. The system of claim 1, wherein the operations further comprise:
activating additional guidance instructions during execution of the training simulation model in response to determining that the biometric characteristics generated by the biometric sensor exceed predetermined threshold levels.

20. The system of claim 1, wherein iteratively adjusting the training simulation model comprises generating alternative evacuation plans intended to reduce the stress level of the user.

\* \* \* \* \*